(12) United States Patent
Wang

(10) Patent No.: US 8,709,997 B2
(45) Date of Patent: *Apr. 29, 2014

(54) PREVENTION AND TREATMENT OF OSTEOARTHRITIS

(75) Inventor: Jinxi Wang, Overland Park, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,312

(22) Filed: Aug. 31, 2012

(65) Prior Publication Data

US 2013/0004957 A1    Jan. 3, 2013

Related U.S. Application Data

(62) Division of application No. 12/407,536, filed on Mar. 19, 2012, now Pat. No. 8,263,546.

(60) Provisional application No. 61/038,591, filed on Mar. 21, 2012.

(51) Int. Cl.
  *A61K 38/16* (2006.01)
  *A61K 48/00* (2006.01)
  *A61P 19/02* (2006.01)

(52) U.S. Cl.
  USPC ......... 514/1.1; 514/16.8; 514/17.1; 514/44 R; 435/6.1; 435/7.1

(58) Field of Classification Search
  None
  See application file for complete search history.

*Primary Examiner* — Daniel C Gamett

(74) *Attorney, Agent, or Firm* — Workman Nydegger

(57) ABSTRACT

Subjects lacking Nfat1 display osteoarthritis in weight-bearing joints. Osteoarthritic changes associated with Nfat1 deficiency are characterized by articular cartilage degradation, articular chondrocyte proliferation/clustering, progressive articular surface destruction, periarticular chondro-osteophyte formation, and exposure of thickened subchondral bone. Methods of treating osteoarthritis, methods of diagnosis and early prediction of the onset of osteoarthritis, and methods for screening drug candidates that may be useful for treatment of osteoarthritis are presented.

12 Claims, 34 Drawing Sheets

SEQUENCE LISTING

```
<160> NUMBER OF SEQ ID NOS: 93

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gactatctga accctatcg                                                  19

<210> SEQ ID NO 2
<211> LENGTH: 2742
<212> TYPE: DNA
<213> ORGANISM: Mus sp.

<400> SEQUENCE: 2
aggagtggga gcacggggag ccagagcccc ggagcggagc ctaggcgctg cagcgtctgc    60
gccgctccgc cagatcacag cacacggtcc ccagcctgct gatcccggcg cctacagatg   120
cagcgccccg cattgcgcag gccgggcccc cgccagcccc tccgcaccat ggggtctgcg   180
gaccgagaac ctctccaata atgtcacctc gaaccagcct cgccgaggac agctgcctgg   240
gccgacactc gcccgtgccc cgtccggcat cccgctcctc ctcacccggt gccaagcgga   300
ggcattcgtg cgcagaggct ttggttgctc ctctgcccgc agcctcaccc cagcgctccc   360
ggagcccctc gccacagccc tcgcctcacg tggcactgca ggacgacagc atcccgctg    420 ggtacccccc cacggccggc tctgctgttc tcatggatgc cctcaacacc ctggccaccg   480
actcgccctg cgggatcccc tccaagatat ggaagaccag tcctgacccg acgcctgtgt   540
ccaccgctcc gtccaaggct ggcctggccc gccacatcta ccctactgtg gagttcctgg   600
```

```
ggccatgtga gcaggaggag aggaggaatt ccgctccaga gtccatcctg ctggtaccac    660
ctacttggcc caagcagttg gtgccggcca ttcccatctg cagcatccct gtgactgcat    720
ccctcccacc actcgagtgg ccactctcca atcagtcggg ctcctatgag ctacggattg    780
aggtccaacc caagccccat caccgggccc actatgagac ggagggcagc cgtggcgctg    840
tcaaagcccc aacaggagga caccctgtgg tgcagctcca cggctacatg gagaacaagc    900
ctctggggct tcagatcttc attgggacag cagatgagag gatccttaag ccgcacgcct    960
tctaccaagt acacaggatc actgggaaaa cggtcaccac cacgagctat gagaagatcg   1020
taggcaacac caaggtcctg gagatccccc tggagccaaa gaacaacatg agagccacca   1080
tcgactgtgc aggcatcctg aagctccgaa acgctgacat cgagctgcgg aagggcgaga   1140
cggacatcgg caggaagaac acgcgtgtgc gcctggtgtt ccgcgtgcac gtcccagagc   1200
ccagtgggcg catcgtctcc ctgcaggctg cgtccaaccc catcgagtgc tctcagcgct   1260
ctgcccacga gctgcccatg gtggagagac aagacatgga cagctgcctg gtctacgggg   1320
gccagcagat gatcctcacg ggccagaact tcacagcgga gtccaaggtt gtgttcatgg   1380
agaagactac aggacctgca gggacctgtg agactcggcc tttgcccatc tctctgatct   1440
cagctgaccg tctctccccc tggctttccc ggctgcagag aaaccctcct ggctctgtct   1500
tcagatgctc cgtgctcctt cctgccccag gatcttcgct tgtgctgctg gctctgtaac   1560
attctgccct tgttccctcg catactgtgt ctcctcttac tgggaagcca ttctccctga   1620
gtggtgttcg tgttcaaagg ctcatggctc aactgtccag cccaatgtca cttttttgcct   1680 gtcccttttc cacgctttat tctccaggtg acactcagtg tttcacctgt ctgtctgctc   1740
tctcttgggt cctctggttc ccatactaga ctgtcggttc cttgggagca gggatacact   1800
gtttgctgct gcactcacaa ttatagaatt atctctgtgc gtactaagtg tgcatgtgtc   1860
atgctgaagg aaagcggtgt tccccccttt attgcctctc ccaccatgag aagcggctgt   1920
attatcccca ttttacagat aagttgaggt tcaaagctat caagccagag accctgggtt   1980 agccctcca actggggaaa gatctggaac cccagcatgt cattttcctg atctctggag    2040
tgatttctct tgtcatgtca aagagaagtc aagaggatag ttctgttcct gtgtgttcta   2100
caaaataaaa gatgcatagc cttcaaggga aggtcaggct gggaggccag gctgttcctg   2160
ccctcgctgg gaaccctggc ccctggcccc tggccctgag cagagtcggg ggtcccagca   2220
aaacattgca aaacaggaaa aaatctaagg acacaaaaac acaagccgtg tggttgagga   2280
gacagggttg ccatggctcc aggcgactct cgaggctggc gtgatccagt gttttggaag   2340
gttcctccat gtgacacagg gttttggaat tcttcagctg gtaagtcctt cttaattcag   2400 gccctagcc ctggccaagc cactcccggg ctctcggtgt cccgcggggg cgtagactgg    2460
acacaggccc acatcaaatt actcagctct acaactaaaa gttttgaag cgggtttctt    2520 gttttgttgg atggttttct tggctcggtc tgatggcaga ggctcccatc acctgtcggg   2580
aaggcaaatt gatttttttt tttcaagagg aggcgtgggt ggtggaattc ccttttaacc   2640
gatgagtcac cgagggcagc cgtgactcac tttattattc ccaggttccc aaaggctata   2700
tcgcttttgg gctttgttta ataaatagaa tcatgtatgc gc                      2742
```

<210> SEQ ID NO 3
<211> LENGTH: 452
<212> TYPE: PRT
<213> ORGANISM: Mus sp.

<400> SEQUENCE: 3

```
Met Ser Pro Arg Thr Ser Leu Ala Glu Asp Ser Cys Leu Gly Arg His
1               5                   10                  15

Ser Pro Val Pro Arg Pro Ala Ser Arg Ser Ser Pro Gly Ala Lys
            20                  25                  30

Arg Arg His Ser Cys Ala Glu Ala Leu Val Ala Pro Leu Pro Ala Ala
            35                  40                  45

Ser Pro Gln Arg Ser Arg Ser Pro Ser Pro Gln Pro Ser Pro His Val
50                  55                  60

Ala Leu Gln Asp Asp Ser Ile Pro Ala Gly Tyr Pro Pro Thr Ala Gly
65                  70                  75                  80

Ser Ala Val Leu Met Asp Ala Leu Asn Thr Leu Ala Thr Asp Ser Pro
                85                  90                  95

Cys Gly Ile Pro Ser Lys Ile Trp Lys Thr Ser Pro Asp Pro Thr Pro
                100                 105                 110

Val Ser Thr Ala Pro Ser Lys Ala Gly Leu Ala Arg His Ile Tyr Pro
            115                 120                 125

Thr Val Glu Phe Leu Gly Pro Cys Glu Gln Glu Arg Arg Asn Ser
            130                 135                 140

Ala Pro Glu Ser Ile Leu Leu Val Pro Pro Thr Trp Pro Lys Gln Leu
145                 150                 155                 160

Val Pro Ala Ile Pro Ile Cys Ser Ile Pro Val Thr Ala Ser Leu Pro
                165                 170                 175

Pro Leu Glu Trp Pro Leu Ser Asn Gln Ser Gly Ser Tyr Glu Leu Arg
            180                 185                 190

Ile Glu Val Gln Pro Lys Pro His Arg Ala His Tyr Glu Thr Glu
            195                 200                 205

Gly Ser Arg Gly Ala Val Lys Ala Pro Thr Gly His Pro Val Val
        210                 215                 220

Gln Leu His Gly Tyr Met Glu Asn Lys Pro Leu Gly Leu Gln Ile Phe
225                 230                 235                 240

Ile Gly Thr Ala Asp Glu Arg Ile Leu Lys Pro His Ala Phe Tyr Gln
            245                 250                 255

Val His Arg Ile Thr Gly Lys Thr Val Thr Thr Thr Ser Tyr Glu Lys
            260                 265                 270

Ile Val Gly Asn Thr Lys Val Leu Glu Ile Pro Leu Glu Pro Lys Asn
            275                 280                 285

Asn Met Arg Ala Thr Ile Asp Cys Ala Gly Ile Leu Lys Leu Arg Asn
290                 295                 300

Ala Asp Ile Glu Leu Arg Lys Gly Glu Thr Asp Ile Gly Arg Lys Asn
305                 310                 315                 320

Thr Arg Val Arg Leu Val Phe Arg Val His Val Pro Glu Pro Ser Gly
            325                 330                 335

Arg Ile Val Ser Leu Gln Ala Ala Ser Asn Pro Ile Glu Cys Ser Gln
            340                 345                 350

Arg Ser Ala His Glu Leu Pro Met Val Glu Arg Gln Asp Met Asp Ser
            355                 360                 365

Cys Leu Val Tyr Gly Gly Gln Gln Met Ile Leu Thr Gly Gln Asn Phe
            370                 375                 380

Thr Ala Glu Ser Lys Val Val Phe Met Glu Lys Thr Thr Gly Pro Ala
385                 390                 395                 400

Gly Thr Cys Glu Thr Arg Pro Leu Pro Ile Ser Leu Ile Ser Ala Asp
                405                 410                 415

Arg Leu Ser Pro Trp Leu Ser Arg Leu Gln Arg Asn Pro Pro Gly Ser
```

```
        420              425               430
Val Phe Arg Cys Ser Val Leu Leu Pro Ala Pro Gly Ser Ser Leu Val
    435              440               445

Leu Leu Ala Leu
    450

<210> SEQ ID NO 4
<211> LENGTH: 3166
<212> TYPE: DNA
<213> ORGANISM: Homo sapiens

<400> SEQUENCE: 4
agcaggaagc tcgcgccgcc gtcgccgccg ccgctcagct tccccgggcg cgtccaggac    60
ccgctgcgcc aggcgcgccg tccccggacc cggcgtgcgt ccctacgagg aaagggaccc   120
cgccgctcga gccgcctccg ccagccccac tgcgaggggt cccagagcca gccgcgcccg   180
ccctcgcccc cggccccgca gccttcccgc cctgcgcgcc atgaacgccc cgagcggca   240 gccccaaccc gacggcgggg acgccccagg ccacgagcct gggggcagcc ccaagacga   300 gcttgacttc tccatcctct tcgactatga gtatttgaat ccgaacgaag aagagccgaa   360
tgcacataag gtcgccagcc caccctccgg acccgcatac cccgatgatg tcctggacta   420
tggcctcaag ccatacagcc cccttgctag tctctctggc gagccccccg ccgattcgg   480 agagccggat agggtagggc cgcagaagtt tctgagcgcg gccaagccag cagggcctc   540 gggcctgagc cctcggatcg agatcactcc gtcccacgaa ctgatccagg cagtggggcc   600
cctccgcatg agagacgcgg gcctcctggt ggagcagccg cccctggccg gggtggccgc   660
cagcccgagg ttcaccctgc ccgtgccggg cttcgagggc taccgcgagc cgctttgctt   720 gagcccgct agcagcggct cctctgccag cttcatttct gacaccttct cccctacac   780 ctcgccctgc gtctcgccca ataacggcgg gcccgacgac ctgtgtccgc agtttcaaaa   840
catccctgct cattattccc ccagaacctc gccaataatg tcacctcgaa ccagcctcgc   900
cgaggacagc tgcctgggcc gccactcgcc cgtgccccgt ccggcctccc gctcctcatc   960
gcctggtgcc aagcggaggc attcgtgcgc cgaggccttg gttgccctgc cgcccggagc   1020
ctcaccccag cgctcccgga gccctcgcc gcagccctca tctcacgtgg caccccagga   1080
ccacggctcc ccggctgggt acccccctgt ggctggctct gccgtgatca tggatgccct   1140
gaacagcctc gccacggact cgccttgtgg gatcccccc aagatgtgga gaccagccc   1200 tgaccctcg ccgtgtctg ccgccccatc caaggccggc ctgcctcgcc acatctaccc   1260
ggccgtggag ttcctggggc cctgcgagca gggcgagagg agaaactcgg ctccagaatc   1320
catcctgctg gttccgccca cttggcccaa gccgctggtg cctgccattc ccatctgcag   1380
catcccagtg actgcatccc tccctccact tgagtggccg ctgtccagtc agtcaggctc   1440
ttacgagctg cggatcgagg tgcagcccaa gccacatcac cgggcccact atgagacaga   1500
aggcagccga ggggctgtca agctccaaac tggaggccac cctgtggttc agctccatgg   1560
ctacatggaa aacaagcctc tgggacttca gatcttcatt gggacagctg atgagcggat   1620
ccttaagccg cacgccttct accaggtgca ccgaatcacg gggaaaactg tcaccaccac   1680
cagctatgag aagatagtgg gcaacaccaa agtcctggag ataccttgg agcccaaaaa   1740 caacatgagg gcaaccatcg actgtgcggg gatcttgaag cttagaaacg ccgacattga   1800
gctgcggaaa ggcgagacgg acattggaag aaagaacacg cgggtgagac tggttttccg   1860
agttcacatc ccagagtcca gtggcagaat cgtctcttta cagactgcat ctaaccccat   1920
```

```
cgagtgctcc cagcgatctg ctcacgagct gcccatggtt gaaagacaag acacagacag    1980
ctgcctggtc tatggcggcc agcaaatgat cctcacgggg cagaacttta catccgagtc    2040
caaagttgtg tttactgaga agaccacaga tggacagcaa atttgggaga tggaagccac    2100
ggtggataag gacaagagcc agcccaacat gcttttttgtt gagatccctg aatatcggaa    2160
caagcatatc cgcacacctg taaaagtgaa cttctacgtc atcaatggga agagaaaacg    2220
aagtcagcct cagcacttta cctaccaccc agtcccagcc atcaagacgg agcccacgga    2280
tgaatatgac cccactctga tctgcagccc cacccatgga ggcctgggga gccagcctta    2340 ctaccccag cacccgatgg tggccgagtc cccctcctgc ctcgtggcca ccatggctcc    2400
ctgccagcag ttccgcacgg ggctctcatc ccctgacgcc cgctaccagc aacagaaccc    2460
agcggccgta ctctaccagc ggagcaagag cctgagcccc agcctgctgg gctatcagca    2520
gccggccctc atggccgccc cgctgtccct tgcggacgct caccgctctg tgctggtgca    2580
cgccggctcc cagggccaga gctcagccct gctccacccc tctccgacca accagcaggc    2640
ctcgcctgtg atccactact cacccaccaa ccagcagctg cgctgcggaa gccaccagga    2700
gttccagcac atcatgtact gcgagaattt cgcaccaggc accaccagac ctggcccgcc    2760
cccggtcagt caaggtcaga ggctgagccc gggttcctac cccacagtca ttcagcagca    2820
gaatgccacg agccaaagag ccgccaaaaa cggacccccg gtcagtgacc aaaaggaagt    2880
attacctgcg ggggtgacca ttaaacagga gcagaacttg gaccagacct acttggatga    2940
tgttaatgaa attatcagga aggagttttc aggacctcct gccagaaatc agacgtaaaa    3000
gaagccatta tagcaagaca ccttctgtat ctgaccctc ggagccctcc acagcccctc    3060
accttctgtc tcctttcatg ttcatctccc agcccggagt ccacacgcgg atcaatgtat    3120
gggcactaag cggactctca cttaaggagc tcgccacctc cctcta                  3166
```

<210> SEQ ID NO 5
<211> LENGTH: 925
<212> TYPE: PRT
<213> ORGANISM: Homo sapiens

<400> SEQUENCE: 5

```
Met Asn Ala Pro Glu Arg Gln Pro Gln Pro Asp Gly Gly Asp Ala Pro
1               5                   10                  15

Gly His Glu Pro Gly Gly Ser Pro Gln Asp Glu Leu Asp Phe Ser Ile
            20                  25                  30

Leu Phe Asp Tyr Glu Tyr Leu Asn Pro Asn Glu Glu Pro Asn Ala
        35                  40                  45

His Lys Val Ala Ser Pro Pro Ser Gly Pro Ala Tyr Pro Asp Asp Val
    50                  55                  60

Leu Asp Tyr Gly Leu Lys Pro Tyr Ser Pro Leu Ala Ser Leu Ser Gly
65                  70                  75                  80

Glu Pro Pro Gly Arg Phe Gly Glu Pro Asp Arg Val Gly Pro Gln Lys
                85                  90                  95

Phe Leu Ser Ala Ala Lys Pro Ala Gly Ala Ser Gly Leu Ser Pro Arg
            100                 105                 110

Ile Glu Ile Thr Pro Ser His Glu Leu Ile Gln Ala Val Gly Pro Leu
        115                 120                 125

Arg Met Arg Asp Ala Gly Leu Leu Val Glu Gln Pro Pro Leu Ala Gly
    130                 135                 140

Val Ala Ala Ser Pro Arg Phe Thr Leu Pro Val Pro Gly Phe Glu Gly
145                 150                 155                 160
```

```
Tyr Arg Glu Pro Leu Cys Leu Ser Pro Ala Ser Ser Gly Ser Ser Ala
                165                 170                 175

Ser Phe Ile Ser Asp Thr Phe Ser Pro Tyr Thr Ser Pro Cys Val Ser
            180                 185                 190

Pro Asn Asn Gly Gly Pro Asp Asp Leu Cys Pro Gln Phe Gln Asn Ile
        195                 200                 205

Pro Ala His Tyr Ser Pro Arg Thr Ser Pro Ile Met Ser Pro Arg Thr
    210                 215                 220

Ser Leu Ala Glu Asp Ser Cys Leu Gly Arg His Ser Pro Val Pro Arg
225                 230                 235                 240

Pro Ala Ser Arg Ser Ser Pro Gly Ala Lys Arg His Ser Cys
                245                 250                 255

Ala Glu Ala Leu Val Ala Leu Pro Pro Gly Ala Ser Pro Gln Arg Ser
            260                 265                 270

Arg Ser Pro Ser Pro Gln Pro Ser Ser His Val Ala Pro Gln Asp His
        275                 280                 285

Gly Ser Pro Ala Gly Tyr Pro Pro Val Ala Gly Ser Ala Val Ile Met
    290                 295                 300

Asp Ala Leu Asn Ser Leu Ala Thr Asp Ser Pro Cys Gly Ile Pro Pro
305                 310                 315                 320

Lys Met Trp Lys Thr Ser Pro Asp Pro Ser Pro Val Ser Ala Ala Pro
                325                 330                 335

Ser Lys Ala Gly Leu Pro Arg His Ile Tyr Pro Ala Val Glu Phe Leu
            340                 345                 350

Gly Pro Cys Glu Gln Gly Glu Arg Arg Asn Ser Ala Pro Glu Ser Ile
        355                 360                 365

Leu Leu Val Pro Pro Thr Trp Pro Lys Pro Leu Val Pro Ala Ile Pro
    370                 375                 380

Ile Cys Ser Ile Pro Val Thr Ala Ser Leu Pro Pro Leu Glu Trp Pro
385                 390                 395                 400

Leu Ser Ser Gln Ser Gly Ser Tyr Glu Leu Arg Ile Glu Val Gln Pro
                405                 410                 415

Lys Pro His His Arg Ala His Tyr Glu Thr Glu Gly Ser Arg Gly Ala
            420                 425                 430

Val Lys Ala Pro Thr Gly Gly His Pro Val Val Gln Leu His Gly Tyr
        435                 440                 445

Met Glu Asn Lys Pro Leu Gly Leu Gln Ile Phe Ile Gly Thr Ala Asp
    450                 455                 460

Glu Arg Ile Leu Lys Pro His Ala Phe Tyr Gln Val His Arg Ile Thr
465                 470                 475                 480

Gly Lys Thr Val Thr Thr Thr Ser Tyr Glu Lys Ile Val Gly Asn Thr
                485                 490                 495

Lys Val Leu Glu Ile Pro Leu Glu Pro Lys Asn Asn Met Arg Ala Thr
            500                 505                 510

Ile Asp Cys Ala Gly Ile Leu Lys Leu Arg Asn Ala Asp Ile Glu Leu
        515                 520                 525

Arg Lys Gly Glu Thr Asp Ile Gly Arg Lys Asn Thr Arg Val Arg Leu
    530                 535                 540

Val Phe Arg Val His Ile Pro Glu Ser Ser Gly Arg Ile Val Ser Leu
545                 550                 555                 560

Gln Thr Ala Ser Asn Pro Ile Glu Cys Ser Gln Arg Ser Ala His Glu
                565                 570                 575

Leu Pro Met Val Glu Arg Gln Asp Thr Asp Ser Cys Leu Val Tyr Gly
            580                 585                 590
```

```
Gly Gln Gln Met Ile Leu Thr Gly Gln Asn Phe Thr Ser Glu Ser Lys
        595                 600                 605

Val Val Phe Thr Glu Lys Thr Thr Asp Gly Gln Gln Ile Trp Glu Met
610                 615                 620

Glu Ala Thr Val Asp Lys Asp Lys Ser Gln Pro Asn Met Leu Phe Val
625                 630                 635                 640

Glu Ile Pro Glu Tyr Arg Asn Lys His Ile Arg Thr Pro Val Lys Val
                645                 650                 655

Asn Phe Tyr Val Ile Asn Gly Lys Arg Lys Arg Ser Gln Pro Gln His
                660                 665                 670

Phe Thr Tyr His Pro Val Pro Ala Ile Lys Thr Glu Pro Thr Asp Glu
                675                 680                 685

Tyr Asp Pro Thr Leu Ile Cys Ser Pro Thr His Gly Gly Leu Gly Ser
                690                 695                 700

Gln Pro Tyr Tyr Pro Gln His Pro Met Val Ala Glu Ser Pro Ser Cys
705                 710                 715                 720

Leu Val Ala Thr Met Ala Pro Cys Gln Gln Phe Arg Thr Gly Leu Ser
                725                 730                 735

Ser Pro Asp Ala Arg Tyr Gln Gln Gln Asn Pro Ala Ala Val Leu Tyr
                740                 745                 750

Gln Arg Ser Lys Ser Leu Ser Pro Ser Leu Leu Gly Tyr Gln Gln Pro
                755                 760                 765

Ala Leu Met Ala Ala Pro Leu Ser Leu Ala Asp Ala His Arg Ser Val
                770                 775                 780

Leu Val His Ala Gly Ser Gln Gly Gln Ser Ser Ala Leu Leu His Pro
785                 790                 795                 800

Ser Pro Thr Asn Gln Gln Ala Ser Pro Val Ile His Tyr Ser Pro Thr
                805                 810                 815

Asn Gln Gln Leu Arg Cys Gly Ser His Gln Glu Phe Gln His Ile Met
                820                 825                 830

Tyr Cys Glu Asn Phe Ala Pro Gly Thr Thr Arg Pro Gly Pro Pro
                835                 840                 845

Val Ser Gln Gly Gln Arg Leu Ser Pro Gly Ser Tyr Pro Thr Val Ile
850                 855                 860

Gln Gln Gln Asn Ala Thr Ser Gln Arg Ala Ala Lys Asn Gly Pro Pro
865                 870                 875                 880

Val Ser Asp Gln Lys Glu Val Leu Pro Ala Gly Val Thr Ile Lys Gln
                885                 890                 895

Glu Gln Asn Leu Asp Gln Thr Tyr Leu Asp Asp Val Asn Glu Ile Ile
                900                 905                 910

Arg Lys Glu Phe Ser Gly Pro Pro Ala Arg Asn Gln Thr
                915                 920                 925

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttggtctgt gggctgcat                                                    19

<210> SEQ ID NO 7
<211> LENGTH: 21
```

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcctgggaag ataggcctgt t                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttggtatga ccccgctgaa                                                20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctttcttcca actgggcatc a                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctcgttgga ccaaaacaca                                                20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgatggcat cttccacaa                                                 19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcctgatgtt ggtggcttca                                                20

<210> SEQ ID NO 13
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
cacactctgt cttggcaaat cc                                          22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagggagaag cagacatcaa ca                                          22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcatgggcaa ggattccat                                              19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcctcaagtg ggaccatcat                                             20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcgcggcaa gtcttcaga                                              19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcacctgatt cttgcgtgct a                                           21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 19
cagatggacc ccatgtttgc                                              20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcaactcgga cctggtcata a                                            21

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctggtataag gtggtctcgt tgatt                                        25

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acccggcagg acctgtgt                                                18

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccagttcatg agcagcagtg a                                            21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gctgctggta gcatcgttac tg                                           22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
gagtgtagcg cgcatgctt                                              19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgggatctac cgctgtgaag t                                           21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcgtccttg tcaccatagc aa                                          22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgagatcccc ttcggagagt                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgagccgcga agttcttttc                                             20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcttaagcgt cgtgcaagat ttc                                         23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```
cttgggacac agttcacttc ca                                          22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttatgctgaa cggtaccaaa cg                                          22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggcgtatgg gatgaagtat t                                           21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cacaaaaccc ctcgatagaa gtg                                         23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cctgtgatca ggaactgctg aa                                          22

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acacctccca agtcctttat gaat                                        24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cccgtcaata tcagctactt gct                                         23

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctggaggct gctgaacga                                                19

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tccgttcttc accgacttcc t                                             21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcttccttgt gcaagtgtct ga                                            22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcaaaaggtg gcatttcaca gt                                            22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cggatgcgac aaaaatcact t                                             21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cccttctcct gtgacctcgt t                                             21

<210> SEQ ID NO 44

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcggaggctt aattacacat gttc                                          24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgccattgca caactctttt ct                                            22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaccagctg gacaacatac tg                                            22

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
accaggtaaa actggatcat ttcc                                          24

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgaggagct gagcaacatc ac                                            22

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcggccaggt ccacact                                                  17

<210> SEQ ID NO 50
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 50
tctgtgtctc tgatgctgtt gct                                            23

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcgctgctgc cttcactgt                                                 19

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtcgaagtat ctggaagagc tcaat                                          25

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctcttgcgtc aacttcaagg aa                                             22

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgaagtcgg ccaaagttgt c                                              21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agggatgaga agttcccaaa tg                                             22

<210> SEQ ID NO 56
<211> LENGTH: 23
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 56
ggcttgtcac tcgaattttg aga                                               23

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtgcagctcc acggctacat                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcggcttaag gatcctctca                                                   20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgtttggcct gaagcagaga                                                   20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcctgcggta cagatctagc a                                                 21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagagccatg ctgtgttcca                                                   20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
accgcattcc gattttcatc                                                      20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgggctggaa tgattggatt                                                      20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cagtccccat ggcagtagaa g                                                    21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttcttcaagg caagcgaggt a                                                    21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcggttttga tttttccgtt t                                                    21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gctgaagtcc gctccactct                                                      20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cccatcctct tcgtcgtcat                                         20

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgacgccga catggtcat                                          19

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtggtatcg agggtggaag a                                       21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tggtctgctt ggacgacaag                                         20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gctggccctg aagaaggtta                                         20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cagccactgc cagaagactt c                                       21

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccttgggtgc aatgatcca                                          19

```
<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tggctgaact gcggttgtac                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ttacggtcca cgccatcata                                              20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgcgcctaga gagcatcaag t                                            21

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tacctcccgg ctgatgttg                                               19

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgggcgtgtg gacacaa                                                 17

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gctctggcct tgagttgctt                                              20
```

```
<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgcgctgca gcagaaag                                                    18

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gtcgtcccag cctaactcct t                                                21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aacagcagcg tgaagttgga                                                  20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggtcatcttg ccctttgtca a                                                21

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acgattggag cgaaaatggt                                                  20

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aacctctggg aggccttact g                                                21

<210> SEQ ID NO 87
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gagctggtgg atgctcttca g                                              21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gcctgtgggc ttgttgaagt                                                20

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccgaagcgga ctactatgct aaa                                            23

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gttttctcat agatggcgtt gttg                                           24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ctgtaccttc gtgccgtcta ataa                                           24

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgccatcaat acctgcaaat ct                                             22

<210> SEQ ID NO 93
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 93
cagtggagaa aaatggaacc aat                                              23
```

PREVENTION AND TREATMENT OF OSTEOARTHRITIS

CROSS-REFERENCE TO RELATED APPLICATIONS

The application is a divisional application of U.S. patent application Ser. No. 12/407,536 filed 19 Mar. 2012 and entitled "PREVENTION AND TREATMENT OF OSTEOARTHRITIS." U.S. patent application Ser. No. 12/407,536 claims the benefit of U.S. Provisional Application Ser. No. 61/038,591 filed 21 Mar. 2008 and entitled "PREVENTION AND TREATMENT OF OSTEOARTHRITIS." The above listed applications are incorporated herein by reference in their entireties.

BACKGROUND OF THE INVENTION

1. The Field of the Invention

The present invention relates to early prediction of the onset of osteoarthritis, early diagnosis of osteoarthritis, early treatment of osteoarthritis, and screening of drug candidates useful for treating osteoarthritis.

2. The Relevant Technology

Osteoarthritis ("OA") is the most common joint disease in middle-aged and older people. OA is characterized by joint pain and dysfunction caused by joint degeneration, including progressive loss of articular cartilage, osteophyte formation, and sclerosis of subchondral bone. Joint contractures, periarticular muscle atrophy, and limb deformity occur in advanced stages of the disease and often lead to disability and sometimes the need for joint replacement. Currently, persistent joint pain and stiffness and radiographic evidence for joint space narrowing, osteophytes, and in some cases, increased subchondral bone density and cysts are used to establish the diagnosis of OA.

OA often develops in the absence of a specific known cause of joint degeneration, a condition referred to as either primary or idiopathic OA. Less frequently, OA develops as a result of joint degeneration caused by injuries or a variety of hereditary, developmental, metabolic, and neurological disorders, which is referred to as secondary OA. Primary OA rarely occurs in people younger than 40 years old. Secondary OA may occur in younger adults. Although a number of risk factors have been proposed to be involved in the pathogenesis of OA, the root causes of primary OA remain unclear. Current treatments for OA, including weight reduction, pain amelioration, and joint replacement, are largely palliative. Efforts to develop methods for the surgical or biological repair of damaged articular cartilage face major obstacles due to the limited intrinsic repair capacity of the tissue. Therefore, the development of novel therapeutic strategies is highly likely to depend upon the identification of the molecular and cellular mechanisms involved in the initiation and progression of OA.

BRIEF SUMMARY OF THE INVENTION

The present invention is directed to the pathogenesis of osteoarthritis in the joints of a subject (e.g., a human or an animal such as a mouse). The present invention relates to the transcription factor Nfat1, which has now been discovered to be involved in the pathogenesis of OA. The present invention includes methods of treating OA, methods of diagnosis and early prediction of the onset of OA, and methods for screening drug candidates that may be useful for treatment of OA.

In one embodiment, a method of treating, inhibiting, and/or preventing osteoarthritis is disclosed. The method includes (1) providing a subject having low Nfat1, and (2) increasing Nfat1 in the subject.

In one embodiment, increasing Nfat1 in the subject can include stimulating synthesis of Nfat1 in the subject. For example, stimulating synthesis of Nfat1 can include administering to the subject a bioactive substance that increases Nfat1 transcriptional activity and/or increases synthesis of Nfat1 protein.

In one embodiment, increasing Nfat1 in the subject can include administering Nfat1 to the subject. For example, administering Nfat1 to the subject can include administering purified Nfat1 to the subject and/or administering to the subject a nucleic acid encoding Nfat1 that is capable of directing synthesis of Nfat1.

In one embodiment, the method of treating, inhibiting, and/or preventing osteoarthritis can include measuring Nfat1 in the subject and/or measuring downstream effectors of Nfat1, and comparing the subject's Nfat1 level and/or the downstream effectors of Nfat1 to a control subject's Nfat1 activity level and/or the control subject's activity of downstream effectors of Nfat1. That is, the subject's Nfat1 level can be compared to a control or standard subject having normal or "wild-type" Nfat1 levels.

In one embodiment, Nfat1 and/or the downstream effectors of Nfat1 can modulate or include at least one of matrix metalloproteinase 1a (Mmp1a), matrix metalloproteinase 13 (Mmp13), Adamts5 (i.e., a disintegrin and metalloproteinase with a thrombospondin type 1 motif, member 5), tissue inhibitor of metalloproteinase-1 (Timp1), aggrecan, a collagen protein, β-catenin, interleukin-1β (IL-1β), interleukin-6 (IL-6), interleukin-17α (IL-17α), and the like.

In one embodiment, a method of diagnosing osteoarthritis and/or predicting susceptibility to osteoarthritis in a subject is disclosed. The method can include (1) measuring the subject's Nfat1 level, and (2) comparing the subject's Nfat1 level to a control subject's Nfat1 level, wherein low Nfat1 is diagnostic of or predictive of susceptibility to osteoarthritis.

In one embodiment a method of diagnosing osteoarthritis in a subject can also include providing a blood or tissue sample from the subject, and measuring the Nfat1 level in the blood or tissue sample. For example, the tissue sample can include articular cartilage cells.

In one embodiment, the measuring of Nfat1 can further include measuring type II collagen production by articular cartilage cells in the subject. In one embodiment, the measuring of Nfat1 can further include measuring aggrecan production by articular cartilage cells in the subject.

In one embodiment, a method of diagnosing osteoarthritis in a subject can also include probing the subject's genome for sequence variations in Nfat1.

In one embodiment, a method of diagnosing osteoarthritis in a subject can also include determining whether the subject has degenerative articular cartilage disease, a method of diagnosing osteoarthritis in a subject can further include measuring articular cartilage degeneration, a method of diagnosing osteoarthritis in a subject can further include measuring downstream effectors of Nfat1. Moreover, a method of diagnosing osteoarthritis in a subject can include administering at least one bioactive substance to the subject and determining whether the bioactive substance increases activity of Nfat1 and/or affects the downstream effectors of Nfat1

In one embodiment, a method of screening drug candidates useful for treating osteoarthritis is disclosed. The method can use a first screen that can include (1) providing cultured cells from a subject organism that are Nfat1 negative and/or Nfat1 deficient, (2) exposing the cells to at least one drug candidate, and (3) probing for, increased Nfat1 transcription, increased Nfat1 protein expression, increased Nfat1 function, and/or evaluating the activity or production of downstream effectors of Nfat1. The subject organism can be any organism described herein or otherwise known. For example, the cells can come from an Nfat1 knockout (i.e., Nfat1$^{-/-}$) or the cells can come from an organism engineered to overexpress Nfat1 (i.e., CA-Nfat1). In one example, the cells from the subject organism can be articular cartilage cells and/or a cartilaginous cell line.

In one embodiment, a method of screening drug candidates useful for treating osteoarthritis can include measuring production of type II collagen in the cells from the subject organism. The method of screening drug candidates useful for treating osteoarthritis can also include measuring production of aggrecan in the cells from the subject organism.

In one embodiment, a method of screening drug candidates useful for treating osteoarthritis can include a second screen. The second screen can include (1) exposing the subject organism to at least one drug candidate identified in the first screen, and (2) probing the organism for increased and/or decreased Nfat1 activity, altered activity and/or production of the downstream effectors of Nfat1, and/or probing for an improved osteoarthritis phenotype relative to a control organism not receiving the at least one drug candidate.

Many Nfat-type transcription factors are known (e.g., Nfat1, Nfat2, Nfat3, and Nfat4) and there is some redundancy of function amongst the known Nfat-type transcription factors. As such, in another embodiment, the present invention can include a method treating, inhibiting, and/or preventing osteoarthritis that includes (1) providing a subject having low activity of at least one Nfat-type transcription factor, and (2) increasing the activity of the at least one Nfat-type transcription factor in the subject.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1A:
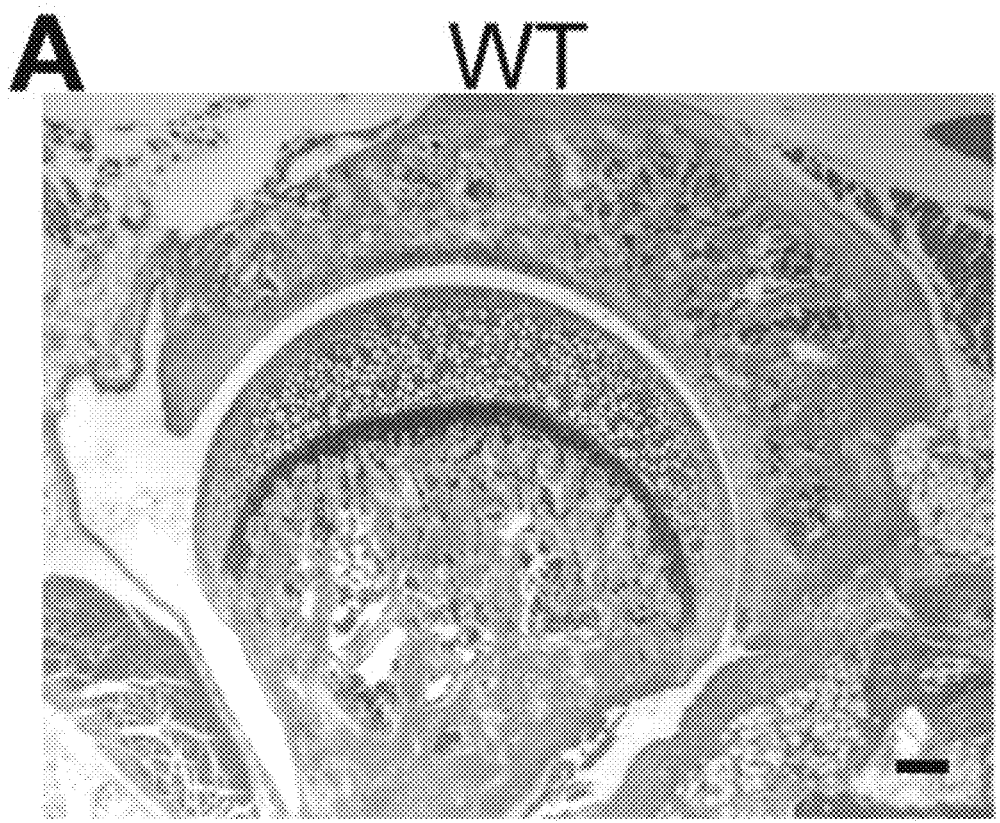
FIG. 1A illustrates a 2-month-old female wild-type (WT) mouse hip joint with safranin-O staining (i.e., darker staining) showing normal joint structure and articular surface.

The present invention is directed to the pathogenesis of osteoarthritis in the joints of a subject (e.g., a human or an animal such as a mouse), as well as the diagnosis and treatment thereof. More particularly, the present invention relates to the transcription factor Nfat1, which has been discovered to be involved in the pathogenesis of OA. The present invention includes methods of treating OA, methods of diagnosis and early prediction of the onset of OA, and methods for screening drug candidates that may be useful for treatment of OA.

Age is the overriding risk factor for developing OA, and the prevalence of OA in all joints increases with age. The most longstanding theory is that OA develops because of continuous mechanical wear and tear. However, recreational running and lifelong joint use have not been shown to increase the risk of joint degeneration. In addition, mitotic and synthetic activities of articular chondrocytes decline with age as they become less responsive to anabolic cytokines and mechanical stimuli. Chondrocytes may undergo age-related telomere erosion and increased expression of the senescence marker β-galactosidase, suggesting that cell senescence might be responsible for the age-related loss of chondrocyte function. However, key factors that elicit premature chondrocyte senescence have not been identified.

The risk of progressive joint degeneration may increase due to direct and indirect joint impact loading; meniscal, ligament, and joint capsule tears; joint dislocations; and intraarticular fractures. The available evidence indicates that posttraumatic joint incongruity, instability, and malalignment may compromise repair of the articular surface and increase the risk of progressive degeneration of residual normal articular cartilage. The risk of OA after joint injuries increases with age, suggesting that biological factors may be involved in the development of posttraumatic OA.

Studies have also demonstrated the heritability OA at several joint sites, suggesting that OA has a genetic component. Other genetic epidemiologic studies have revealed evidence for the nature of OA transmittance from parents to offspring and prevalence of the disease between pairs of relatives, particularly siblings. Genetic risk associated with knee OA suggests that the whole joint might be involved in the disease development process. Gene expression is an alternative systemic approach to identifying OA-susceptibility genes. Several genes were reported to be associated with OA prevalence or progression. However, these studies are primarily based on small cohort sizes, which may lead to false positives and false negatives.

In most human joints, the incidence of OA is greater in women than in men. Several studies suggested that female sex hormones, particularly estrogen and estrogen receptor-α gene (ESR1), might play a role in OA. However, clinical and laboratory observations on the effects of sex hormones on the pathophysiology of OA are controversial. With the current level of evidence, hormone replacement therapy (HRT) cannot be recommended as a first-line treatment against the progression of OA.

Other proposed risk factors for OA include obesity, greater bone density, joint laxity, abnormal mechanical loading, and long-term, excessive, repetitive joint use.

Presently, there are no effective methods capable of preventing the initiation of primary OA or reversing joint degeneration during the progression of the disease. While OA-like changes can be induced in animal models by mutating genes encoding cartilage structural proteins, growth factor receptors, or cartilage matrix-degrading enzymes, these models fail to elucidate which intracellular factors regulate the function of articular cartilage cells. Moreover, these studies have failed to provide useful molecular factors for either diagnosing OA or providing targets for treatment of OA.

Surprisingly and unexpectedly, it has recently been discovered that adult mice lacking transcription factor Nfat1 recapitulate most of the characteristics of human primary OA, including the loss of articular cartilage, chondrophyte/osteophyte formation, thickening of subchondral bone, and eventual joint destruction in older animals. Mechanistic analyses demonstrate that the synthesis of major matrix components of articular cartilage, such as aggrecan and type-II collagen, is significantly decreased during the initiation stage of OA in adult Nfat1 null mice. Mechanistic analyses also demonstrate that the synthesis of catabolic factors such as matrix metalloproteinase and proinflammatory cytokines is up-regulated in Nfat1 null mice. Furthermore, knockdown of Nfat1 gene by Nfat1 siRNA significantly decreases the production of aggrecan and type-II collagen and up-regulates the synthesis of catabolic factors in wild type mouse articular chondrocytes and in the insulin-treated ATDC5 chondrogenic cell line.

Based on these observations, it is believed that Nfat1 is normally responsible for up-regulating synthesis of aggrecan and collagen proteins while simultaneously down-regulating synthesis of certain catabolic proteases and proinflammatory cytokines. As such, this invention has revealed for the first time that the transcription factor Nfat1 regulates the functions of certain molecular factors critical for maintaining and balancing the anabolic and catabolic activities of differentiated articular cartilage cells. Moreover, it has been revealed that loss or deficiency of Nfat1 activity can cause dysfunction of articular cartilage cells, which significantly decreases the rate of synthesis of major cartilage matrix proteins and increases the synthesis of catabolic proteinases and proinflammatory cytokines in adult articular cartilage. It is demonstrated herein that the imbalance of catabolic and anabolic events in favor of collagen and aggrecan catabolism in Nfat1 deficient animals (e.g., Nfat1$^{-/-}$ mice) leads to degradation of articular cartilage and destruction of joint structure, which leads to the development of OA. These observations indicate that Nfat1 is critical for balancing anabolic and catabolic activities in joints. The observation that a single transcription factor can balance anabolic and catabolic activities of adult articular chondrocytes and play a role in the pathogenesis of OA is surprising and unexpected.

It is also revealed for the first time herein that Nfat1 treatment can rescue the dysfunction of articular cartilage cells. For instance, forced expression of Nfat1 (i.e., Nfat1 overexpression) in Nfat1$^{-/-}$ articular cartilage cells and/or in Nfat1 deficient mice can significantly increase the synthesis of major cartilage matrix genes/proteins in adult Nfat1 deficient articular cartilage cells while down regulating activity of matrix degrading proteinases and proinflammatory cytokines. The observation that overexpression of Nfat1 in Nfat1 null articular cartilage cells can "rescue" the OA-like cellular activities and restore normal function of articular cartilage cells is surprising and unexpected.

Based on these observations, it is proposed that Nfat1 deficiency causes OA due to an imbalance between catabolic and anabolic activities of adult articular chondrocytes, leading to articular cartilage degradation and failed repair activities in and around articular cartilage. As such, it is believed that Nfat1 and/or the downstream effectors of Nfat1 can be targeted for prevention and/or treatment of OA. These observations also suggest that susceptibility to OA can be predicted based on an individual's Nfat1 activity level and/or Nfat1 deficiency is an observable risk factor for the development of OA. Moreover, Nfat1 deficient cells (e.g., Nfat1$^{-/-}$ cells) and/or Nfat1 deficient organisms can be used for screening drug candidates for treatment of OA by looking for bioactive substances that increase Nfat1 activity and/or the activity of Nfat1's downstream effectors.

II. A Method of Treating, Inhibiting, or Preventing Osteoarthritis

Results are presented herein showing that Nfat1 deficiency can lead to OA. Moreover, results are presented herein showing that the OA phenotype associated with Nfat1 deficiency (e.g., Nfat1$^{-/-}$) can be rescued by forced expression of Nfat1 in articular cartilages cells and/or Nfat1 deficient organisms. It is therefore believed that Nfat1 and/or the downstream effectors of Nfat1 can be targeted for treating osteoarthritis. As such, a method of treating osteoarthritis is disclosed in one embodiment of the present invention. In one embodiment, a method of treating, inhibiting, or preventing osteoarthritis can include (1) providing a subject having low Nfat1 activity, and (2) increasing Nfat1 in the subject.

In one embodiment, a subject having low Nfat1 activity can be identified by measuring Nfat1 activity in the subject and/or measuring activity of downstream effectors of Nfat1, and comparing the subject's Nfat1 activity level and/or the activity of downstream effectors of Nfat1 to a wild-type control subject's Nfat1 activity level and/or the wild-type control subject's activity of downstream effectors of Nfat1. As used herein, a "wild-type control subject" can be a subject having normal Nfat1 activity and morphologically normal joint structure showing no signs of OA or degeneration of articular cartilage.

Suitable examples of a subject having low Nfat1 activity can include, but is not limited to, an Nfat1 knockout (i.e., Nfat1$^{-/-}$), a partial Nfat1 knockout (i.e., Nfat1$^{+/-}$), an Nfat1 knockdown, a subject having Nfat1 expression levels reduced by at least 50% relative to wild-type, a subject having Nfat1 expression levels reduced by at least 75% relative to wild-type, a subject having Nfat1 expression levels reduced by at least 90% relative to wild-type, a subject having Nfat1 expression levels reduced by at least 99% relative to wild-type, an individual having at least one Nfat1 sequence variation that reduces the activity of Nfat1, an individuals having familial-linked OA (i.e., genetically-linked OA), or an individual having genetically-linked degenerative articular cartilage disease.

In one embodiment, increasing Nfat1 in the subject can include stimulating synthesis of Nfat1 in the subject. For example, stimulating synthesis of Nfat1 can include administering to the subject a bioactive substance that increases Nfat1 transcription and/or increases synthesis of Nfat1 protein.

At present, several bioactive substances are known to inhibit or activate Nfat1. For example, the immunosuppressive drugs cyclosporin A and tacrolimus (FK506) can serve as general inhibitors Nfat-type transcription factors since they block calcineurin activity and nuclear translocation of Nfat-type transcription factors.

In contrast, ionomycin (a calcium ionophore) and polycystin-1 (a plasma membrane protein) can act as activators of Nfat-type transcription factors since they can trigger a sustained elevation of intracellular $Ca^{2+}$ and activate calcineurin. LiCl (lithium chloride) can act as an enhancer of Nfat-type transcription factors since it blocks GSK-3β-mediated rephosphorylation of NFAT and stabilizes NFAT transcriptional activity in the nucleus.

In one embodiment, increasing Nfat1 in the subject can include administering Nfat1 to the subject. In one embodiment, administering Nfat1 to the subject can include administering purified Nfat1 to the subject. For instance, Nfat1 could be overexpressed in cultured animal, yeast, and/or bacterial cells, purified, and directly injected into the blood and/or affected joints of the subject with an appropriate transmembrane agent(s) to drive it into the cytoplasm of target cells.

In addition, Nfat1 activity can be increased in the subject by administering to the subject a nucleic acid encoding Nfat1 that is capable of directing synthesis of Nfat1. For instance, a lentiviral construct for stable expression of constitutively active Nfat1 was generated using a pCDH-EF1-MCS-T2A-copGFP vector (System Biosciences) using the mouse Nfat1 cDNA sequence. Lentiviral vectors are known to be able to infect a wide range of eukaryotic cell types. And lentiviral vectors can lead to stable expression in host cells because the vectors typically direct the integration of the vector sequence into the host cell's genome.

Figure 4A:
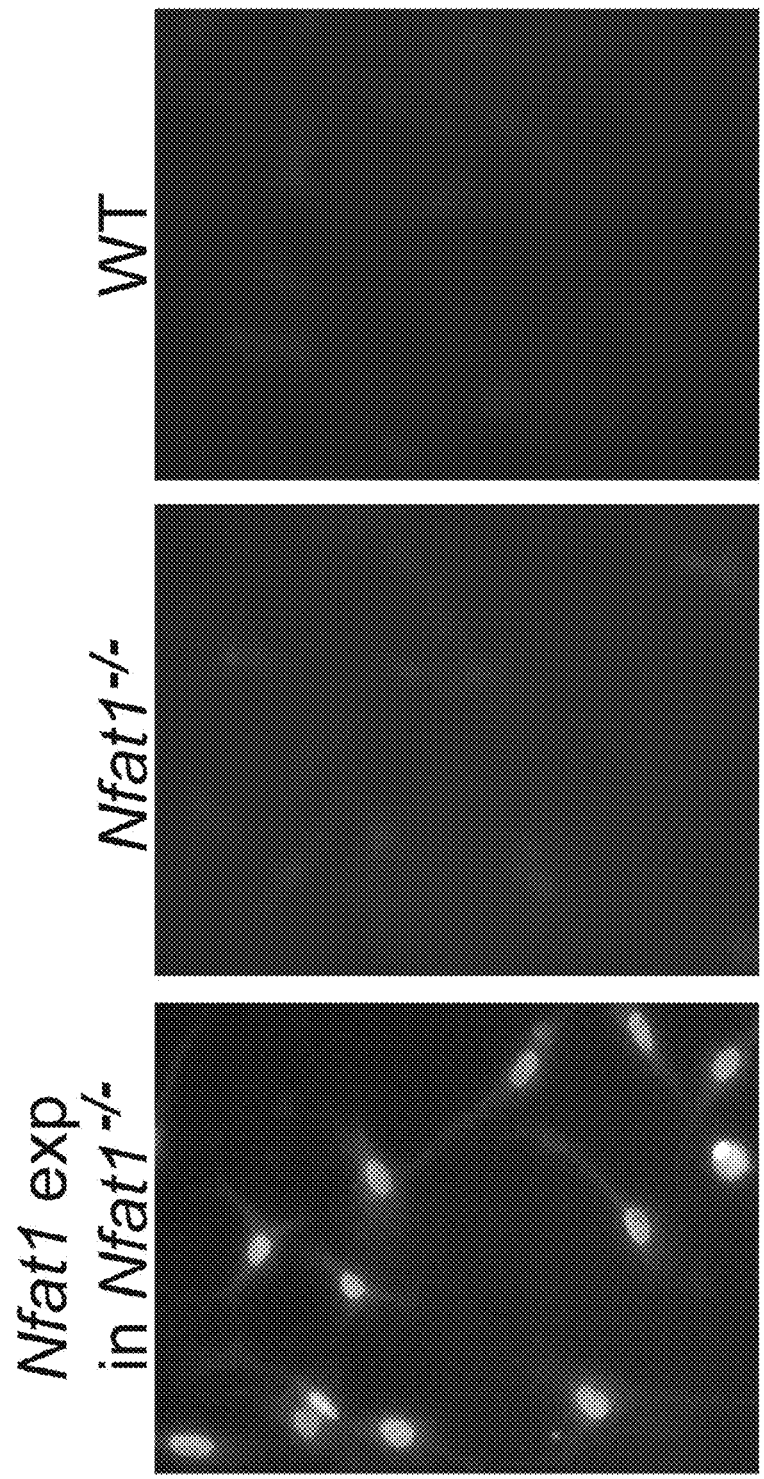
FIG. 4A illustrates immunofluorescence using an antibody against hemagglutinin (HA) tags, which shows positive expression of Nfat1 protein in the nuclei of Nfat$^{-/-}$ articular chondrocytes after transfection of Nfat1 plasmid with HA tags (Nfat1 exp in Nfat1$^{-/-}$), but not in control Nfat1$^{-/-}$ or WT articular chondrocytes in which HA tags are not present.
Figure 4B:
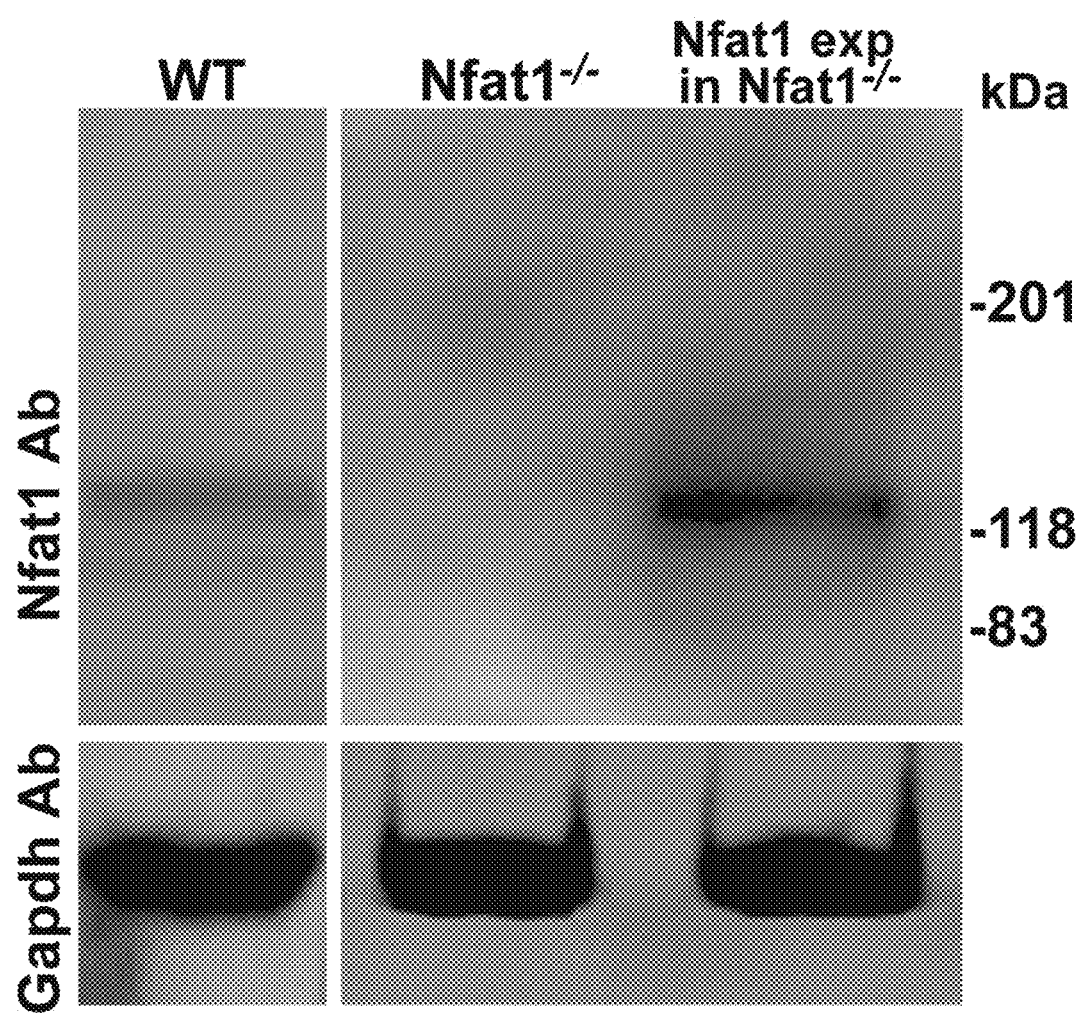
FIG. 4B illustrates a Western-blot comparing Nfat1 expression in WT, Nfat1$^{-/-}$, and forced expression of Nfat1 in Nfat1$^{-/-}$ cells.
Figure 4C:
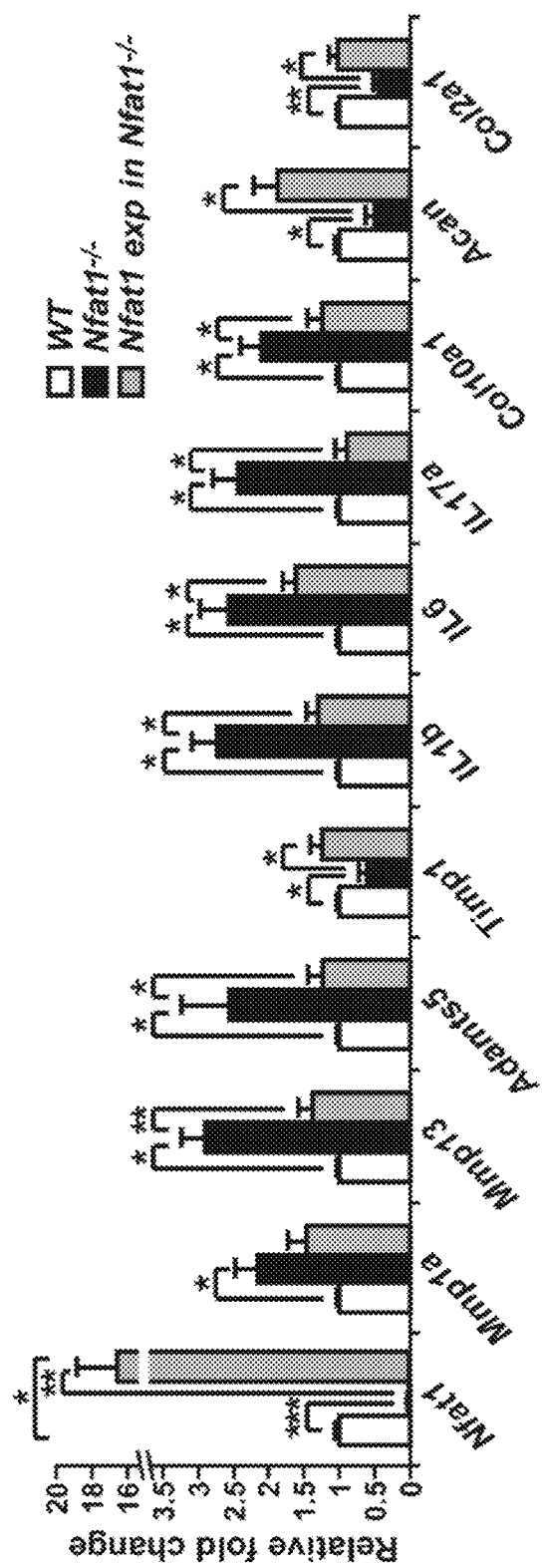
FIG. 4C shows that forced expression of Nfat1 rescues abnormal activities of 3-month-old Nfat1$^{-/-}$ articular chondrocytes.

Results presented herein demonstrate that forced expression of Nfat1 using lentiviral vectors in cultured 3-month old primary Nfat1$^{-/-}$ articular chondrocytes partially or completely rescued the abnormal catabolic and anabolic activities of Nfat1$^{-/-}$ articular chondrocytes (See, e.g., FIGS. 4A-4C).

A suitable treatment for OA can target Nfat1 and/or the downstream effectors of Nfat1. In one embodiment, Nfat1 and/or the downstream effectors of Nfat1 can affect or include at least one of matrix metalloproteinase 1a (Mmp1a), matrix metalloproteinase 13 (Mmp13), Adamts5 (i.e., a disintegrin and metalloproteinase with a thrombospondin type 1 motif, member 5), tissue inhibitor of metalloproteinase-1 (Timp1), aggrecan, a collagen protein, β-catenin, interleukin-1β (IL-1β), interleukin-6 (IL-6), interleukin-17α (IL-17α), and the like.

Many Nfat-type transcription factors are known (e.g., Nfat1, Nfat2, Nfat3, and Nfat4) and there is some redundancy of function amongst the known Nfat-type transcription factors. As such, in another embodiment, the present invention can include a method treating, inhibiting, and/or preventing osteoarthritis that includes (1) providing a subject having low activity of at least one Nfat-type transcription factor, and (2) increasing the activity of the at least one Nfat-type transcription factor in the subject.

As used herein, the term "activity" describes the state of a protein or another bioactive molecule resulting from one or more of transcription, translation, expression, or function. As such, low activity of at least one Nfat-type transcription factor can result from low transcription of mRNA, low translation of mRNA, another process the results in low expression of the protein, or reduced function of the protein resulting from, for example, one or more mutations in the protein sequence. Activity can be increased by, for example, increasing or improving transcription, translation, expression, or function.

III. A Method of Diagnosing Primary Osteoarthritis and/or Predicting Susceptibility to Primary Osteoarthritis Results are presented herein showing that Nfat1 deficiency can lead to OA. Moreover, results are presented herein showing that the OA phenotype associated with Nfat1 deficiency (e.g., Nfat1$^{-/-}$) can be rescued by forced expression of Nfat1 in articular cartilages cells and/or Nfat1 deficient organisms. It is therefore believed that finding an Nfat1 deficiency in a subject can be used to determine the subject's risk of developing OA. In addition, finding an Nfat1 deficiency in a subject showing symptoms of OA can be used to determine the initial cause of OA. As such, a method of diagnosing the initial cause of primary osteoarthritis is disclosed in one embodiment of the present invention.

In one embodiment, a method of diagnosing primary osteoarthritis and/or predicting susceptibility to osteoarthritis in a subject can include (1) measuring the subject's Nfat1 activity level, and (2) comparing the subject's Nfat1 activity level to a wild-type control subject's Nfat1 activity level, comparing the subject's Nfat1 activity level to a wild-type control Nfat1 activity level, wherein low Nfat1 activity is diagnostic of or predictive of susceptibility to primary osteoarthritis.

It has been found that a subject's Nfat1 activity level in blood and tissue samples can be detected by using analytical techniques such as quantitative real-time PCR (i.e., qPCR) using primers specific to Nfat1 or Nfat1 isoforms. For example, age-related changes in expression levels of Nfat1 or Nfat1 isoforms have been determined by qPCR analysis in mouse blood and tissue samples. It was found that low levels of Nfat1 activity are predictive of the onset of osteoarthritis in Nfat1$^{-/-}$, NFAT$^{+/-}$, and older Nfat1 wild type mice. In one embodiment, the tissue sample can include articular cartilage cells.

Similar studies are underway in human subjects using blood and/or tissue samples. For example, articular cartilage samples can be harvested from human subjects with osteoarthritis undergoing joint replacement surgery. DNA can also be isolated for DNA sequencing studies from discarded human osteoarthritic articular cartilage and/or blood to detect whether a mutation in the Nfat1 DNA binding domain exists in human osteoarthritic articular cartilage and/or blood. Initial data show that expression of Nfat1 in human subjects is consistent with the mouse model. For instance, FIGS. 9A-9D illustrates that Nfat1 expression is lowered in human joint cartilage in subjects having OA as compared to subjects having normal cartilage.

Figure 10:
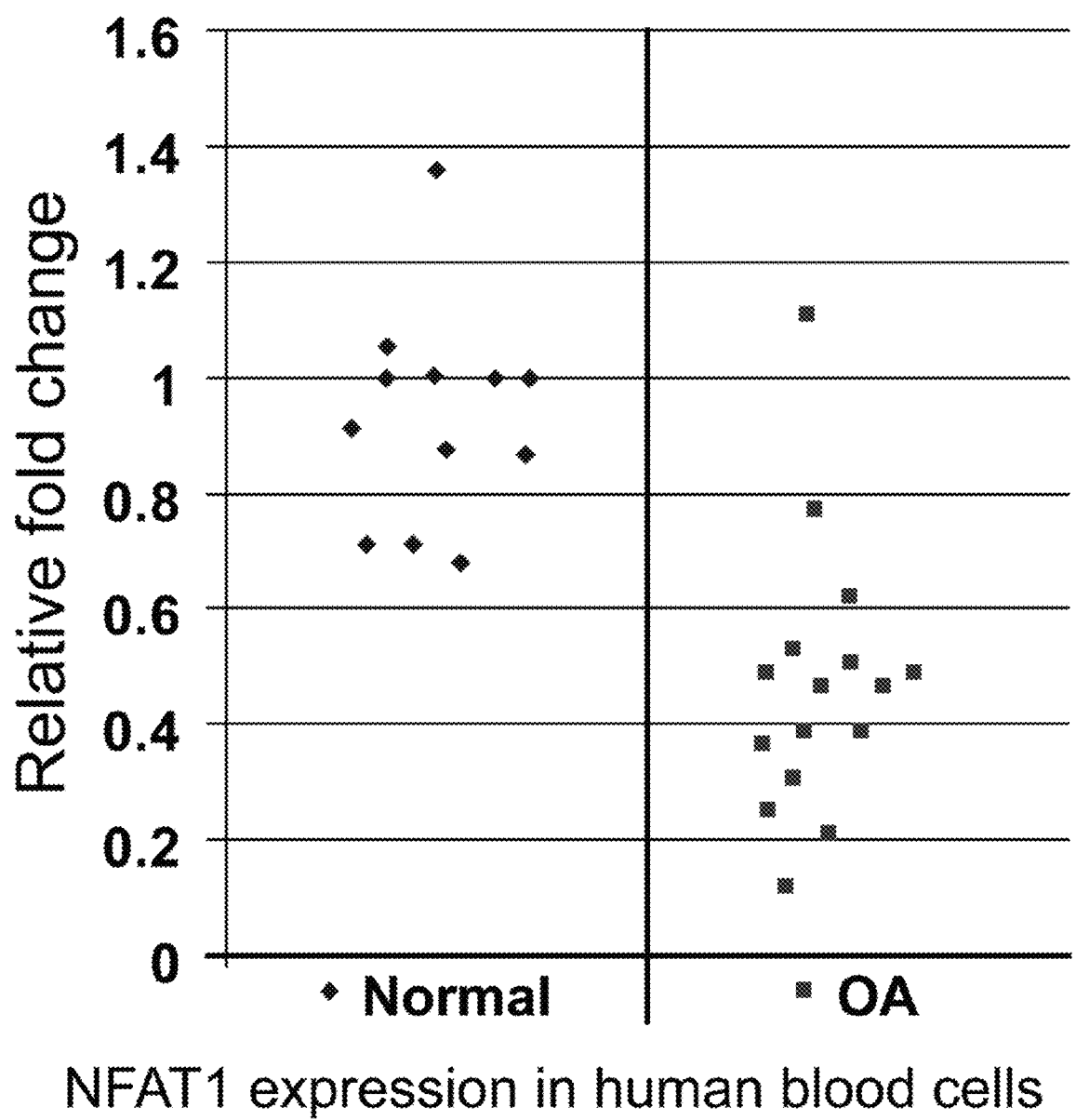
FIG. 10 illustrates qPCR analyses demonstrating that the expression levels of NFAT1 mRNA are decreased in peripheral blood cells in the majority of patients with OA (n=16, mean age=61) compared to a control group showing no clinical evidence of OA (n=12, mean age=53); each symbol represents an individual human subject.

In another example presented herein, FIG. 10 illustrates qPCR analyses demonstrating that the expression levels of NFAT1 mRNA are decreased in peripheral blood cells in the majority of patients with OA (n=16, mean age=61) compared to a control group showing no clinical evidence of OA (n=12, mean age=53). These results indicate that low levels of NFAT1 expression and/or activity in blood are predictive of the onset of osteoarthritis, at least in a subset (subgroup) of OA patients.

Clinically, blood testing is a simple and inexpensive method, which can be used for at least one of the following purposes:

Prevention of OA. Although a low level of NFAT1 expression and/or activity in blood cannot typically be used as a sole diagnostic criterion of OA, it should be considered a risk factor for the development of OA. This is because NFAT1 is a key factor for maintaining the function of adult articular cartilage cells and its deficiency may cause OA. Application of NFAT1 and/or an NFAT1 activator to the subject with NFAT1 deficiency may prevent the onset of OA.

Early diagnosis of OA. Although a low level of NFAT1 expression and/or activity in blood typically cannot be used as a sole diagnostic criterion of OA, it can be used in a method to screen for OA. For instance, a patient with a low level of NFAT1 expression and/or activity can be further examined by more specific non-invasive diagnostic approaches such as magnetic resonance imaging (MRI) to confirm whether such individual has early articular cartilage degeneration. An early diagnosis of NFAT1 deficiency-induced OA can be established if a patient (or a subject) has both NFAT1 deficiency and articular cartilage degeneration.

Early treatment of OA. Currently, there are no therapeutic strategies for early treatment of OA. This is generally because: a) there are no simple diagnostic methods such as blood testing available for early diagnosis of OA, and b) even though a patient is diagnosed as early OA, there is no effective treatment to stop or reverse the progression of OA since the root causes of primary OA are unknown. An early diagnosis of NFAT1 deficiency-induced OA will make early treatment of the disease possible.

As such, one embodiment of the present invention includes measuring a subject's Nfat1 activity level combined with measuring type II collagen production by articular cartilage cells in the subject. In another example, measuring a subject's Nfat1 activity level can include measuring aggrecan production by articular cartilage cells in the subject.

Other downstream effectors of Nfat1 that are affected by Nfat1 activity include, but are not limited to, matrix metalloproteinase 1a (Mmp1a), matrix metalloproteinase 13 (Mmp13), Adamts5 (i.e., a disintegrin and metalloproteinase with a thrombospondin type 1 motif, member 5), tissue inhibitor of metalloproteinase-1 (Timp1), a collagen protein other than collagen II, β-catenin, interleukin-1β (IL-1β), interleukin-6 (IL-6), interleukin-17α (IL-17α), and the like.

In one embodiment, a method of diagnosing primary osteoarthritis and/or predicting susceptibility to osteoarthritis in a subject can further include probing the subject's genome for sequence variations in Nfat1. Also, a method of diagnosing primary osteoarthritis in a subject can further include determining whether the subject has degenerative articular cartilage disease. One example of a suitable method for determining whether the subject has degenerative articular cartilage disease can include magnetic resonance imaging (MRI) of the joints. That is, the certainty of a diagnosis of OA is increased if an Nfat1 deficiency also correlates with the evidence of degenerative articular cartilage disease. Additionally, a method of diagnosing primary osteoarthritis in a subject can further include measuring articular cartilage degeneration. One example of a suitable method for determining whether the subject has articular cartilage degeneration disease can include MRI of the joints. Likewise, the certainty of a diagnosis of OA is increased if an Nfat1 deficiency also correlates with the evidence of articular cartilage degeneration. Moreover, a method of diagnosing primary osteoarthritis in a subject can further include administering at least one bioactive substance to the subject and determining whether the bioactive substance increases activity of Nfat1 and/or affects its downstream effectors.

IV. A Method of Screening Drug Candidates Useful for Treating Osteoarthritis As discussed previously, results are presented herein showing that Nfat1 deficiency can lead to OA and that the OA phenotype associated with Nfat1 deficiency (e.g., Nfat1$^{-/-}$) can be rescued by forced expression of Nfat1 in articular cartilages cells and/or Nfat1 deficient organisms. As such, it is believed that bioactive substances that are able to mimic the function of Nfat1, stimulate the activity of Nfat1, increase cellular levels of Nfat1, or rescue one or more phenotypes associated with Nfat1 deficiency may be good candidates for treating Nfat1 deficiency-mediated OA.

In one embodiment, a method of screening drug candidates useful for treating primary osteoarthritis is disclosed. Such a method can include a first screen using cultured Nfat1-deficient cells and a second screen in an Nfat1-deficient organism. Such a screen can be adapted for high-throughput screening to screen a large number of candidate compounds.

In one embodiment, a first screen for drug candidates useful for treating primary osteoarthritis can include (1) providing cultured cells form a subject organism that are Nfat1 negative and/or Nfat1 deficient, (2) exposing the cells to at least one drug candidate, and (3) probing for increased Nfat1 expression and/or Nfat1 transcriptional activity and/or evaluating the activity or production of downstream effectors of Nfat1.

In one embodiment, the subject organism can be selected from at least one of the following: an Nfat1 genetic knockout (e.g., an Nfat1$^{-/-}$ knockout mouse), a partial Nfat1 genetic knockout (e.g., an Nfat1$^{+/-}$ mouse carrying only one functional copy of Nfat1), an Nfat1 knockdown, a subject having Nfat1 expression levels reduced by at least 10% relative to wild-type, a subject having Nfat1 expression levels reduced by at least 20% relative to wild-type, a subject having Nfat1 expression levels reduced by at least 40% relative to wild-type, a subject having Nfat1 expression levels reduced by at least 50% relative to wild-type, a subject having Nfat1 expression levels reduced by at least 75% relative to wild-type, a subject having Nfat1 expression levels reduced by at least 90% relative to wild-type, a subject having Nfat1 expression levels reduced by at least 99% relative to wild-type, a subject having genetically-linked osteoarthritis, or a subject having genetically-linked degenerative articular cartilage disease. In one embodiment, the cells can come from an organism engineered to overexpress Nfat1.

In one embodiment, the cells from the subject organism can be articular cartilage cells that are cultured in a mammalian cell culture medium. In the case of harvesting articular cartilage from femoral heads for RNA isolation and primary cell culture, it is known that the early OA-like phenotypes first occurs in the femoral head and its surrounding tissues of Nfat1$^{-/-}$ mice and femoral head articular cartilage is thicker and more capable of being removed in comparison to other joints. Techniques have been developed for collecting articular cartilage from mouse femoral heads for RNA isolation and primary cell culture. The hip joints of Nfat1 deficient and control wild type mice are dissected and the femoral heads are dislocated from the joints. The articular cartilage cap is removed by applying blunt force towards the articular surface with a pair of specially designed curved scissors under a dissecting microscope. Articular cartilage harvested from mouse femoral heads by this technique may contain essentially pure cartilage tissue with no visible contamination of subchondral bone. In another example, the cells from the subject organism can include a cartilaginous cell line, such as ATDC5 chondrogenic cells or another cartilaginous cell line known in the art.

While osteoarthritis does not occur in cultured cells, per se, drug candidate compounds for treating osteoarthritis can be screened in a cell culture system by looking for cells having a changed phenotype relative to untreated Nfat1 deficient cells. This is based at least in part on the observation that Nfat1 deficiency significantly affects the production of Nfat1's downstream effectors and major components of cartilage (e.g., aggrecan and type-II collagen), and bioactive substances that upregulate Nfat1 and/or affect the activity of Nfat1's downstream effectors can be viewed as being good drug candidates.

Expression levels of type-II collagen, aggrecan, and the other downstream effectors of Nfat1 can be detected in articular cartilage at the gene level using qPCR. Expression levels of type-II collagen, aggrecan, and the other downstream effectors of Nfat1 can be detected at the protein level by, for example, an enzyme-linked immunosorbent assay (ELISA).

Nfat1 expression can be "knocked down" in cells in culture using Nfat1 siRNA in normal articular cartilage cells and in insulin-treated ATDC5 chondrogenic cells. An example of an Nfat1 siRNA sequence is GAC-TAT-CTG-AAC-CCT-ATC-G (SEQ ID NO: 1). Preferably, the siRNA reduces Nfat1 expression by at least 10% relative to wild type cells. More preferably, the siRNA reduces Nfat1 expression by at least 20%, 40%, 50%, or 75% relative to wild type cells. Even more preferably, the siRNA reduces Nfat1 expression by at least 90% relative to wild type cells. Most preferably, the siRNA reduces Nfat1 expression by at least 99% relative to wild type cells.

In one embodiment, a method of screening drug candidates useful for treating primary osteoarthritis can include measuring production of Nfat1 and type II collagen in the cells from the subject organism. Also, a method of screening drug candidates useful for treating primary osteoarthritis can include measuring production of Nfat1 and aggrecan in the cells from the subject organism.

In one embodiment, a method of screening drug candidates useful for treating primary osteoarthritis can include a second screen. Performing a first screen as described above allows promising compounds to be identified relatively rapidly form a large library of candidate compounds. In a second screen, promising drug candidates identified in the first screen can be administered to an Nfat1-deficient organism (e.g., an Nfat1$^{-/-}$ mouse) to determine if they are effective in vivo. It is often the case that drug candidates that appear promising in cell culture are ineffective when administered to a whole organism Moreover, performing a second screen has the advantage of allowing detection of side-effects and/or other secondary toxicity effects that my not be apparent in cell culture.

As such, the second screen can include (1) exposing the subject organism to at least one drug candidate identified in the first screen, and (2) probing the organism for increased and/or decreased Nfat1 activity, altered activity and/or production of the downstream effectors of Nfat1, and/or probing for an improved osteoarthritis phenotype relative to a control organism not receiving the at least one drug candidate.

Osteoarthritis phenotypes that may be observed in an organism can include, but are not limited to, loss of major components of articular cartilage such as type-II collagen and aggrecan, proliferation of articular chondrocytes and formation of chondrocyte clusters, formation of chondrophytes and osteophytes (bone spurs), alteration in the thickness/density of subchondral bone beneath the cartilaginous joint surface, roughening of articular surface, loss of articular cartilage, destruction of joint structure, and reduced range of joint motion in the Nfat1 negative and/or deficient mouse. In addition, overexpression (or loss of expression) of Nfat1's downstream effectors can also be observed in OA. A suitable drug candidate identified in a second screen could be one that rescues or improves one or more of the adverse phenotypes associated with Nfat1 deficiency in the organism or that upregulates Nfat1 expression, or that restores balance to the anabolic and catabolic activities in the joints of an Nfat1-deficient organism.

V. OA-Like Changes in Weight-Bearing Joints of Adult NFAT1-Deficient Mice

Figure 1B:
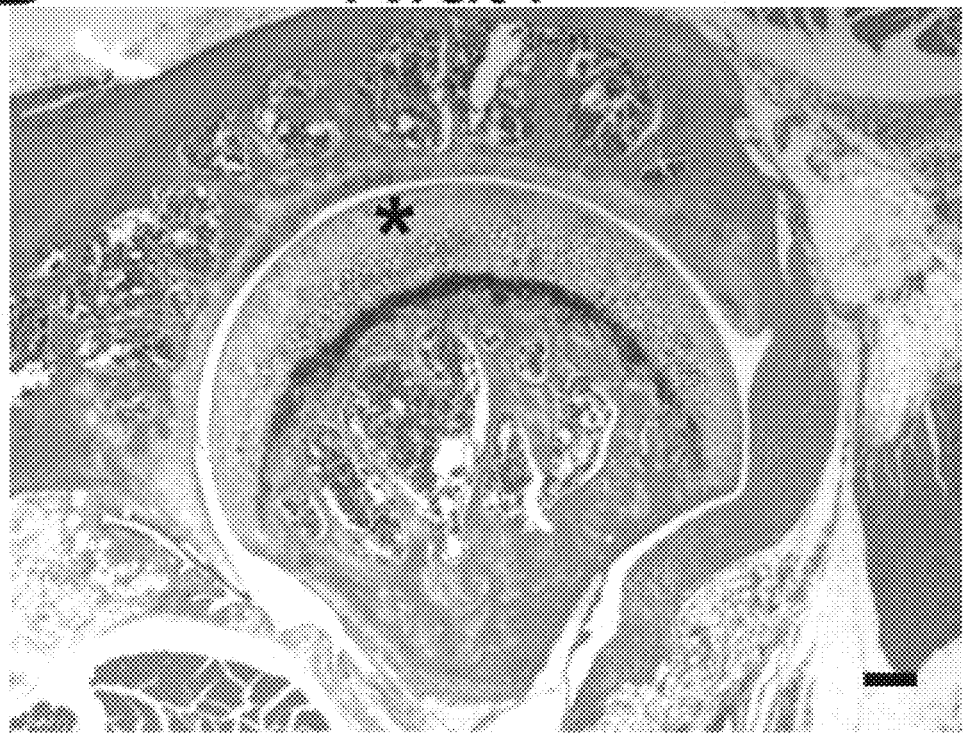
FIG. 1B illustrates a 2-month-old female Nfat1$^{-/-}$ mouse showing a focal loss of safranin-O staining (i.e., loss of darker staining) for proteoglycans in the superficial/upper zone (*) of femoral head articular cartilage.
Figure 1C:
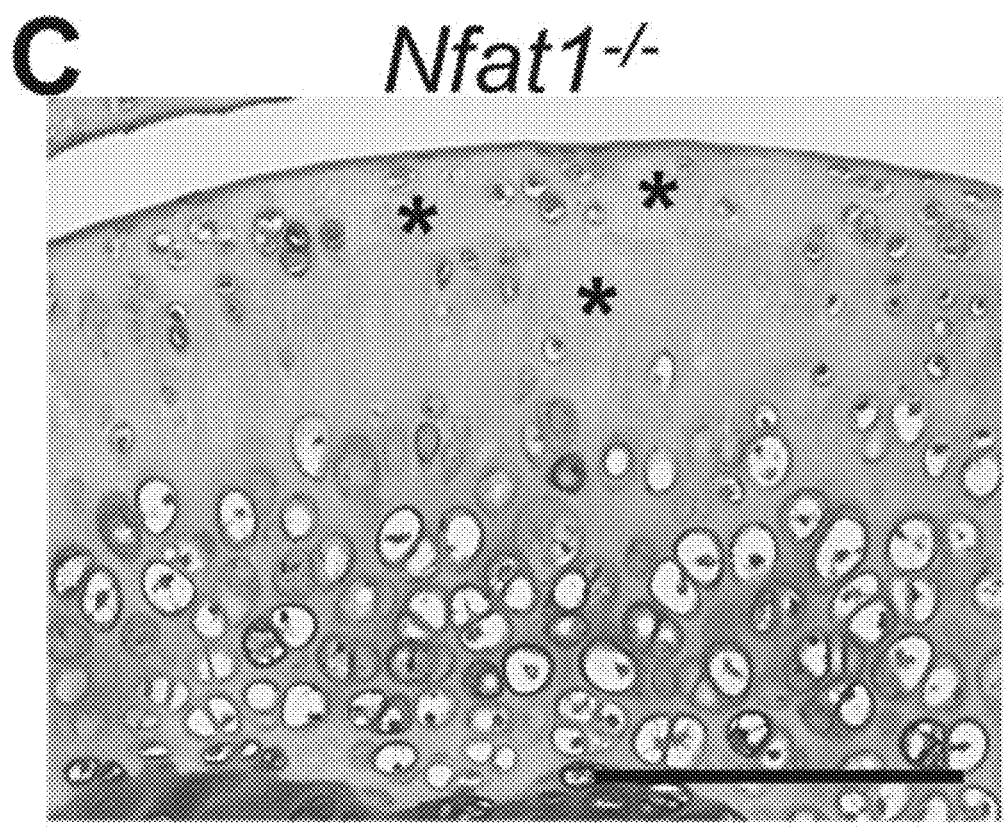
FIG. 1C illustrates higher magnification of the image in FIG. 1B.
Figure 1D:
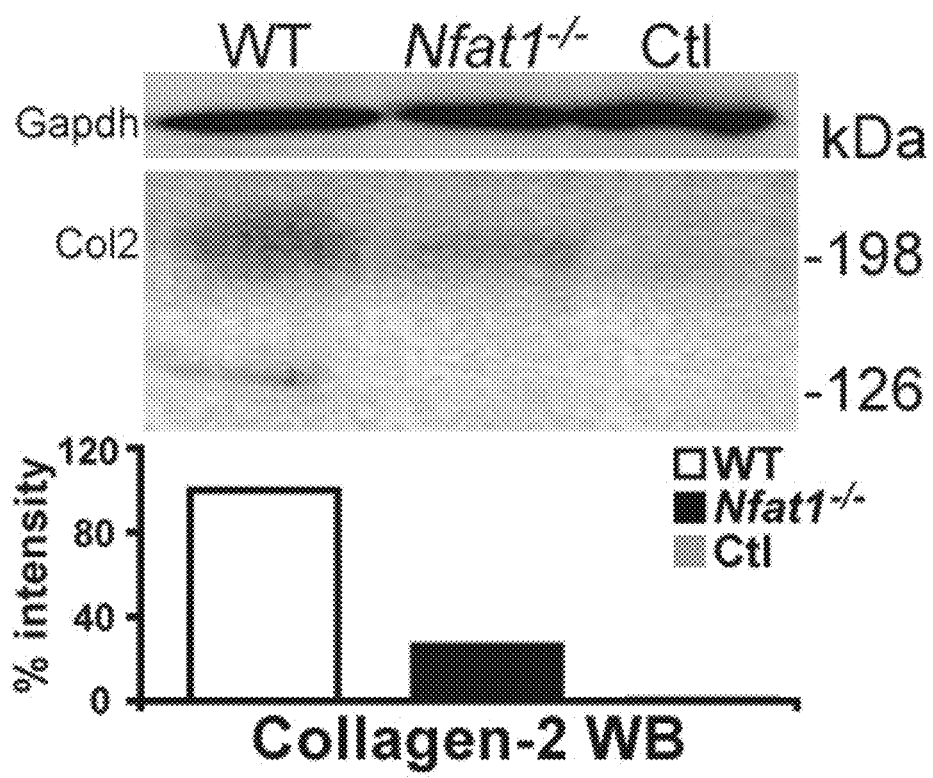
FIG. 1D illustrates a Western-blot and intensity data comparing collagen-2 (Col2) protein expression levels in articular cartilage of 2-month-old female WT and Nfat1$^{-/-}$ mice.
Figure 1E:
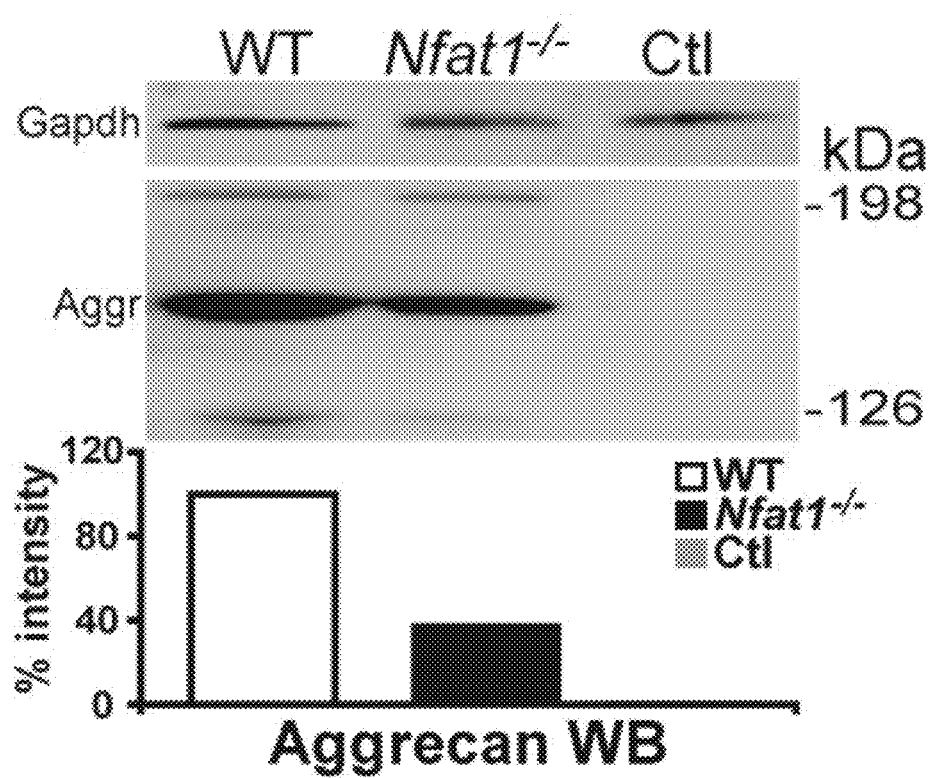
FIG. 1E illustrates a Western-blot and intensity data comparing aggrecan (Aggr) protein expression levels in articular cartilage of 2-month-old female WT and Nfat1$^{-/-}$ mice.
Figure 1F:
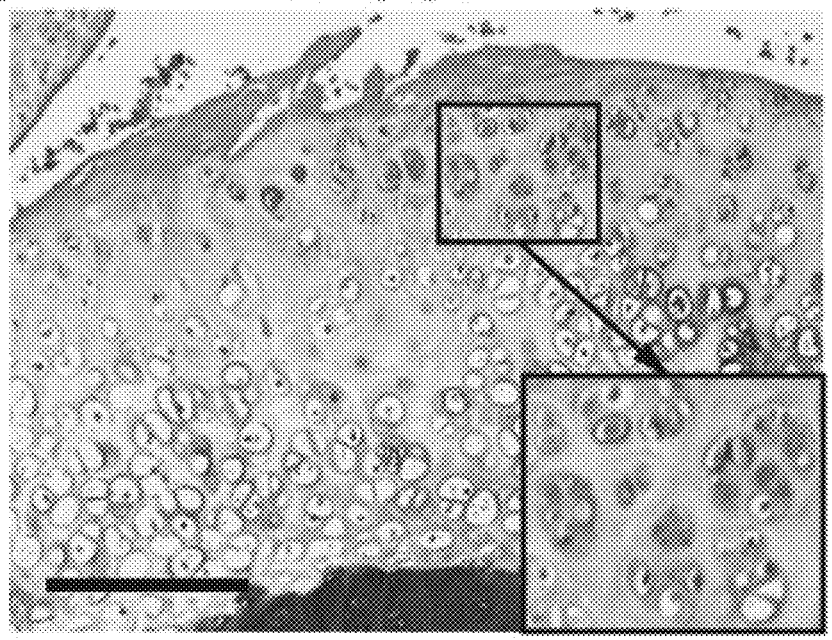
FIG. 1F illustrates roughening of the articular surface, focal loss of proteoglycan staining, and early chondrocyte clustering (in magnified square) in the upper-mid zones of articular cartilage of a 4-month-old female Nfat1$^{-/-}$ hip.

Histopathological studies of the skeletal system revealed no abnormalities in newborn and 1-month Nfat1$^{-/-}$ mice (data not shown). By 2 months of age, however, young-adult stage in mice show loss of safranin-O-stained proteoglycans (FIG. 1A-1C), collagen-2 (FIG. 1D), and aggrecan (FIG. 1E) in female Nfat1$^{-/-}$ femoral head articular cartilage. At 3-4 months, focal loss of proteoglycans and articular surface roughening with early chondrocyte clustering were seen in Nfat1$^{-/-}$ articular cartilage (FIG. 1F). Nfat1$^{-/-}$ knees, ankles, shoulders, and elbows also show focal loss of proteoglycans in articular cartilage at this stage (data not shown).

Figure 1G:
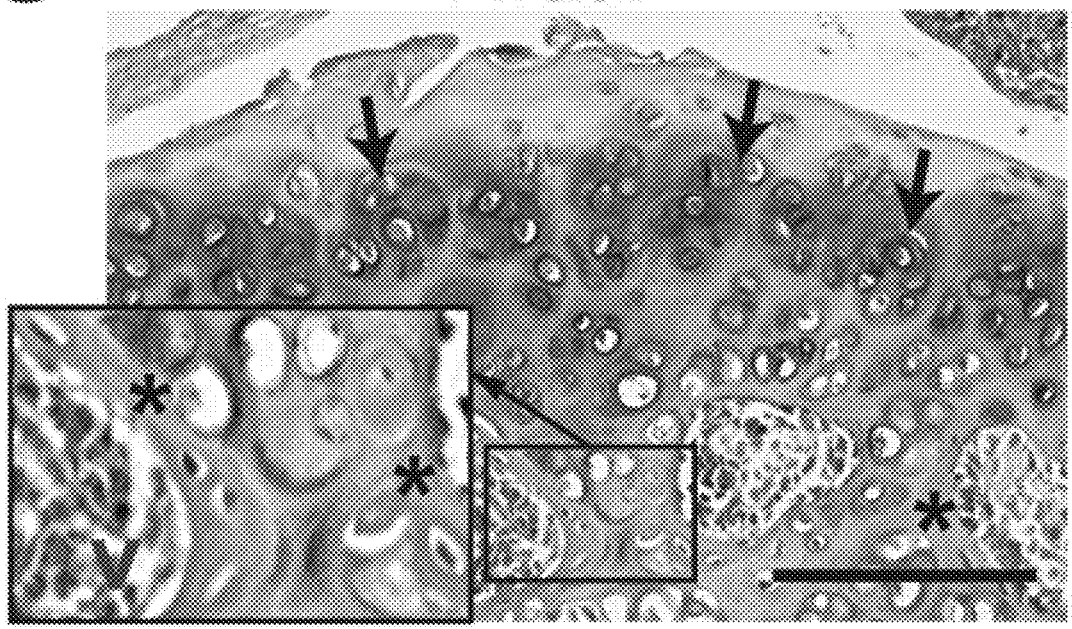
FIG. 1G illustrates a 6-month Nfat1$^{-/-}$ hip joint showing roughening and discontinuity of articular surface, loss of safranin-O staining in the upper zone, chondrocyte clustering in the upper-mid zones (arrows), and increased safranin-O staining in mid-deep zones of femoral head articular cartilage. Endochondral ossification, including chondrocyte differentiation/hypertrophy, vascular invasion (v), and new bone formation (*) on the surfaces of calcifying cartilage, is seen in subchondral bone (insert).
Figure 1H:
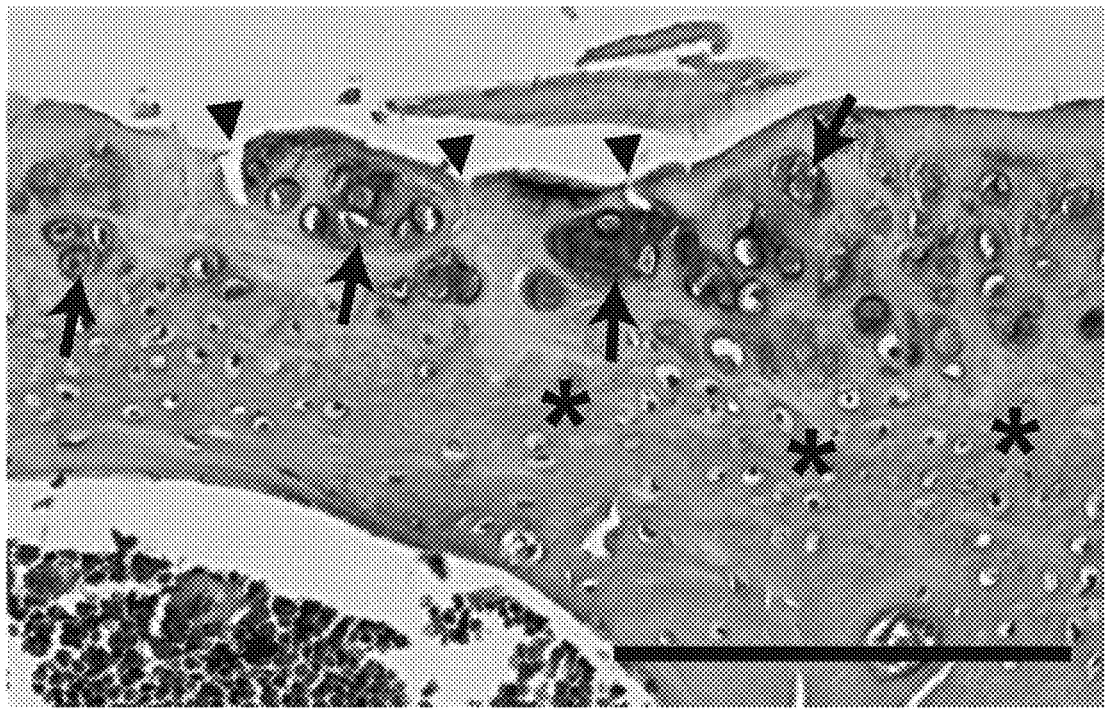
FIG. 1H illustrates a 12-month Nfat1$^{-/-}$ shoulder (glenoid) shows chondrocyte clusters (arrows) with thickened subchondral bone (*) and vertical clefts in the superficial zone of articular cartilage (arrowheads).
Figure 1I:
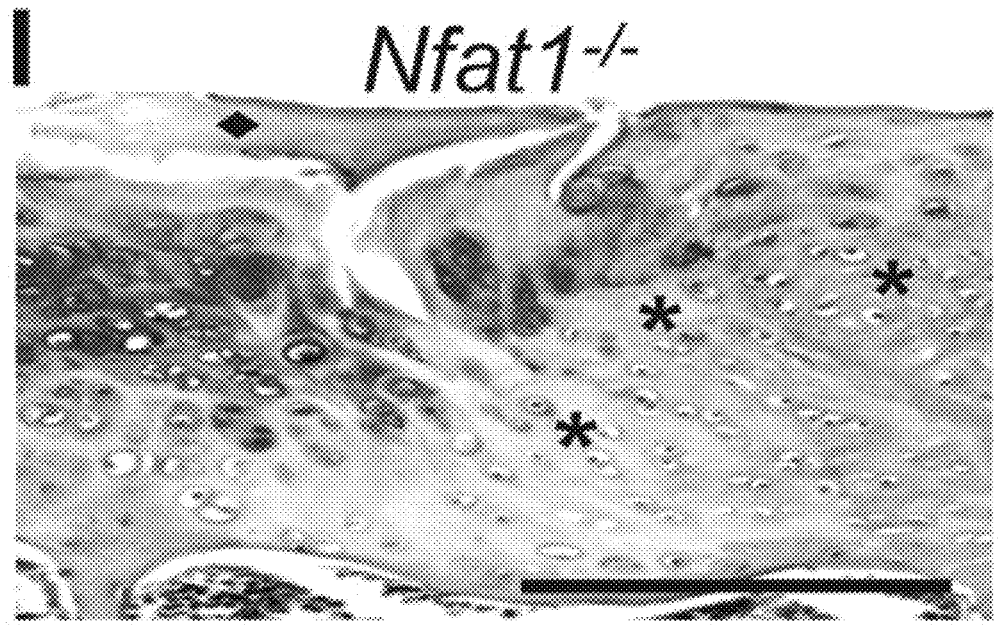
FIG. 1I illustrates a 15-month Nfat1$^{-/-}$ humeral head displaying a fragment of cartilage (♦) derived from deteriorated articular cartilage due to a combination of horizontal and vertical fissures/clefts. Increased proteoglycan staining is evident in the areas adjacent to the fissures. Thickened subchondral bone (*) is clearly seen.

Early degradation of articular cartilage was followed by reparative cellular activity in Nfat1$^{-/-}$ articular cartilage and subchondral bone. Focal chondrocyte proliferation with increased proteoglycan staining became evident in the upper-middle zones of Nfat1$^{-/-}$ articular cartilage after 4 months. Chondrocyte differentiation and hypertrophy occurred in the deep-calcified zones of Nfat1$^{-/-}$ articular cartilage (FIG. 1G). Mesenchymal cells derived from subchondral bone marrow cavities differentiated into chondrocytes which underwent hypertrophy and endochondral ossification, leading to thickening of subchondral bone. Reparative proliferating articular chondrocytes later formed cell clusters but failed to regenerate deteriorated articular cartilage (FIGS. 1G-1I).

Figure 1J:
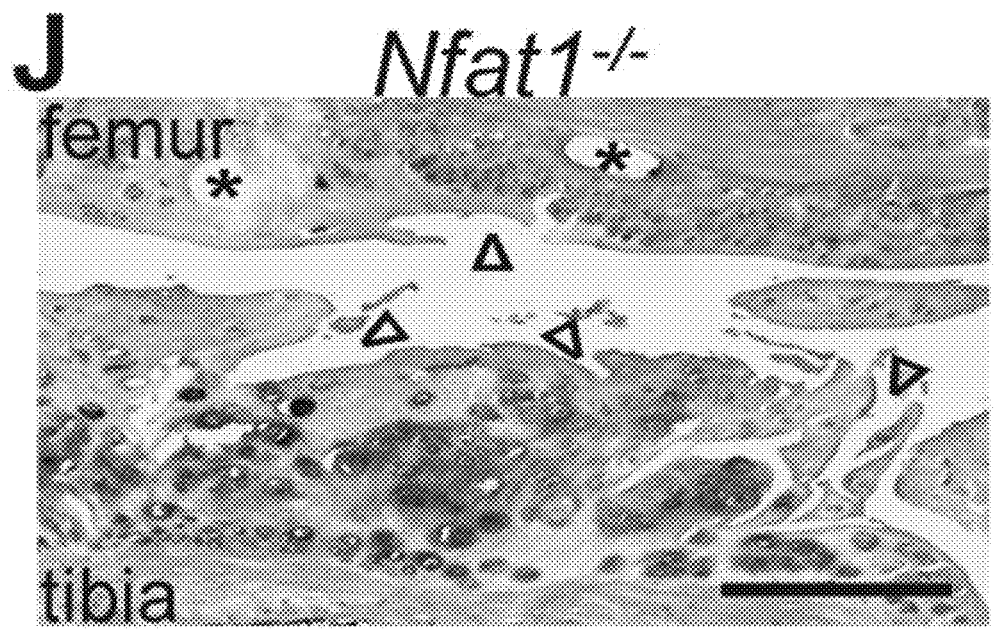
FIG. 1J illustrates articular cartilage destruction with surface fibrillation (Δ) and subchondral bone cysts (*) in a 15-month Nfat1$^{-/-}$ knee joint.
Figure 1K:
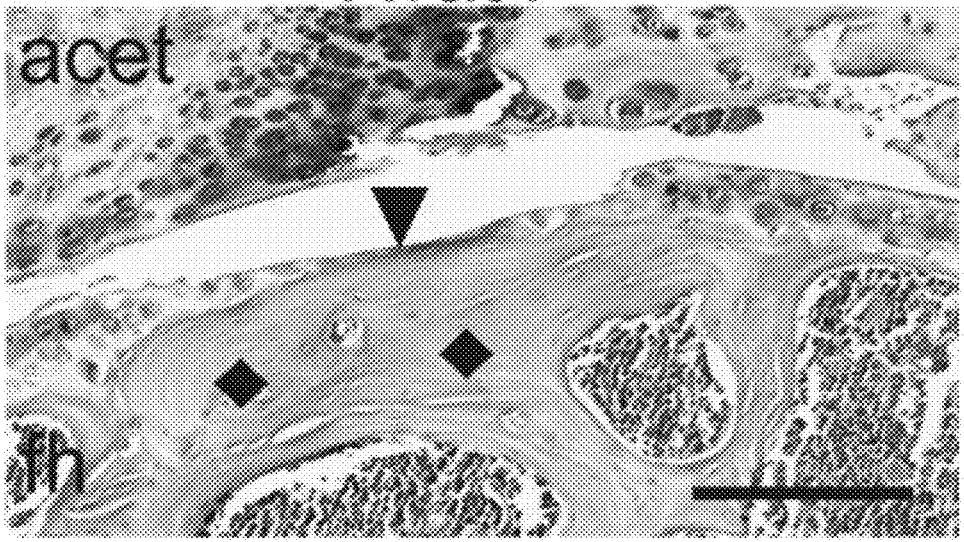
FIG. 1K illustrates an 18-month Nfat1$^{-/-}$ hip showing thinning or complete loss of articular cartilage (eburnation) (arrowhead) with exposure of thickened subchondral bone (♦).
Figure 1L:
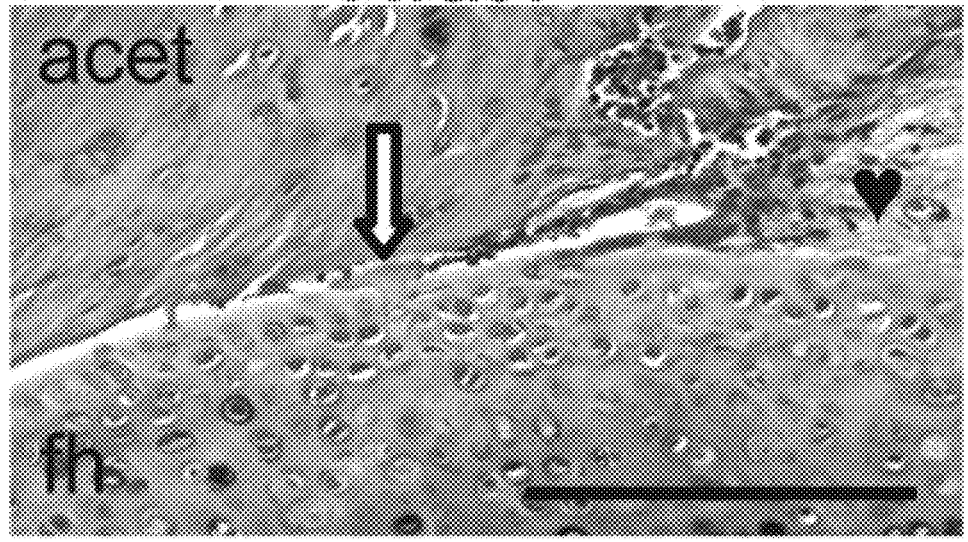
FIG. 1L illustrates an 18-month Nfat1$^{-/-}$ hip showing narrowing of joint space (open arrow) and fibrous joint fusion (♥)

From 15 to 24 months, progressive loss of articular cartilage and formation of subchondral bone cysts (FIG. 1J), one of the characteristics of human OA, exposure and thickening of subchondral bone (FIG. 1K), and narrowing of joint space (FIG. 1L) became evident in weight-bearing joints of Nfat1$^{-/-}$ mice. These histopathological changes are similar to those seen in late-stage human OA. The OA-like phenotypes of Nfat1$^{-/-}$ mice were limited to weight-bearing appendicular joints and occurred earlier in females than males. Abnormal cartilage formation was not observed in and around other cartilaginous tissues such as the xyphoid, residual growth plates, or spinal and maxillofacial joints. Similar, but less severe OA-like changes were seen in 12-month or older heterozygous (Nfat1$^{+/-}$) mice, suggesting that Nfat1 gene dosage affects the time of onset and the severity of OA (data not shown).

Figure 2:
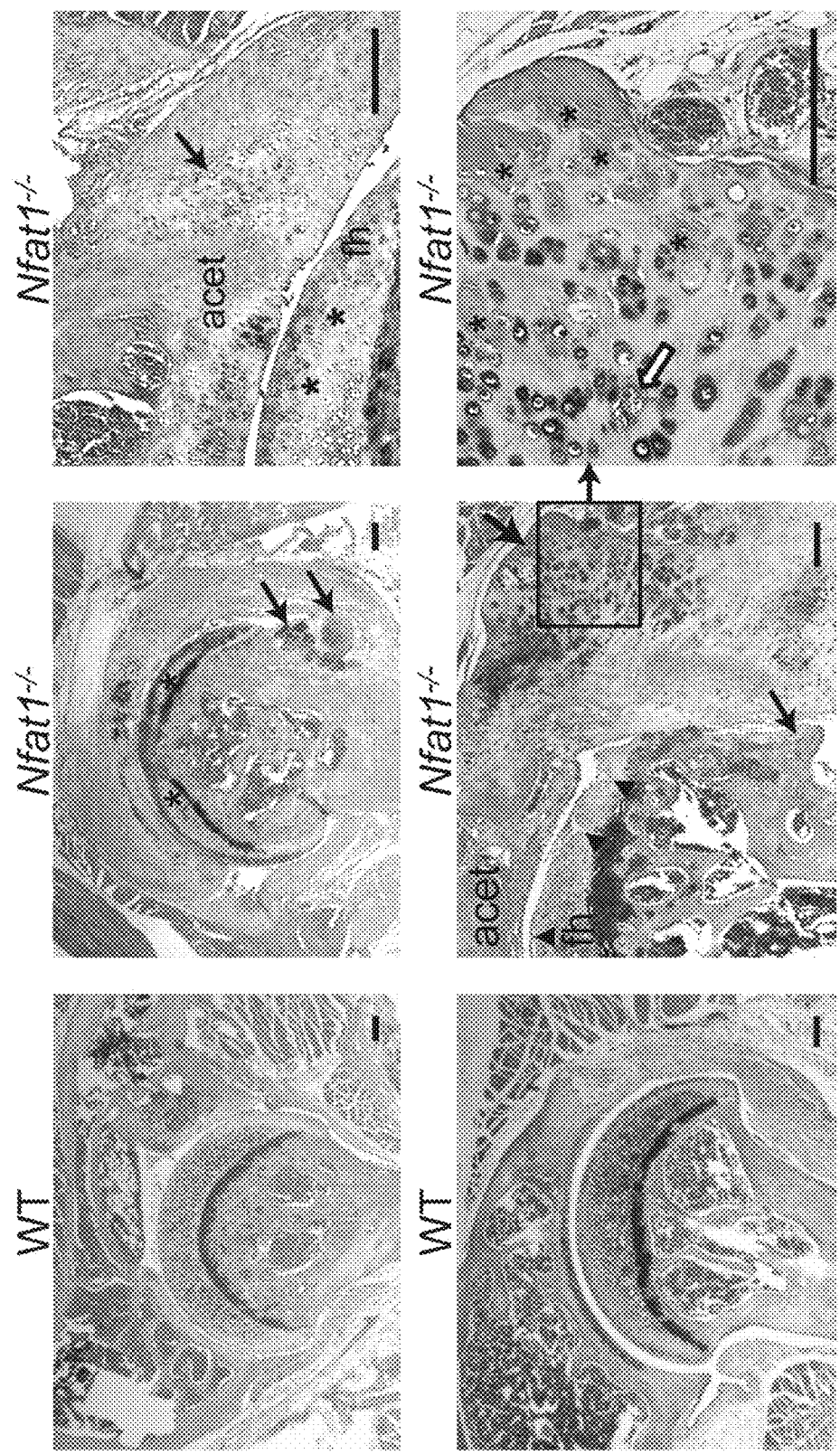
FIG. 2 illustrates histology sections comparing wild-type (WT) and Nfat1$^{-/-}$ hip joints showing loss of proteoglycan staining (*) in articular cartilage, roughening of articular surface (▲), and formation of chondro-osteophytes (arrows) in Nfat1$^{-/-}$ hip joints. The process of endochondral ossification is seen in the chondro-osteophytes, including chondrocyte hypertrophy and vascular invasion (open arrow). Cartilage has been partially replaced by newly formed bone (*).

Reparative chondrocytic activity was also activated in Nfat1$^{-/-}$ periarticular tissues (synovium and periosteum near articular cartilage). At 3-4 months, mesenchymal progenitor cells in periarticular tissues proliferated and differentiated into chondrocytes forming chondrophytes (FIG. 2). These chondrophytes subsequently underwent endochondral ossification and formed chondro-osteophytes or osteophytes around the margins of deteriorated articular cartilage (FIG. 2). The abnormal chondrocyte proliferation/differentiation and subsequent osteophyte formation occurring in Nfat1$^{-/-}$ periarticular tissues appeared to be a secondary reparative reaction to the initial articular cartilage degradation that had occurred prior to the formation of periarticular chondrophytes.

Figure 3A:
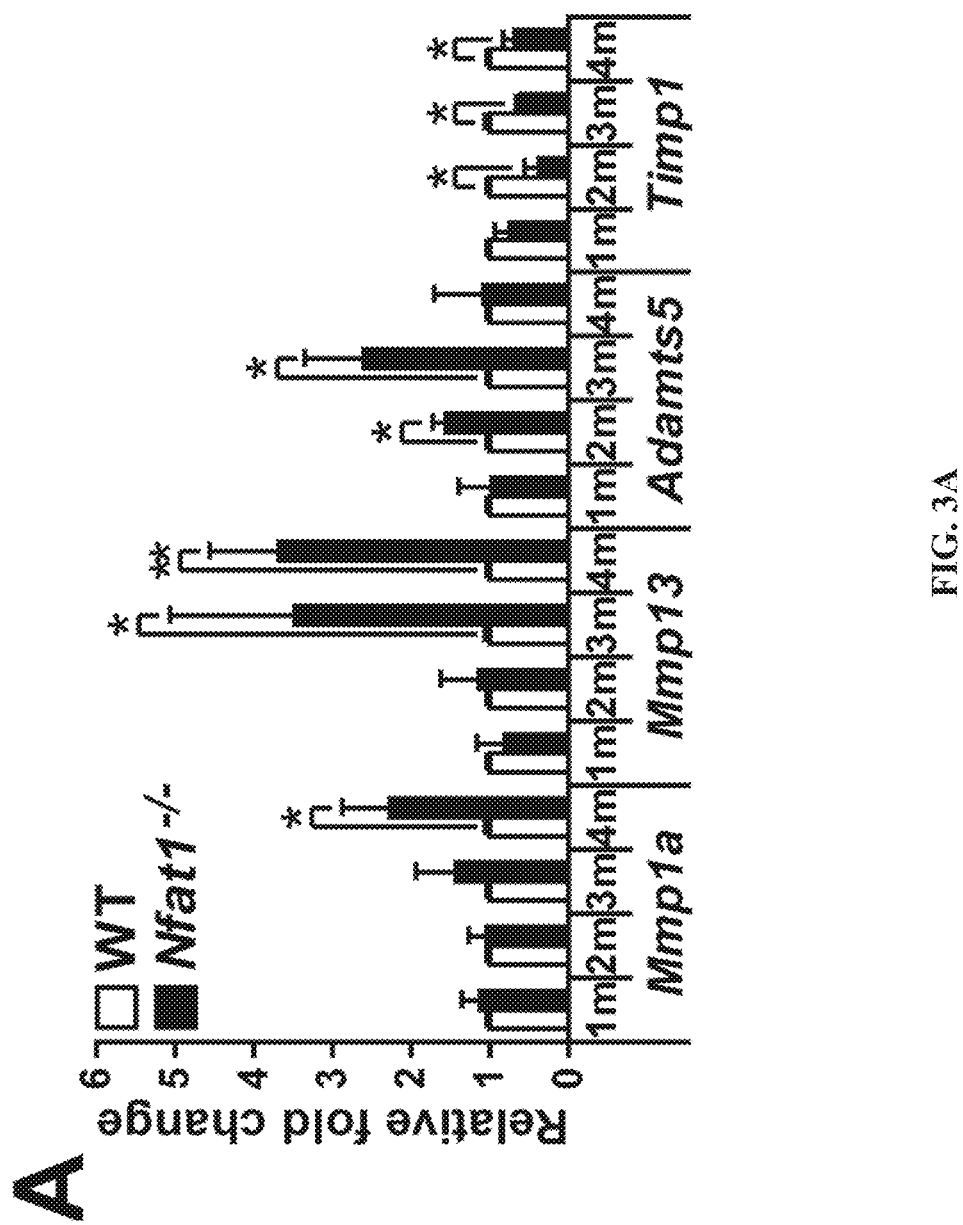
FIG. 3A illustrates qPCR analyses showing increased catabolic activities of articular chondrocytes isolated from Nfat1$^{-/-}$ hip joints.
Figure 3B:
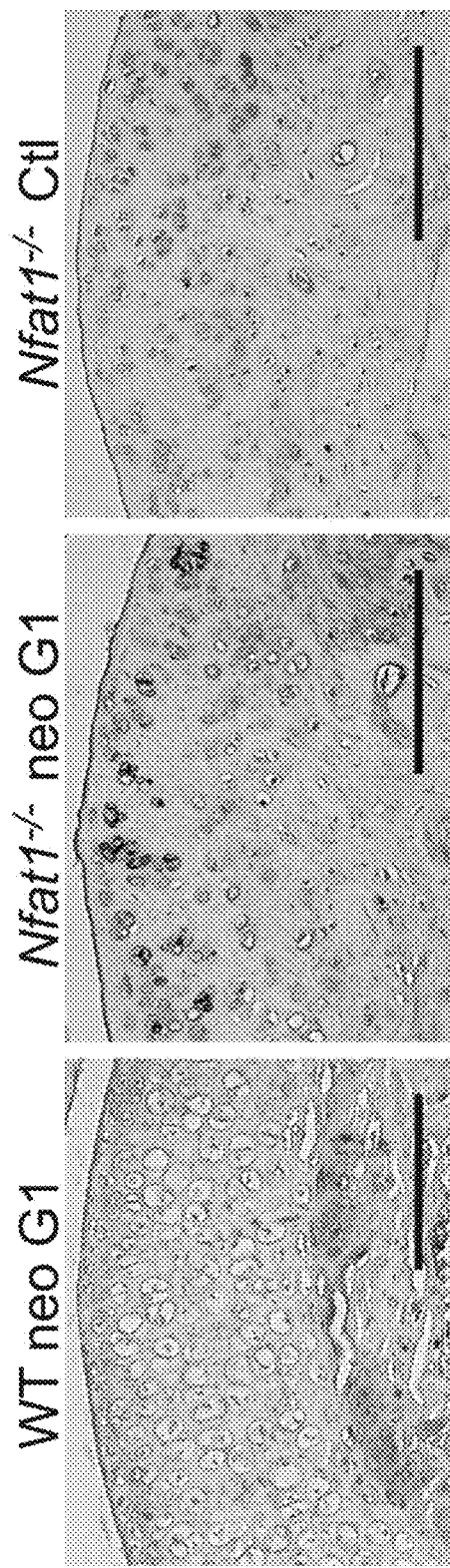
FIG. 3B illustrates immunohistochemical staining using antibody that detects degraded aggrecan showing degraded aggrecan was substantially more prevalent around cells in the upper zone of 3-month old female Nfat1$^{-/-}$ femoral head articular cartilage than age-matched WT mice.
Figure 3C:
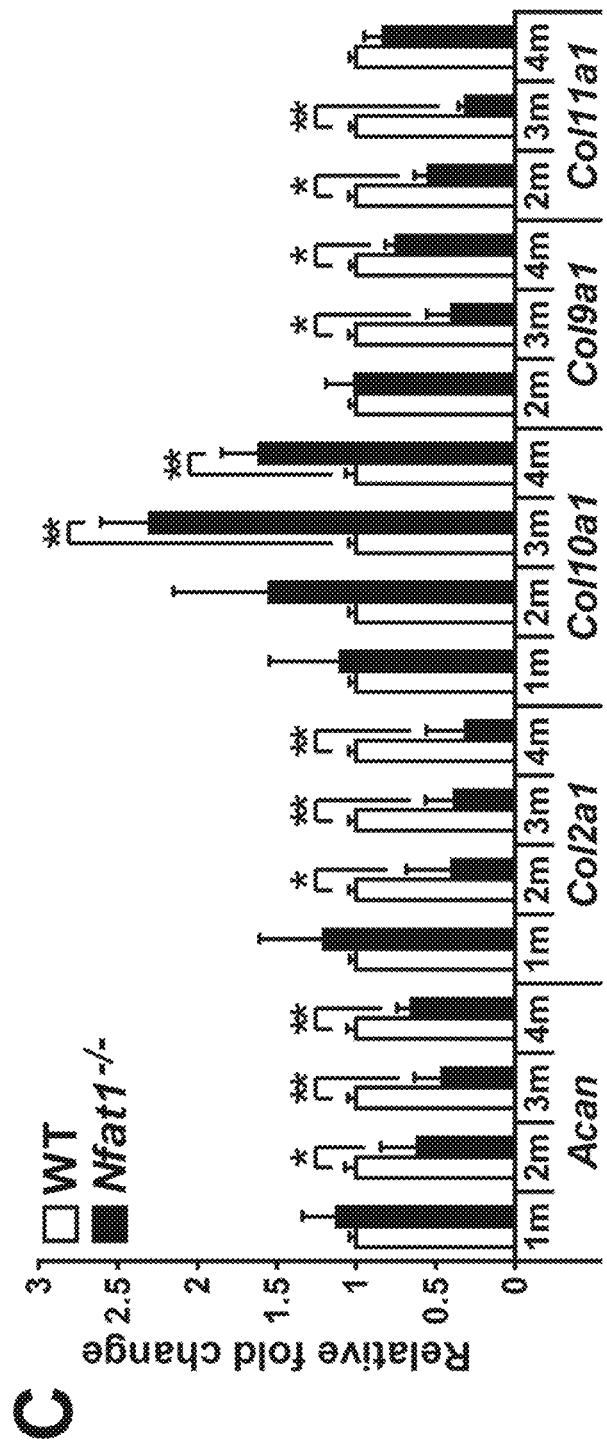
FIG. 3C illustrates qPCR analyses showing temporal changes in expression levels of various genes of interest (i.e., Acan, Col2a1, Col10a1, Col9a1, Col11a1) in WT and Nfat1$^{-/-}$ articular cartilage at 1-4 months.
Figure 3D:
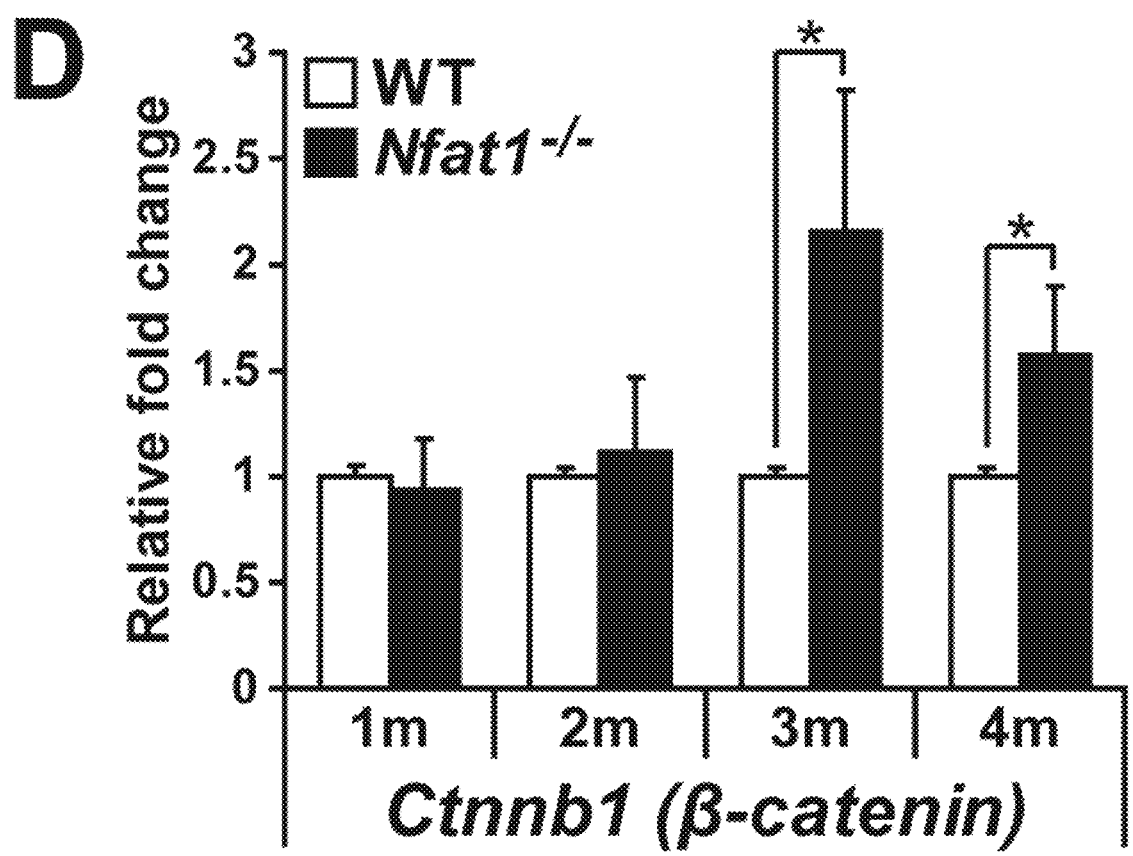
FIG. 3D illustrates qPCR analyses showing temporal changes in expression levels of β-catenin in WT and Nfat1$^{-/-}$ articular cartilage at 1-4 months.
Figure 3E:
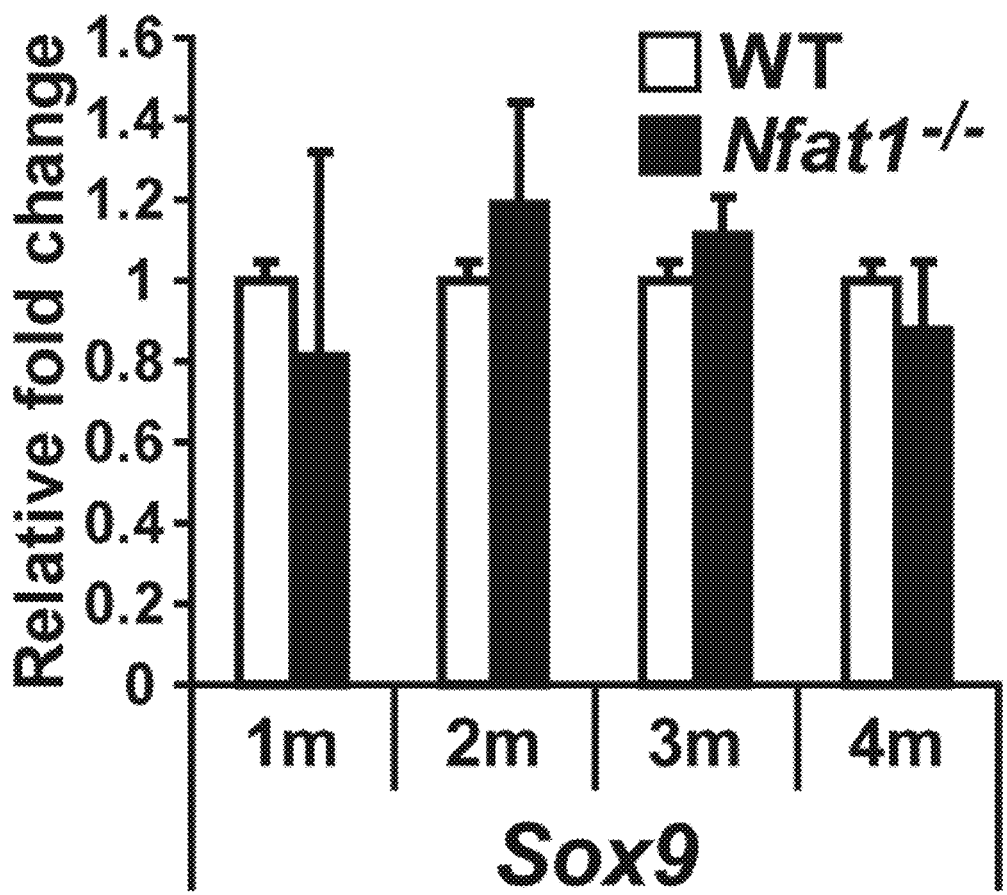
FIG. 3E illustrates qPCR analyses showing temporal changes in expression levels of Sox9 in WT and Nfat1$^{-/-}$ articular cartilage at 1-4 months.
Figure 3F:
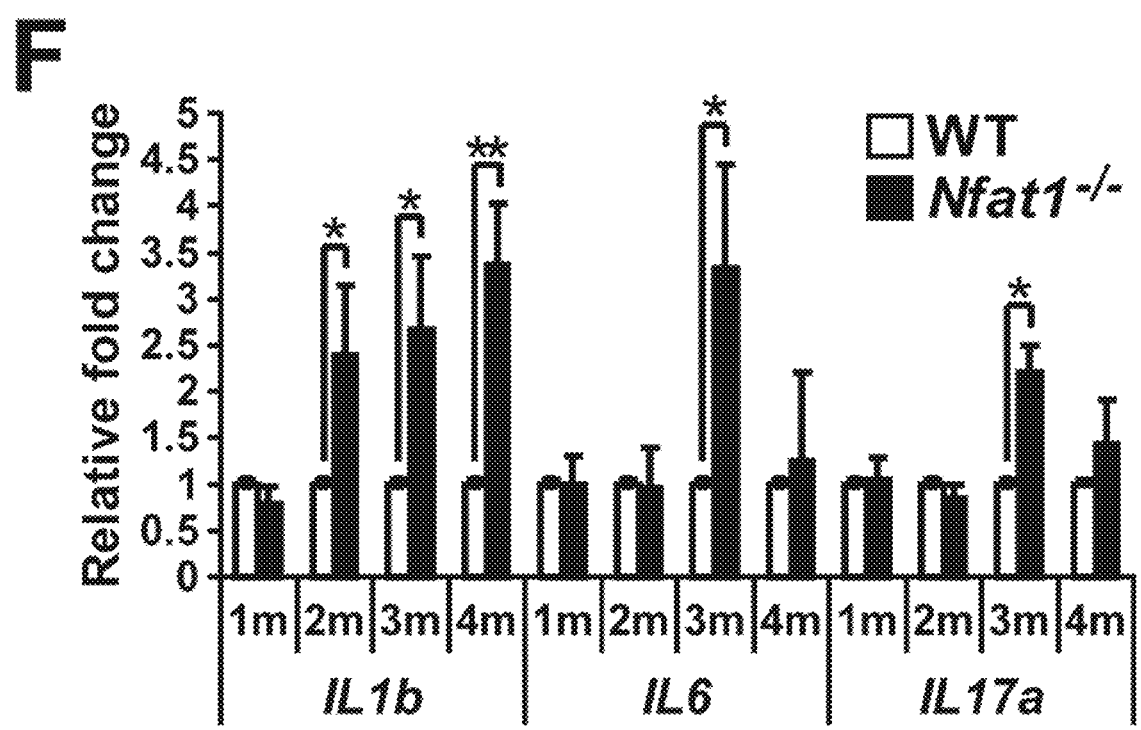
FIG. 3F illustrates qPCR analyses showing temporal changes in expression levels of various genes of interest (i.e., IL1β, IL6, IL17α) in WT and Nfat1$^{-/-}$ articular cartilage at 1-4 months.
Figure 3G:
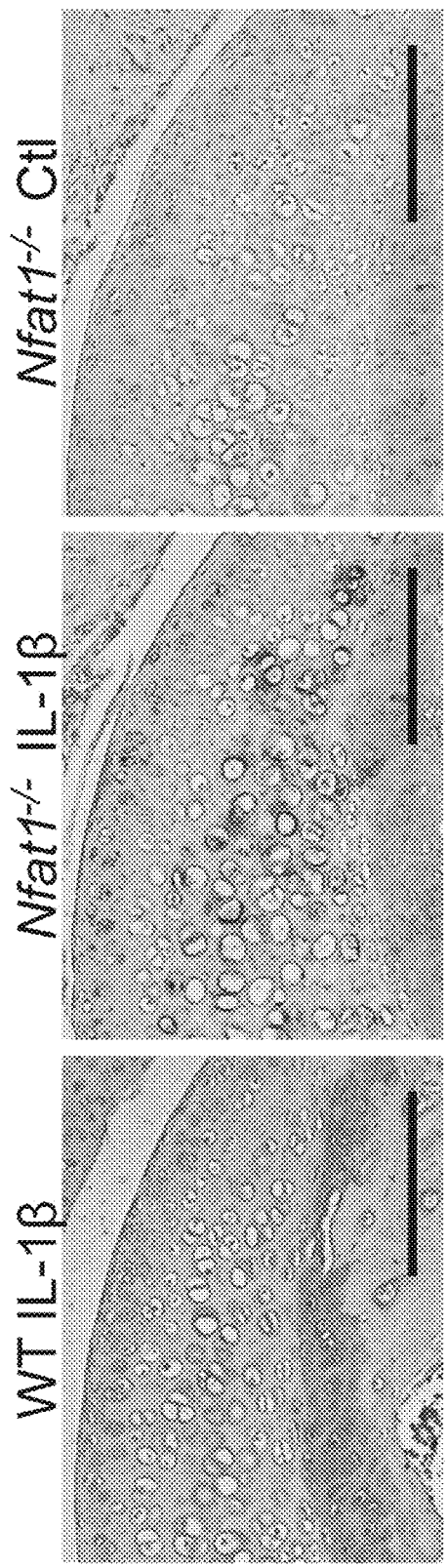
FIG. 3G illustrates immunohistochemical staining of IL-1β expression showing substantially more expression of IL-1β in femoral head articular cartilage of 3-month-old Nfat1$^{-/-}$ mice compared to age-matched WT mice.

VI. Loss of NFAT1 Leads to an Imbalance Between Catabolic and Anabolic Activities of Adult Articular Chondrocytes To explore the molecular and cellular mechanisms for the development of Nfat1 deficiency-induced OA, the effects of Nfat1 deficiency on the catabolic and anabolic activities of articular chondrocytes during the initiation stage of OA (i.e., age 2-4 months) were examined. Catabolic activity was represented by increased expression levels of cartilage-degrading proteinases including MMPs (matrix metalloproteinases) and ADAMTS (a disintegrin and metalloproteinase with thrombospondin motifs), and proinflammatory cytokines. Anabolic activity was indicated by the expression of chondrocyte marker genes in articular cartilage. qPCR analyses demonstrated that expression of Mmp1a, Mmp13, and Adamts5, but not Mmp-3, -8, -9 or Adamts4 (data not shown), was significantly increased, while Timp1 (tissue inhibitor of metalloproteinase-1) expression was decreased in Nfat1$^{-/-}$ articular cartilage (FIG. 3A). Immunohistochemistry using aggrecan neo G1 antibody, which detects the degraded aggrecan product, displayed increased aggrecan degradation in Nfat1$^{-/-}$ articular cartilage (FIG. 3B). The data suggest that Mmp13 and Adamts5 likely play a major role in degrading cartilage matrix at the initiation stage of Nfat1 deficiency-induced OA. The expression of chondrocyte marker genes Acan (encoding aggrecan), Col2α1, Col9α1, and Col11α1 (encoding collagen-2, -9, and -11) was decreased, while Col10a1 (a hypertrophic chondrocyte marker) was elevated and temporally associated with the up-regulation of Ctnnb1 (encoding β-catenin) in Nfat1$^{-/-}$ articular cartilage (FIGS. 3C, 3D). However, no significant difference in Sox9 expression was detected between WT and Nfat1$^{-/-}$ articular cartilage (FIG. 3E). Expression levels of proinflammatory cytokine genes for IL-1β, IL-6, and IL-17α (FIG. 3F), but not IL-18 and tumor necrosis factor-α (Tnfα) (data not shown), were significantly up-regulated at 2-4 months. Immunohistochemistry demonstrated substantially more intense IL-1β staining in Nfat1$^{-/-}$ than in WT articular cartilage (FIG. 3G). Genes for anti-inflammatory cytokines (IL-4, -10, and -13) displayed no significant changes in Nfat1$^{-/-}$ articular cartilage (data not shown).

Forced expression of Nfat1 using lentiviral vectors in cultured 3-month old primary Nfat1$^{-/-}$ articular chondrocytes partially or completely rescued the abnormal catabolic and anabolic activities of Nfat1$^{-/-}$ articular chondrocytes (FIGS. 4A-4C). These results suggest that Nfat1 deficiency causes an imbalance between catabolic and anabolic activities of young adult chondrocytes favoring catabolism, leading to increased cartilage degradation and decreased anabolic metabolism of articular chondrocytes at the initiation stage of OA.

Figure 5A:
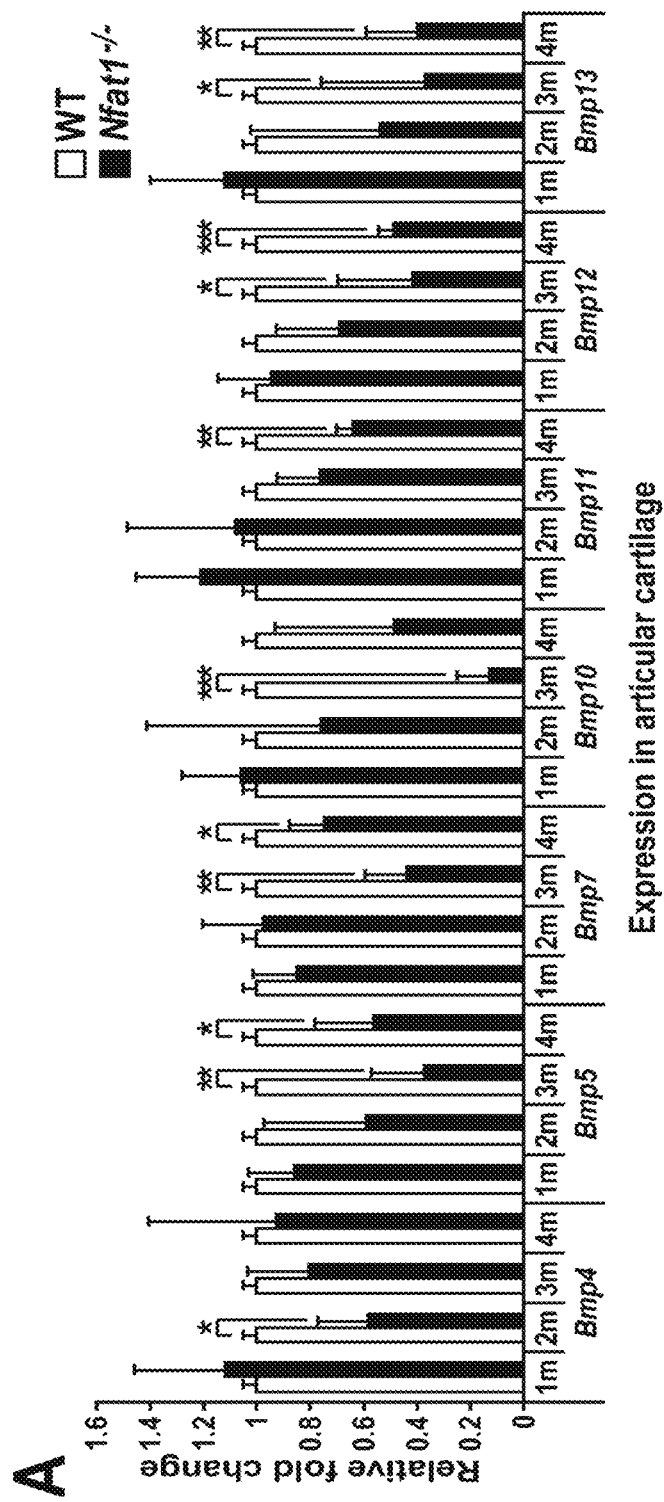
FIG. 5A illustrates qPCR analyses showing differential expression of Bmp2-15 in articular cartilage in WT and Nfat1$^{-/-}$ mice at 1-month to 4-months of age (Bmp members without significant changes not shown).
Figure 5B:
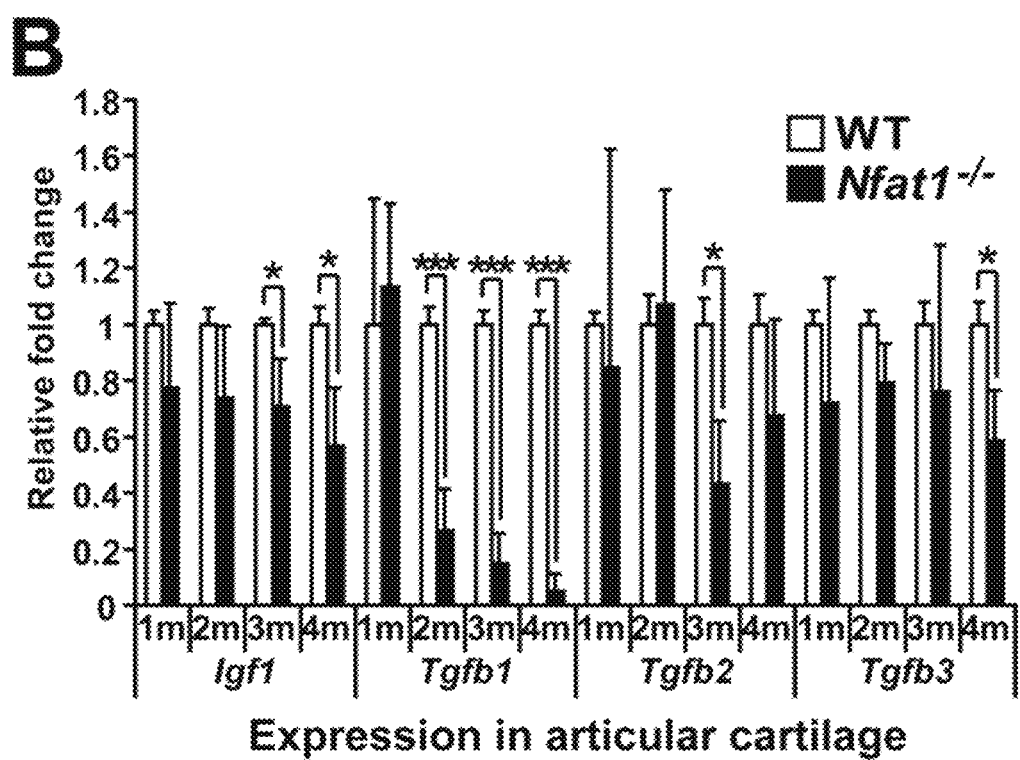
FIG. 5B illustrates qPCR analyses showing differential expression of Igf1 and Tgfb1-3 in articular cartilage in WT and Nfat1$^{-/-}$ mice age 1-month to 4-months.
Figure 5C:
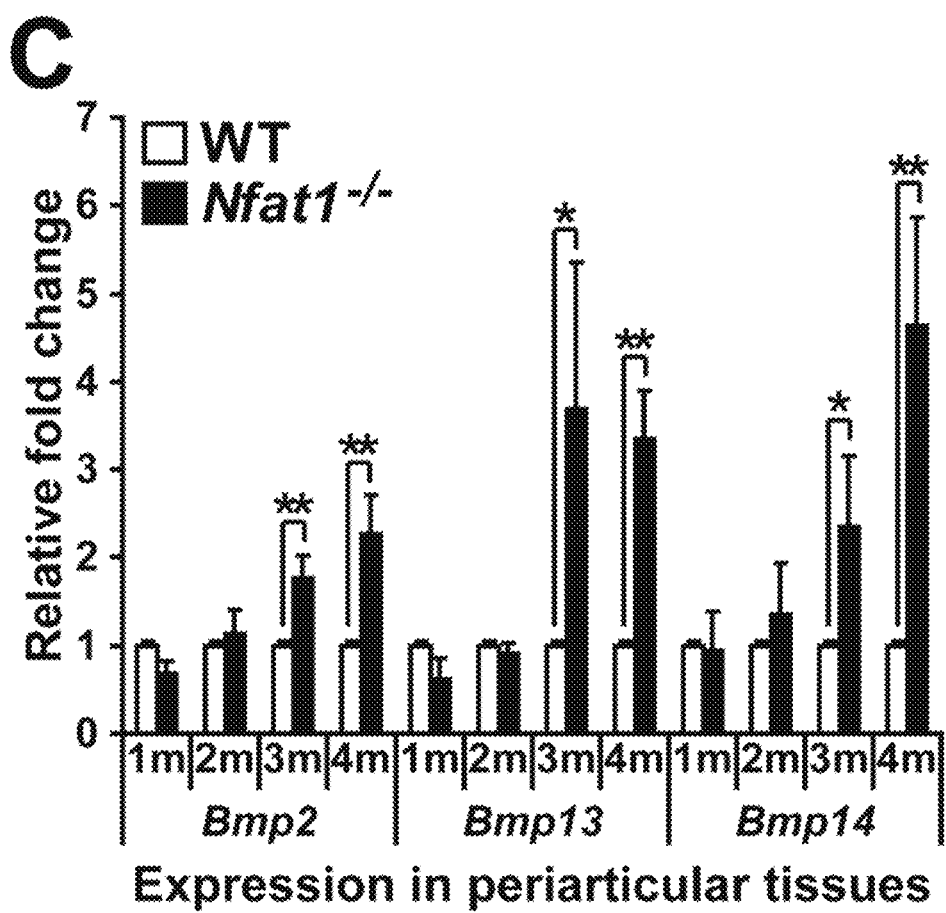
FIG. 5C illustrates qPCR analyses showing differential expression of Bmp2, Bmp13, and Bmp14 in periarticular tissues in WT and Nfat1$^{-/-}$ mice age 1-month to 4-months.
Figure 5D:
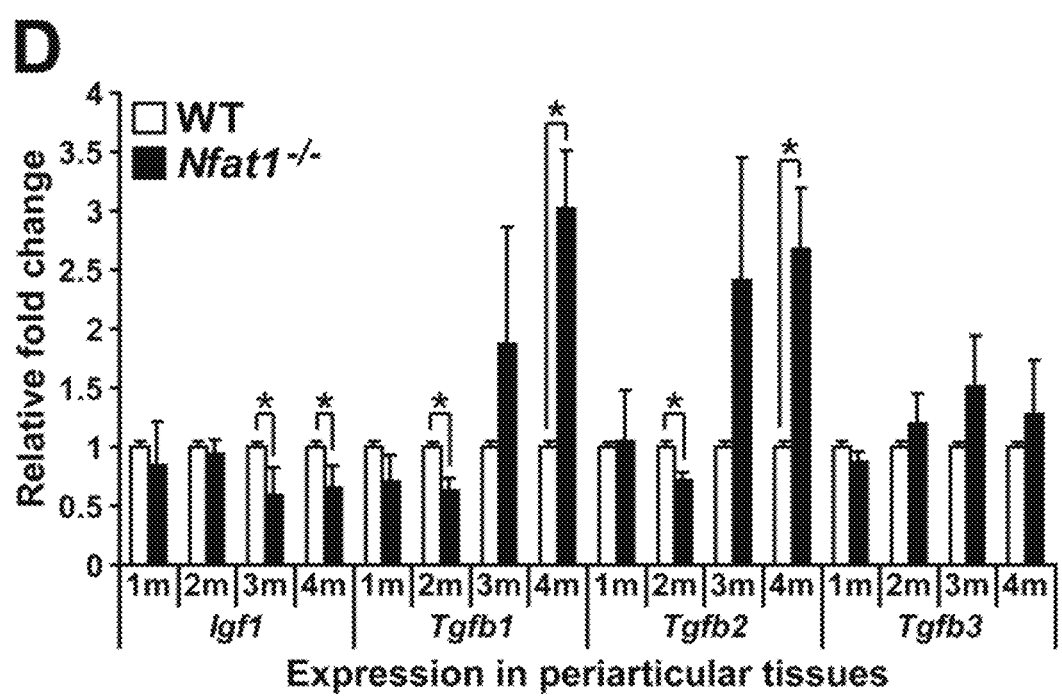
FIG. 5D illustrates qPCR analyses showing differential expression of Igf1 and Tgfb1-3 in periarticular tissues in WT and Nfat1$^{-/-}$ mice at 1-month to 4-months of age.
Figure 5E:
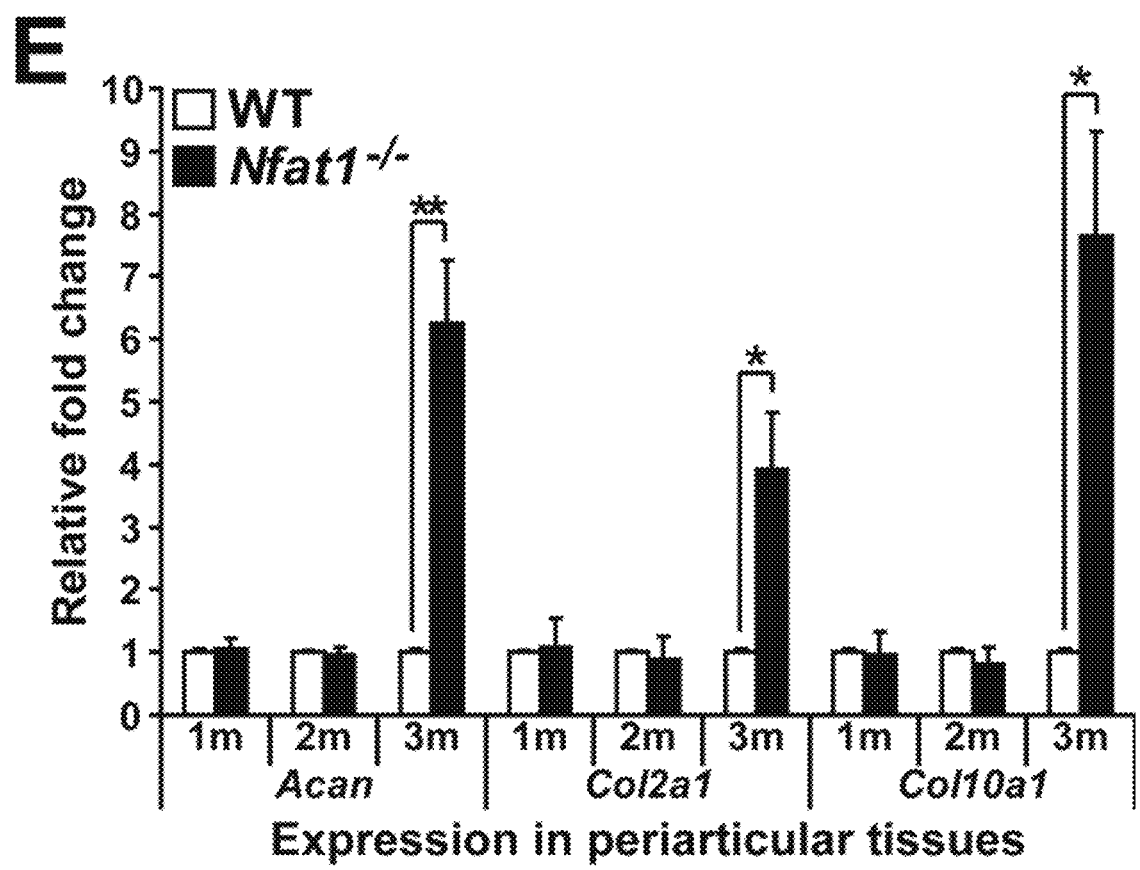
FIG. 5E illustrates qPCR analyses showing differential expression of Acan, Col2α1, and Col10α1 in periarticular tissues in WT and Nfat1$^{-/-}$ mice at 1-month to 4-months of age.

VII. Differential Expression of Specific Growth Factors Between NFAT1$^{-/-}$ Articular Cartilage and Peri-Articular Tissues is Associated with OA-Like Cartilage Phenotypes To explore the mechanisms by which Nfat1$^{-/-}$ articular cartilage showed reduced expression of chondrocyte markers whereas Nfat1$^{-/-}$ periarticular tissues displayed enhanced cartilage formation during the initiation stage of OA, the expression levels of a large number of growth factors in both articular cartilage and periarticular tissues at 1-4 months was examined. Insulin-like growth factor-1 (IGF-1), transforming growth factor-β1 (TGF-β), and bone morphogenetic proteins (BMPs) are known to induce chondrogenic differentiation and/or maintain the function of chondrocytes. TGF-β1 and BMPs may also potentiate osteophyte formation. qPCR analyses demonstrated that expression of several Bmps, Igf1, and Tgfb1-3 decreased at 2-4 months in Nfat1$^{-/-}$ articular cartilage (FIGS. 5A, 5B), while Bmp2, Bmp13, Bmp14, and Tgfb1-2 were up-regulated after 2 months in Nfat1$^{-/-}$ periarticular tissues (FIGS. 5C, 5D). Acan, Col2a1, and Col10a1 expression was normal at 1-2 months and elevated at 3 months, correlating with chondrocyte differentiation in Nfat1$^{-/-}$ periarticular tissues (FIG. 5E).

These findings suggest that reduced anabolic activity of articular chondrocytes correlates with decreased expression of specific BMPs, TGF-βs, and IGF1, while enhanced periarticular cartilage differentiation is associated with up-regulated expression of specific BMPs and TGF-βs in Nfat1$^{-/-}$ joints around 3 months of age.

Results presented herein indicate that the morphological, cellular, and molecular biological changes in and around affected Nfat1$^{-/-}$ articular cartilage vary with the progression of OA. Early pathological changes such as loss of proteoglycans with essentially normal articular structure observed in this animal model are usually not seen in human OA specimens because OA is usually diagnosed in humans in the late stages of the disease. As such, these early stages of the disease have previously not been observed in humans. However, these early morphological and molecular biological alterations are important clues for exploring the mechanisms for the initiation of OA.

The initial loss of proteoglycans and type-II collagen in Nfat1$^{-/-}$ articular cartilage apparently triggers reparative cellular activity with increased expression of cartilage markers in articular cartilage and periarticular tissues. This is consistent with the repair process in human OA. Therefore, expression levels of collagen types-II and -X were up-regulated in Nfat1$^{-/-}$ articular cartilage and periarticular tissues at later disease stages. It is important to point out that type-X collagen is a marker of hypertrophic chondrocytes, which is normally expressed in replacement cartilage in the growth plate during endochondral ossification, and not in persistent cartilage such as articular cartilage. Chondrocyte hypertrophy with up-regulated expression of type-X collagen is also an important feature of human osteoarthritic cartilage. Highly up-regulated expression of type-X collagen in Nfat1$^{-/-}$ articular cartilage supports the diagnosis of OA in the Nfat1$^{-/-}$ mouse joints. However, proliferating and differentiating cartilage cells in the affected Nfat1$^{-/-}$ articular cartilage fail to regenerate deteriorated articular surface, because these cells are not permanent articular chondrocytes in nature. The reparative reactions in periarticular tissues and subchondral bone also fail to rescue the articular destruction. Indeed, periarticular osteophytes and thickened subchondral bone may cause abnormal mechanical loads on the joints and exacerbate the progression of OA. Results presented herein support the concept that OA is not exclusively a disorder of articular cartilage.

Figure 6:
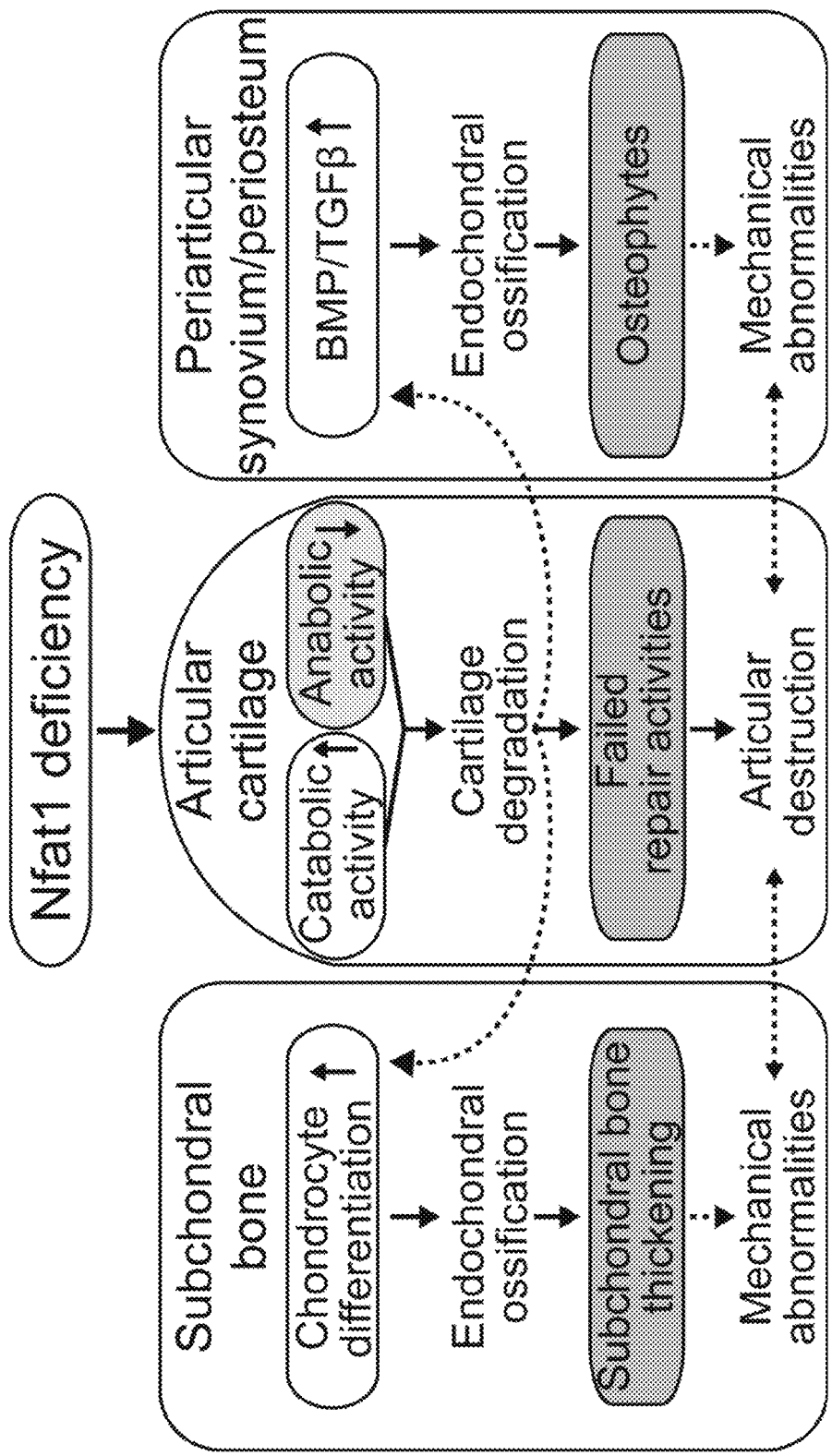
FIG. 6 illustrates a diagram showing possible mechanisms underlying Nfat1 deficiency-induced OA.

FIG. 6 summarizes the mechanism of Nfat1 deficiency-induced articular cartilage degeneration and interactions between articular cartilage and surrounding tissues during the progression of osteoarthritis.

FIGS. 5 and 6 reveal that Nfat1 deficiency initiates dysfunction of articular cartilage cells and degeneration of articular cartilage, which subsequently trigger repair activities in and around affected articular cartilage. These results support the concept that Nfat1 is the primary target for prevention and treatment of Nfat1 deficiency-induced osteoarthritis.

OA is a major worldwide public health issue causing chronic disability. Although many OA-like experimental models have been developed and a number of risk factors proposed to be involved in the pathogenesis of OA, the root causes of primary OA have remained unclear until now. Recent animal and human subject studies have shown that production of matrix-degrading proteinases such as MMP13 and ADAMTS4-5 and specific proinflammatory cytokines such as IL-1β in articular cartilage probably contribute to the pathogenesis of OA. However, clinical trials applying proteinase/cytokine inhibitors for the treatment of OA have been unsuccessful because of insufficient efficiency, turning the attention of researchers to more upstream factors of the cytokines and proteinases in articular chondrocytes.

Findings presented herein demonstrate for the first time that Nfat1 is a key transcription factor regulating the expression of specific cartilage-degrading proteinases and proinflammatory cytokines in adult articular chondrocytes. Nfat1 deficiency causes OA due to dysfunction of adult articular chondrocytes, leading to articular cartilage degradation and repair activities in and around articular cartilage. These results provide new insights into the etiopathogenesis of primary OA. Nfat1 may prove to be a suitable target for the development of new drugs for the prevention and treatment of OA.

EXAMPLES

The following examples are provided to illustrate embodiments of the prevention and are not intended to be limiting. Accordingly, some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the Nfat1 knockout mice (i.e., Nfat1$^{-/-}$), Nfat1 deficient mice (e.g., Nfat1$^{+/-}$), Nfat1 knockdowns, antigens, immunogens, and antibodies prepared in accordance with the present invention.

Example 1

Mouse and Human Nfat1 cDNA and Protein Sequences

The cDNA sequence of mouse Nfat1 is (SEQ ID NO: 2)

```
aggagtggga gcacggggag ccagagcccc ggagcggagc ctaggcgctg cagcgtctgc gccgctccgc cagatcacag cacacggtcc ccagcctgct gatcccggcg cctacagatg cagcgccccg cattgcgcag gccgggcccc cgccagcccc tccgcaccat ggggtctgcg gaccgagaac ctctccaata atgtcacctc gaaccagcct cgccgaggac agctgcctgg gccgacactc gcccgtgccc cgtccggcat cccgctcctc ctcacccggt gccaagcgga ggcattcgtg cgcagaggct ttggttgctc ctctgcccgc agcctcaccc cagcgctccc ggagcccctc gccacagccc tcgcctcacg tggcactgca ggacgacagc atccccgctg ggtacccccc cacggccggc tctgctgttc tcatggatgc cctcaacacc ctggccaccg actcgccctg cgggatcccc tccaagatat ggaagaccag tcctgacccg acgcctgtgt ccaccgctcc gtccaaggct ggcctggccc gccacatcta ccctactgtg gagttcctgg ggccatgtga gcaggaggag aggaggaatt ccgctccaga gtccatcctg ctggtaccac ctacttggcc caagcagttg gtgccggcca ttcccatctg cagcatccct gtgactgcat ccctcccacc actcgagtgg ccactctcca atcagtcggg ctcctatgag ctacggattg aggtccaacc caagccccat caccgggccc actatgagac ggagggcagc cgtggcgctg tcaaagcccc aacaggagga caccctgtgg tgcagctcca cggctacatg gagaacaagc ctctggggct tcagatcttc attgggacag cagatgagag gatccttaag ccgcacgcct tctaccaagt acacaggatc actgggaaaa cggtcaccac cacgagctat gagaagatcg taggcaacac caaggtcctg gagatccccc tggagccaaa gaacaacatg agagccacca tcgactgtgc aggcatcctg aagctccgaa acgctgacat cgagctgcgg aagggcgaga cggacatcgg caggaagaac acgcgtgtgc gcctggtgtt ccgcgtgcac gtcccagagc ccagtgggcg catcgtctcc ctgcaggctg cgtccaaccc catcgagtgc tctcagcgct ctgcccacga gctgccatg tggagagac aagacatgga cagctgcctg gtctacgggg gccagcagat gatcctcacg ggccagaact tcacagcgga gtccaaggtt gtgttcatgg agaagactac aggacctgca gggacctgtg agactcggcc tttgcccatc tctctgatct
```

-continued

```
cagctgaccg cctcccccc tggctttccc ggctgcagag aaaccctcct ggctctgtct
tcagatgctc cgtgctcctt cctgcccag gatcttcgct tgtgctgctg gctctgtaac
attctgccct tgttccctcg catactgtgt ctcctcttac tgggaagcca ttctccctga
gtggtgttcg cgttcaaagg ctcatggctc aactgtccag cccaatgtca ctttttgcct
gtcccttttc cacgctttat tctccaggtg acactcagtg tttcacctgt ctgtctgctc
tctcttgggt cctctggttc ccatactaga ctgtcggttc cttgggagca gggatacact
gtttgctgct gcactcacaa ttatagaatt atctctgtgc gtactaagtg tgcatgtgtc
atgctgaagg aaagcggtgt tcccccttt attgcctctc ccaccatgag aagcggctgt
attatcccca ttttacagat aagttgaggt tcaaagctat caagccagag accctgggtt
agcccctcca actggggaaa gatctggaac cccagcatgt cattttcctg atctctggag
tgatttctct tgtcatgtca aagagaagtc aagaggatag ttctgttcct gtgtgttcta
caaaataaaa gatgcatagc cttcaaggga aggtcaggct gggaggccag gctgttcctg
ccctcgctgg gaaccctggc ccctggcccc tggccctgag cagagtcggg ggtcccagca
aaacattgca aaacaggaaa aaatctaagg acacaaaaac acaagccgtg tggttgagga
gacagggttg ccatggctcc aggcgactct cgaggctggc gtgatccagt gttttggaag
gttcctccat gtgacacagg gttttggaat tcttcagctg gtaagtcctt cttaattcag
gcccctagcc ctggccaagc cactcccggg ctctcggtgt cccgcggggg cgtagactgg
acacaggccc acatcaaatt actcagctct acaactaaaa gttttttgaag cgggtttctt
gttttgttgg atggttttct tggctcggtc tgatggcaga ggctcccatc acctgtcggg
aaggcaaatt gatttttttt tttcaagagg aggcgtgggt ggtggaattc ccttttaacc
gatgagtcac cgagggcagc cgtgactcac tttattattc ccaggttccc aaaggctata
tcgcttttgg gctttgttta ataaatagaa tcatgtatgc gc
```

The corresponding protein sequence of mouse Nfat1 is (SEQ ID NO: 3):

```
MSPRTSLAEDSCLGRHSPYTRPASRSSSPGAKRRHSCAEALVAPLPAASPQRSRSPSPQPSPHVALQDDS
IPAGYPPTAGSAVLMDALNTLATDSPCGIPSKIWKTSPDPTPVSTAPSKAGLARHIYPTVEFLGPCEQEE
RRNSAPESILLVPPTWPKQLVPAIPICSIPVTASLPPLEWPLSNQSGSYELRIEVQPKPHHRAHYETEGS
RGAVKAPTGGHPVVQLHGYMENKPLGLQIFIGTADERILKPHAFYQVHRITGKTVTTTSYEKIVGNTKVL
EIPLEPKNNMRATIDCAGILKLRNADIELRKGETDIGRKNTRVRLVFRVHVPEPSGRIVSLQAASNPIEC
SQRSAHELPMVERQDMDSCLVYGGQQMILTGQNFTAESKVVFMEKTTGPAGTCETRPLPISLISADRLSP
WLSRLQRNPPGSVFRCSVLLPAPGSSLVLLAL
```

The cDNA sequence of human Nfat1 is (SEQ ID NO: 4):

```
agcaggaagc tcgcgccgcc gtcgccgccg ccgctcagct tccccgggcg cgtccaggac
ccgctgcgcc aggcgcgccg tccccggacc cggcgtgcgt ccctacgagg aaagggaccc
cgccgctcga gccgcctccg ccagcccac tgcgaggggt cccagagcca gccgcgcccg
ccctcgcccc cggccccgca gccttcccgc cctgcgcgcc atgaacgccc ccgagcggca
gccccaaccc gacggcgggg acgcccagg ccacgagcct ggggcagcc cccaagacga
gcttgacttc tccatcctct tcgactatga gtatttgaat ccgaacgaag aagagccgaa
tgcacataag gtcgccagcc ccccctccgg acccgcatac cccgatgatg tcctggacta
```

-continued

```
tggcctcaag ccatacagcc cccttgctag tctctctggc gagcccccg gccgattcgg agagccggat agggtagggc cgcagaagtt tctgagcgcg gccaagccag cagggccctc gggcctgagc cctcggatcg agatcactcc gtcccacgaa ctgatccagg cagtggggcc cctccgcatg agagacgcgg gcctcctggt ggagcagccg ccctggccg gggtggccgc cagcccgagg ttcaccctgc ccgtgcccgg cttcgagggc taccgcgagc cgctttgctt gagccccgct agcagcggct cctctgccag cttcatttct gacaccttct cccctacac ctcgccctgc gtctcgccca ataacggcgg gcccgacgac ctgtgtccgc agtttcaaaa catccctgct cattattccc ccagaacctc gccaataatg tcacctcgaa ccagcctcgc cgaggacagc tgcctgggcc gccactcgcc cgtgccccgt ccggcctccc gctcctcatc gcctggtgcc aagcggaggc attcgtgcgc cgaggccttg gttgccctgc cgcccggagc ctcaccccag cgctcccgga gcccctcgcc gcagccctca tctcacgtgg caccccagga ccacggctcc ccggctgggt accccctgt ggctggctct gccgtgatca tggatgccct gaacagcctc gccacggact cgccttgtgg gatccccccc aagatgtgga agaccagccc tgacccctcg ccggtgtctg ccgccccatc caaggccggc ctgcctcgcc acatctaccc ggccgtggag ttcctggggc cctgcgagca gggcgagagg agaaactcgg ctccagaatc catcctgctg gttccgccca cttggcccaa gccgctggtg cctgccattc ccatctgcag catcccagtg actgcatccc tccctccact tgagtggccg ctgtccagtc agtcaggctc ttacgagctg cggatcgagg tgcagcccaa gccacatcac cgggcccact atgagacaga aggcagccga ggggctgtca agctccaac tggaggccac cctgtggttc agctccatgg ctacatggaa aacaagcctc tgggacttca gatcttcatt gggacagctg atgagcggat ccttaagccg cacgccttct accaggtgca ccgaatcacg gggaaaactg tcaccaccac cagctatgag aagatagtgg gcaacaccaa agtcctggag ataccctg agcccaaaaa caacatgagg gcaaccatcg actgtgcggg gatcttgaag cttagaaacg ccgacattga gctgcggaaa ggcgagacgg acattggaag aaagaacacg cgggtgagac tggttttccg agttcacatc ccagagtcca gtggcagaat cgtctctta cagactgcat ctaaccccat cgagtgctcc cagcgatctg ctcacgagct gcccatggtt gaaagacaag acacagacag ctgcctggtc tatggcggcc agcaaatgat cctcacgggg cagaacttta catccgagtc caaagttgtg tttactgaga agaccacaga tggacagcaa atttgggaga tggaagccac ggtggataag gacaagagcc agcccaacat gcttttgtt gagatccctg aatatcggaa caagcatatc cgcacacctg taaaagtgaa cttctacgtc atcaatggga agagaaaacg aagtcagcct cagcactta cctaccaccc agtcccagcc atcaagacgg agcccacgga tgaatatgac cccactctga tctgcagccc cacccatgga ggcctgggga gccagcctta ctaccccag cacccgatgg tggccgagtc ccctcctgc ctcgtggcca ccatggctcc ctgccagcag ttccgcacgg ggctctcatc ccctgacgcc cgctaccagc aacagaaccc agcggccgta ctctaccagc ggagcaagag cctgagcccc agcctgctgg gctatcagca gccggccctc atggccgccc cgctgtccct tgcggacgct caccgctctg tgctggtgca cgccggctcc cagggccaga gctcagccct gctccacccc tctccgacca accagcaggc ctcgcctgtg atccactact cacccaccaa ccagcagctg cgctgcggaa gccaccagga gttcagcac atcatgtact gcgagaattt cgcaccaggc accaccagac ctggcccgcc cccggtcagt caaggtcaga ggctgagccc gggttcctac cccacagtca ttcagcagca
```

```
-continued
gaatgccacg agccaaagag ccgccaaaaa cggacccccg gtcagtgacc aaaaggaagt attacctgcg ggggtgacca ttaaacagga gcagaacttg gaccagacct acttggatga tgttaatgaa attatcagga aggagttttc aggacctcct gccagaaatc agacgtaaaa gaagccatta tagcaagaca ccttctgtat ctgaccoctc ggagccctcc acagccctc accttctgtc tcctttcatg ttcatctccc agcccggagt ccacacgcgg atcaatgtat gggcactaag cggactctca cttaaggagc tcgccacctc cctcta
```

The corresponding protein sequence of human Nfat1 is (SEQ ID NO: 5):

```
MNAPERQPQPDGGDAPGHEPGGSPQDELDFSILFDYEYLNPNEEEPNAHKVASPPSGPAYPDDVLDYGLK

PYSPLASLSGEPPGRFGEPDRVGPQKFLSAAKPAGASGLSPRIEITPSHELIQAVGPLRMRDAGLLVEQP

PLAGVAASPRFTLPVPGFEGYREPLCLSPASSGSSASFISDTFSPYTSPCVSPNNGGPDDLCPQFQNIPA

HYSPRTSPIMSPRTSLAEDSCLGRHSPVPRPASRSSSPGAKRRHSCAEALVALPPGASPQRSRSPSPQPS

SHVAPQDHGSPAGYPPVAGSAVIMDALNSLATDSPCGIPPKMWKTSPDPSPVSAAPSKAGLPRHIYPAVE

FLGPCEQGERRNSAPESILLVPPTWPKPLVPAIPICSIPVTASLPPLEWPLSSQSGSYELRIEVQPKPHH

RAHYETEGSRGAVKAPTGGHPVVQLHGYMENKPLGLQIFIGTADERILKPHAFYQVHRITGKTVTTTSYE

KIVGNTKVLEIPLEPKNNMRATIDCAGILKLRNADIELRKGETDIGRKNTRVRLVFRVHIPESSGRIVSL

QTASNPIECSQRSAHELPMVERQDTDSCLVYGGQQMILTGQNFTSESKVVFTEKTTDGQQIWEMEATVDK

DKSQPNMLFVEIPEYRNKHIRTPVKVNFYVINGKRKRSQPQHFTYHPVPAIKTEPTDEYDPTLICSPTHG

GLGSQPYYPQHPMVAESPSCLVATMAPCQQFRTGLSSPDARYQQQNPAAVLYQRSKSLSPSLLGYQQPAL

MAAPLSLADAHRSVLVHAGSQGQSSALLHPSPTNQQASPVIHYSPTNQQLRCGSHQEFQHIMYCENFAPG

TTRPGPPPVSQGQRLSPGSYPTVIQQQNATSQRAAKNGPPVSDQKEVLPAGVTIKQEQNLDQTYLDDVNE

IIRKEFSGPPARNQT
```

Example 2

Animals

The method for generation of Nfat1-deficient mice was previously described by Hodge et al, Immunity, 1996, 4:397-405. Nfat1$^{-/-}$, Nfat1$^{+/-}$, and WT mice used in this study were bred and maintained in the Laboratory Animal Resources facility at the University of Kansas Medical Center (KUMC). All animal procedures were performed with the approval of the Institutional Animal Care and Use Committee at KUMC in compliance with all federal and state laws and regulations.

Example 3

Histology, Histochemistry, and Immunohistochemistry

Mouse joint tissue samples were fixed in 2% paraformaldehyde, decalcified in 25% formic acid, and embedded in either paraffin or JB-4 plastic medium (Polysciences). Safranin-O, Alcian blue, and toluidine blue stains were utilized to identify cartilage cells and matrices. 10% EDTA-decalcified tissue sections were used for immunohistochemical staining. To observe both immunoreaction and cellular morphology, some tissue sections were stained by the avidin-biotin peroxidase complex methods. AEC or DAB chromogen was used for color detection. At least five Nfat1$^{-/-}$ and WT mice were evaluated at each time point.

Example 4

RNA Isolation and Gene Expression Analyses by Quantitative Real-Time PCR (qPCR)

Since the early OA-like phenotype first occurs in the femoral heads of Nfat1$^{-/-}$ female mice and femoral head articular cartilage is thicker and more capable of being removed compared to other joints, female femoral head articular cartilage and periarticular tissues were collected for RNA isolation. Articular cartilage samples were dissected under a surgical microscope to obtain articular cartilage without visible contamination of subchondral bone or soft tissues. Freshly dissected tissues harvested from mice and human joints were collected in "RNAlater" solution (Ambion) at 4° C., homogenized in TRIzol reagent (Invitrogen), and treated with an RNeasy Mini Kit (Qiagen) and a DNA Digestion Kit (Ambion) to obtain purified RNA. For total RNA isolation from mice and human blood, whole blood samples were homogenized in TRIzol solution (Invitrogen) and treated with an RNeasy Mini Kit (Qiagen) to remove proteoglycan contamination and a DNA Digestion Kit (Ambion) to remove DNA. One µg of total RNA and a "RETROScript" kit (Ambion) were used for reverse transcription to yield cDNA. "Primer Express 3.0" software (Applied Biosystems) was used to design specific primers of target genes used in this study, which are presented in Table 1. qPCR reactions were performed in triplicate in 96-well plates using a 7500 Real-Time PCR system (Applied Biosystems) under standard conditions recommended by the manufacturer. "SYBR Green" was used for detection. Primers for rodent Gapdh (glyceraldehyde-3-phosphate dehydrogenase, Applied Biosystems) were used as internal controls. Expression levels of target genes in the tissues/cells of WT and Nfat1$^{-/-}$ mice were quantified using the $2^{-\Delta\Delta Ct}$ relative quantification methods.

TABLE 1

Specific primers used for quantitative real-time RT-PCR

| Gene | Forward | Reverse |
|---|---|---|
| Mapk1 | TTTGGTCTGTGGGCTGCAT (SEQ ID NO: 6) | TCCTGGGAAGATAGGCCTGTT (SEQ ID NO: 7) |
| Mapk9 | TTTGGTATGACCCCGCTGAA (SEQ ID NO: 8) | CTTTCTTCCAACTGGGCATCA (SEQ ID NO: 9) |
| Mmp1a | CCTCGTTGGACCAAAACACA (SEQ ID NO: 10) | GCGATGGCATCTTCCACAA (SEQ ID NO: 11) |
| Mmp3 | TCCTGATGTTGGTGGCTTCA (SEQ ID NO: 12) | CACACTCTGTCTTGGCAAATCC (SEQ ID NO: 13) |
| Mmp8 | CAGGGAGAAGCAGACATCAACA (SEQ ID NO: 14) | GCATGGGCAAGGATTCCAT (SEQ ID NO: 15) |
| Mmp9 | GCCTCAAGTGGGACCATCAT (SEQ ID NO: 16) | CTCGCGGCAAGTCTTCAGA (SEQ ID NO: 17) |
| Mmp13 | TCACCTGATTCTTGCGTGCTA (SEQ ID NO: 18) | CAGATGGACCCCATGTTTGC (SEQ ID NO: 19) |
| Timp1 | GCAACTCGGACCTGGTCATAA (SEQ ID NO: 20) | CTGGTATAAGGTGGTCTCGTTGATT (SEQ ID NO: 21) |
| Adamts4 | ACCCGGCAGGACCTGTGT (SEQ ID NO: 22) | CCAGTTCATGAGCAGCAGTGA (SEQ ID NO: 23) |
| Adamts5 | GCTGCTGGTAGCATCGTTACTG (SEQ ID NO: 24) | GAGTGTAGCGCGCATGCTT (SEQ ID NO: 25) |
| Acan | TGGGATCTACCGCTGTGAAGT (SEQ ID NO: 26) | CTCGTCCTTGTCACCATAGCAA (SEQ ID NO: 27) |
| Col2α1 | CGAGATCCCCTTCGGAGAGT (SEQ ID NO: 28) | TGAGCCGCGAAGTTCTTTTC (SEQ ID NO: 29) |
| Col9α1 | TCTTAAGCGTCGTGCAAGATTTC (SEQ ID NO: 30) | CTTGGGACACAGTTCACTTCCA (SEQ ID NO: 31) |
| Col10α1 | TTATGCTGAACGGTACCAAACG (SEQ ID NO: 32) | TGGCGTATGGGATGAAGTATT (SEQ ID NO: 33) |
| Col11α1 | CACAAAACCCCTCGATAGAAGTG (SEQ ID NO: 34) | CCTGTGATCAGGAACTGCTGAA (SEQ ID NO: 35) |
| Ctnnb1 | ACACCTCCCAAGTCCTTTATGAAT (SEQ ID NO: 36) | CCCGTCAATATCAGCTACTTGCT (SEQ ID NO: 37) |
| Sox9 | TCTGGAGGCTGCTGAACGA (SEQ ID NO: 38) | TCCGTTCTTCACCGACTTCCT (SEQ ID NO: 39) |
| IL1b | GCTTCCTTGTGCAAGTGTCTGA (SEQ ID NO: 40) | TCAAAAGGTGGCATTTCACAGT (SEQ ID NO: 41) |
| IL4 | CGGATGCGACAAAAATCACTT (SEQ ID NO: 42) | CCCTTCTCCTGTGACCTCGTT (SEQ ID NO: 43) |
| IL6 | TCGGAGGCTTAATTACACATGTTC (SEQ ID NO: 44) | TGCCATTGCACAACTCTTTTCT (SEQ ID NO: 45) |
| IL10 | GGACCAGCTGGACAACATACTG (SEQ ID NO: 46) | ACCAGGTAAAACTGGATCATTTCC (SEQ ID NO: 47) |
| IL13 | TTGAGGAGCTGAGCAACATCAC (SEQ ID NO: 48) | GCGGCCAGGTCCACACT (SEQ ID NO: 49) |
| IL17a | TCTGTGTCTCTGATGCTGTTGCT (SEQ ID NO: 50) | TCGCTGCTGCCTTCACTGT (SEQ ID NO: 51) |

TABLE 1-continued

Specific primers used for quantitative real-time RT-PCR

| Gene | Forward | Reverse |
|---|---|---|
| IL18 | CTCTTGCGTCAACTTCAAGGAA (SEQ ID NO: 53) | GTGAAGTCGGCCAAAGTTGTC (SEQ ID NO: 54) |
| Tnfa | AGGGATGAGAAGTTCCCAAATG (SEQ ID NO: 55) | GGCTTGTCACTCGAATTTTGAGA (SEQ ID NO: 56) |
| Nfat1 | GTGCAGCTCCACGGCTACAT (SEQ ID NO: 57) | GCGGCTTAAGGATCCTCTCA (SEQ ID NO: 58) |
| Bmp2 | TGTTTGGCCTGAAGCAGAGA (SEQ ID NO: 59) | GCCTGCGGTACAGATCTAGCA (SEQ ID NO: 60) |
| Bmp3b | CAGAGCCATGCTGTGTTCCA (SEQ ID NO: 61) | ACCGCATTCCGATTTTCATC (SEQ ID NO: 62) |
| Bmp4 | TGGGCTGGAATGATTGGATT (SEQ ID NO: 63) | CAGTCCCCATGGCAGTAGAAG (SEQ ID NO: 64) |
| Bmp5 | TTCTTCAAGGCAAGCGAGGTA (SEQ ID NO: 65) | GCGGTTTTGATTTTTCCGTTT (SEQ ID NO: 66) |
| Bmp6 | GCTGAAGTCCGCTCCACTCT (SEQ ID NO: 67) | CCCATCCTCTTCGTCGTCAT (SEQ ID NO: 68) |
| Bmp7 | CTGACGCCGACATGGTCAT (SEQ ID NO: 69) | GGTGGTATCGAGGGTGGAAGA (SEQ ID NO: 70) |
| Bmp8a | TGGTCTGCTTGGACGACAAG (SEQ ID NO: 71) | GCTGGCCCTGAAGAAGGTTA (SEQ ID NO: 72) |
| Bmp9 | CAGCCACTGCCAGAAGACTTC (SEQ ID NO: 73) | CCTTGGGTGCAATGATCCA (SEQ ID NO: 74) |
| Bmp10 | TGGCTGAACTGCGGTTGTAC (SEQ ID NO: 75) | TTACGGTCCACGCCATCATA (SEQ ID NO: 76) |
| Bmp11 | TGCGCCTAGAGAGCATCAAGT (SEQ ID NO: 77) | TACCTCCCGGCTGATGTTG (SEQ ID NO: 78) |
| Bmp12 | CGGGCGTGTGGACACAA (SEQ ID NO:79) | GCTCTGGCCTTGAGTTGCTT (SEQ ID NO: 80) |
| Bmp13 | CTGCGCTGCAGCAGAAAG (SEQ ID NO: 81) | GTCGTCCCAGCCTAACTCCTT (SEQ ID NO: 82) |
| Bmp14 | AACAGCAGCGTGAAGTTGGA (SEQ ID NO: 83) | GGTCATCTTGCCCTTTGTCAA (SEQ ID NO: 84) |
| Bmp15 | ACGATTGGAGCGAAAATGGT (SEQ ID NO: 85) | AACCTCTGGGAGGCCTTACTG (SEQ ID NO: 86) |
| Igf1 | GAGCTGGTGGATGCTCTTCAG (SEQ ID NO: 87) | GCCTGTGGGCTTGTTGAAGT (SEQ ID NO: 88) |
| Tgfb1 | CCGAAGCGGACTACTATGCTAAA (SEQ ID NO: 89) | GTTTTCTCATAGATGGCGTTGTTG (SEQ ID NO: 90) |
| Tgfb2 | CTGTACCTTCGTGCCGTCTAATAA (SEQ ID NO: 91) | TGCCATCAATACCTGCAAATCT (SEQ ID NO: 92) |
| Tgfb3 | CAGTGGAGAAAAATGGAACCAAT (SEQ ID NO: 93) | GTCGAAGTATCTGGAAGAGCTCAAT (SEQ ID NO: 52) |

Example 5

Western Blot

Total protein was isolated from the organic phase following RNA isolation from cells/tissues according to the manufacturer's instructions (Invitrogen). Small aliquots were applied to 4-15% gradient SDS-PAGE, and then transferred to a polyvinylidene difluoride membrane (Hybond P, Amersham Biosciences). After transfer, the membranes were blocked using 5% dry milk in PBS with 0.3% Tween 20 and incubated with specific primary antibodies. Horseradish peroxidase (HRP)-conjugated anti-mouse IgG (Santa Cruz) was used as the secondary antibody. For the loading control, a peptide-affinity purified goat polyclonal antibody against Gapdh (IMGENEX) was used as the primary antibody, and an anti-goat IgG HRP-conjugated antibody (Santa Cruz) was used as the secondary antibody. Bound secondary antibody was detected using chemiluminescent HRP substrate (Millipore).

Example 6

Cell Culture and DNA Transfection

Articular cartilage cells were isolated from the femoral heads of 3-month-old WT and Nfat1$^{-/-}$ female mice using collagenase D (1.5 mg/ml, Roche) in DMEM at 37° C. for 3-4 hours. Primary cells were plated at $2 \times 10^5$ cells per 23-mm diameter culture well in DMEM supplemented with 2 mM L-glutamine, 10% heat-inactivated fetal calf serum, and 1% penicillin/streptomycin, then placed into a humidified incubator with 5% $CO_2$ at 37° C. When cultivated cells reached 70-80% of confluence, the cultures were transduced with lentiviral particles for forced expression of target genes. All cultures were replenished with fresh media three times per week. Packaging plasmid psPAX2 (Addgene), envelope plasmid pMD2.G (Addgene), and highly transfectable 293T cells (ATCC) were used for the production of viral particles.

Example 7

Transgenic Mice Overexpressing Nfat1 in Cartilage

In cartilage-specific transgenic mice, constitutively active-Nfat1 (CA-Nfat1) is specifically expressed in the chondrocyte lineage cells including articular cartilage cells.

CA-Nfat1 cDNA tagged with an HA epitope in pENTR vector (Addgene, plasmid 11792) is inserted into pCol2a1 construct which contains Col2a1 promoter that can drive cartilage specific expression (Zhou et al., J Cell Sci 1995; 108:3677-84). Unique SpeI restriction site in pCol2a1 construct is used with Getaway Vector Conversion System (Invitrogen) to convert it into destination vector compatible with LR reaction used in Getaway cloning strategy. This reaction between CA-Nfat1 cDNA in pENTR vector and converted pCol2a1 leads to final plasmid with CA-Nfat1 cDNA with an HA-tag driven by cartilage-specific Col2a1 promoter-enhancer. NotI restriction site in CA-Nfat1 cDNA is eliminated by site-directed mutation using a QuickChange Site Directed Mutagenesis Kit (Stratagen). This mutation allows us to remove plasmid backbone by restriction digestion using NotI in final construct. Transgenic mice are generated by pronuclear injection of Col2a1-CA-Nfat1 cDNA with FVB strain mice. Genomic DNA isolated from the tails of these mice is analyzed by PCR and Southern blot analysis using specific primers and probes for the transgene. Expression of the transgene in articular cartilage is confirmed by real-time qPCR analysis. The founder transgenic mice on FVB background are then crossed with the Nfat1$^{-/-}$ mice on BALB/c background to examine whether overexpression of CA-Nfat1 can rescue the osteoarthritis phenotypes of Nfat1$^{-/-}$ mice. In addition, the FVB founder mice are backcrossed onto BALB/c background for 12 generations to generate cartilage-specific BALB/c congenic mice to facilitate a comparative analysis with the Nfat1$^{-/-}$ mice on the same genetic background.

It has been reported herein that early osteoarthritis phenotypes occurs in young adult Nfat1$^{-/-}$ mice and older NFAT$^{+/-}$ and Nfat1 wild type mice. Age-related changes in expression levels of Nfat1 or Nfat1 isoforms have been determined by qPCR analysis in mouse blood and articular cartilage and found that low levels of Nfat1 activity are predictive of the onset of osteoarthritis in NFAT$^{+/-}$ and Nfat1 wild type mice. Based on these observations, the cartilage-specific Nfat1 transgenic mice can be used for testing whether the onset of osteoarthritis is prevented or delayed in Nfat1 transgenic mice in which Nfat1 expression levels are not reduced in articular cartilage of older animals.

Currently, efforts to repair damaged articular cartilage face major obstacles due to the limited intrinsic repair capacity of the tissue. Animal and human studies have demonstrated that a full thickness defect of articular cartilage penetrated through the subchondral bone to the bone marrow spaces can be repaired morphologically through the proliferation and differentiation of bone marrow stem cells into cartilage cells which synthesize a cartilage matrix, or by implanting chondrocyte-seeded biomaterials with or without growth factors using tissue engineering technology. However, the repaired articular cartilage tissue degenerates with reduced expression levels of cartilage markers after 3-6 month, and the joints with articular cartilage lesions eventually develop osteoarthritis. We have recently discovered that Nfat1 is critical for maintaining normal anabolic activity of adult articular cartilage cells in mice. Based on these observations, the cartilage-specific Nfat1 transgenic mice can be used for testing: 1) whether the rate of articular cartilage repair of surgically created articular cartilage defects in the Nfat1 transgenic mice is increased compared to wild type mice; 2) whether the expression levels of cartilage makers in repair articular cartilage of the Nfat1 transgenic mice are more stable for longer period of time than similar defects created in wild type mice; 3) whether the onset of osteoarthritis in the joints with articular cartilage defects of the Nfat1 transgenic mice are prevented or delayed compared to wild type mice; and 4) The founder transgenic mice can be crossed with the Nfat1$^{-/-}$ mice to examine whether overexpression of CA-Nfat1 can rescue the osteoarthritis phenotypes of Nfat1$^{-/-}$ mice.

Example 8

Preparation of an Nfat1 Knockdown System

In one embodiment, the present invention includes an articular cartilage cell line that expresses Nfat1. An articular cartilage cell line according to the present invention includes a plurality of articular cartilage cells that excrete type II collagen and/or aggrecan, and at least one siRNA that is inserted in the plurality of cells, wherein the siRNA reduces expression of Nfat1.

Figure 7A:
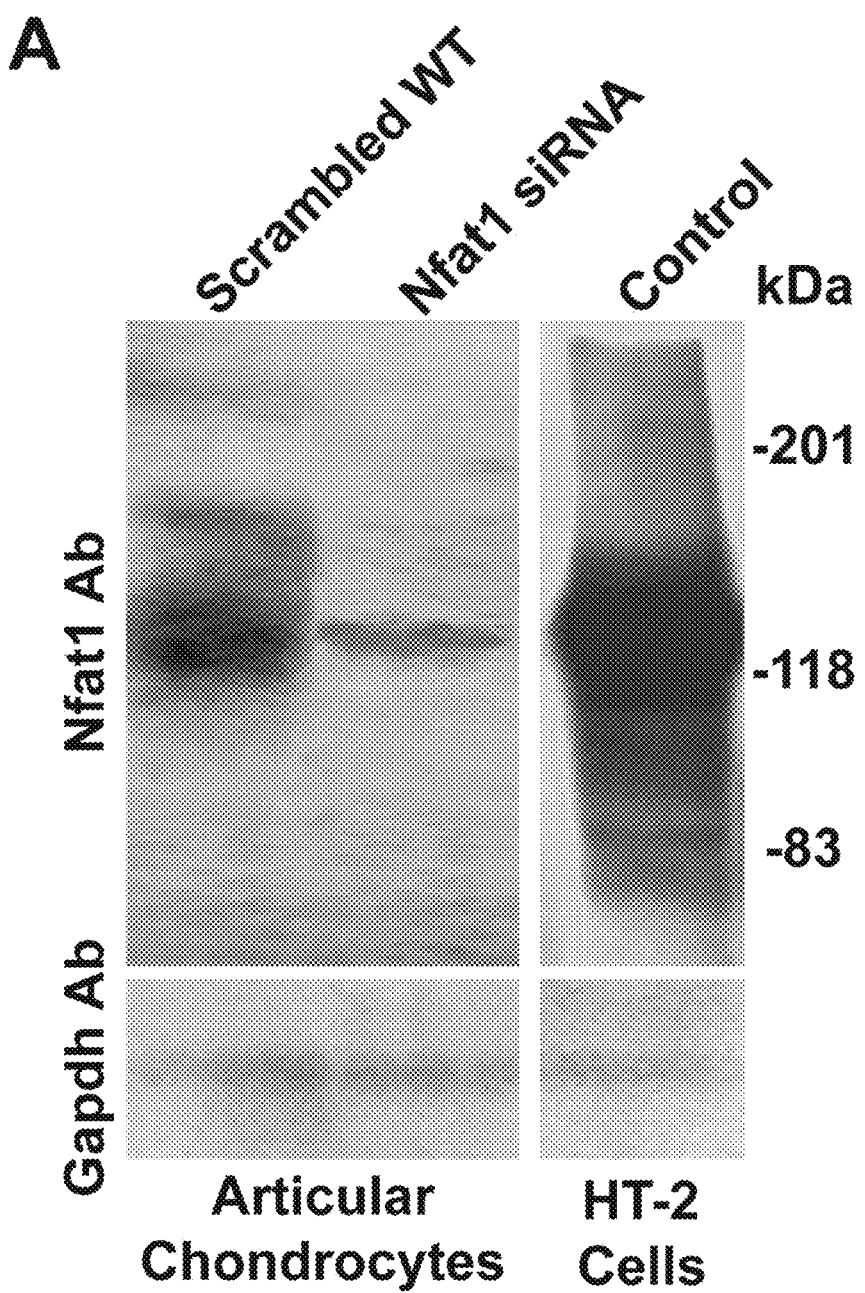
FIG. 7A illustrates Western blots using Nfat1 antibody (Ab) and Gapdh Ab (loading control) to confirm that knockdown of Nfat1 expression by siRNA delivered with lentiviral vectors substantially reduces the synthesis of Nfat1 protein in cultured primary articular chondrocytes isolated from 3-month old WT femoral head articular cartilage; Nfat1 protein extracted from HT-2 cells is used as a positive control.
Figure 7B:
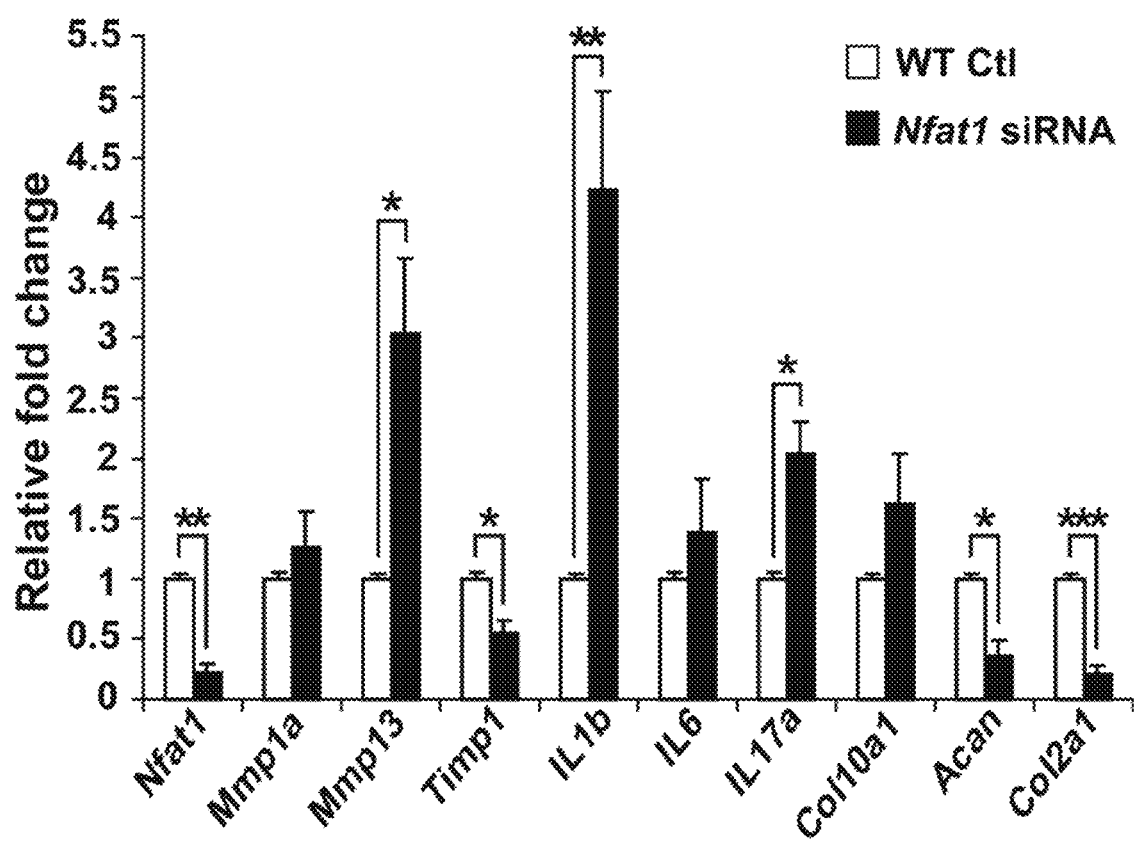
FIG. 7B illustrates qPCR analyses showing that knockdown of Nfat1 expression by siRNA significantly reduces Nfat1, Timp1, Acan, and Col2a1 expression and elevates Mmp13, IL1b, and IL17α expression.
Figure 8A:
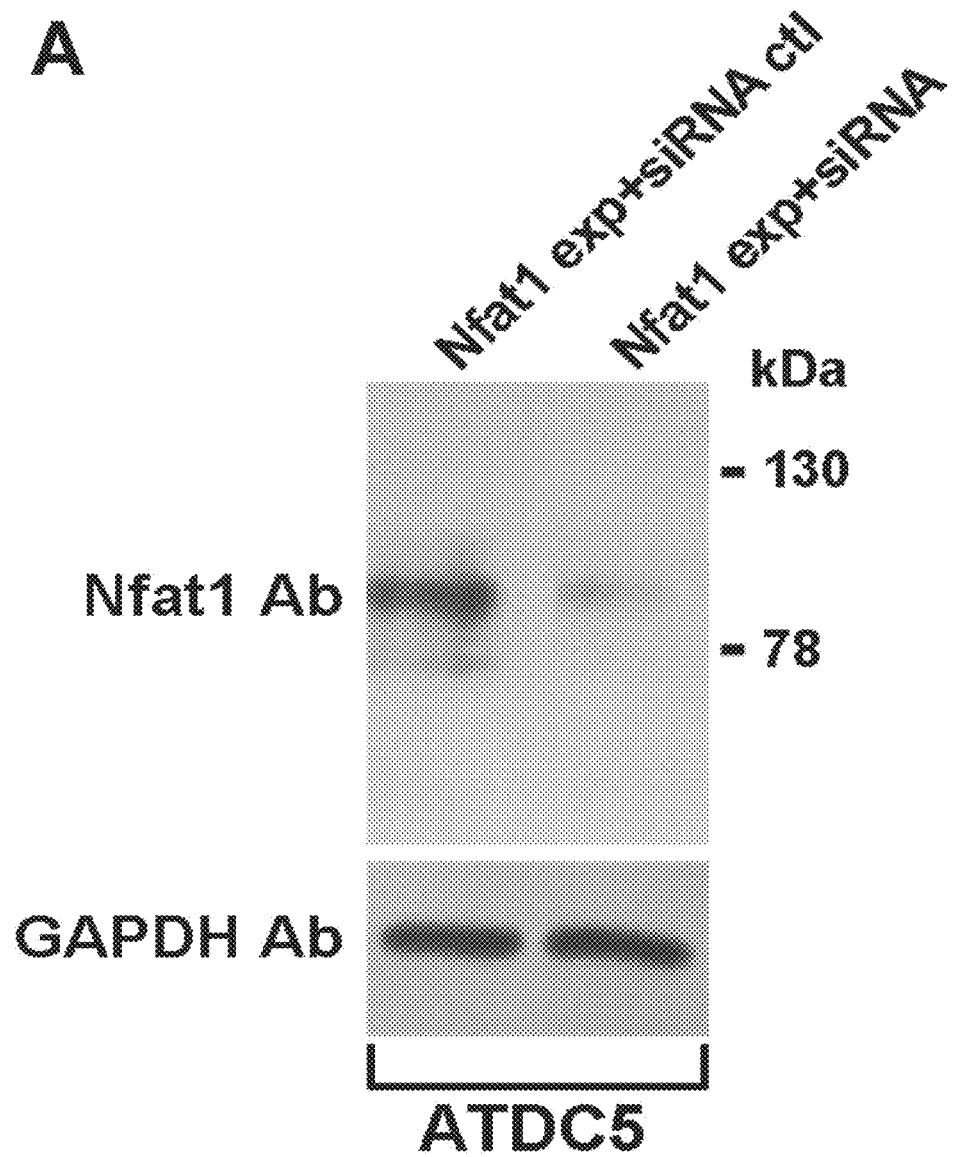
FIG. 8A illustrates Western blots using Nfat1 antibody (Ab) and Gapdh Ab (loading control) to confirm that knockdown of Nfat1 expression by siRNA delivered with lentiviral vectors substantially reduces the synthesis of Nfat1 protein in cultured ATDC5 chondrogenic cells.
Figure 8B:
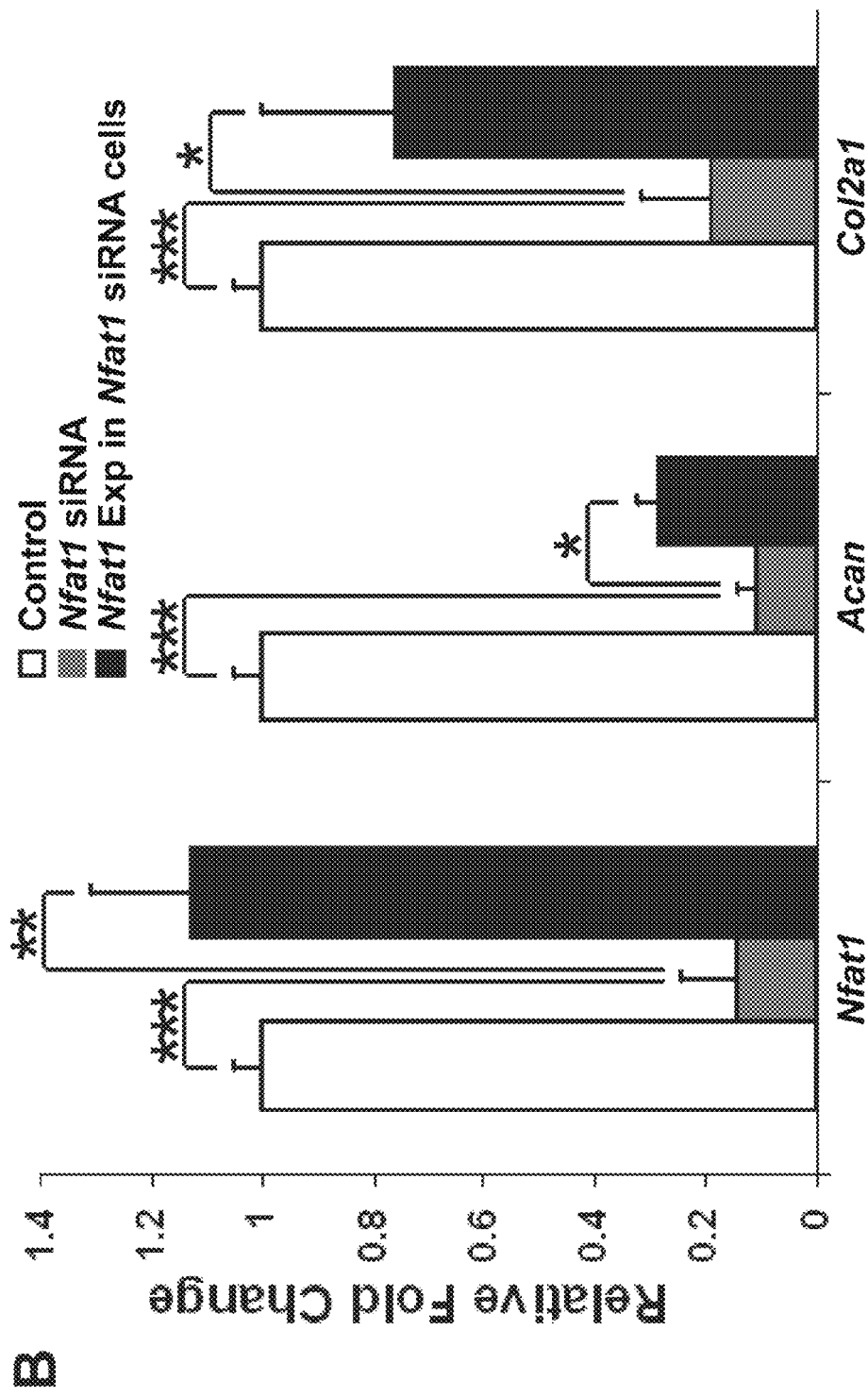
FIG. 8B illustrates qPCR analyses demonstrating relative fold change in mRNA expression of Nfat1, aggrecan (Acan), and type-II collagen (Col2α1) 6 days after transfection; Nfat1 siRNA significantly suppresses the expression of Nfat1 and cartilage marker genes; Nfat1 expression level is completely recovered by forced Nfat1 expression, while aggrecan and type-II collagen levels are partially, but significantly, recovered in comparison to the NFAT1 siRNA group without forced Nfat1 expression; Control=insulin-treated normal ATDC5 cells; Nfat1 siRNA=Nfat1 siRNA in insulin-treated ATDC5 cells; Nfat1 Exp in Nfat1 siRNA cells=Forced expression of Nfat1 in Nfat1 siRNA and insulin-treated ATDC5 cells.
Figure 9A:
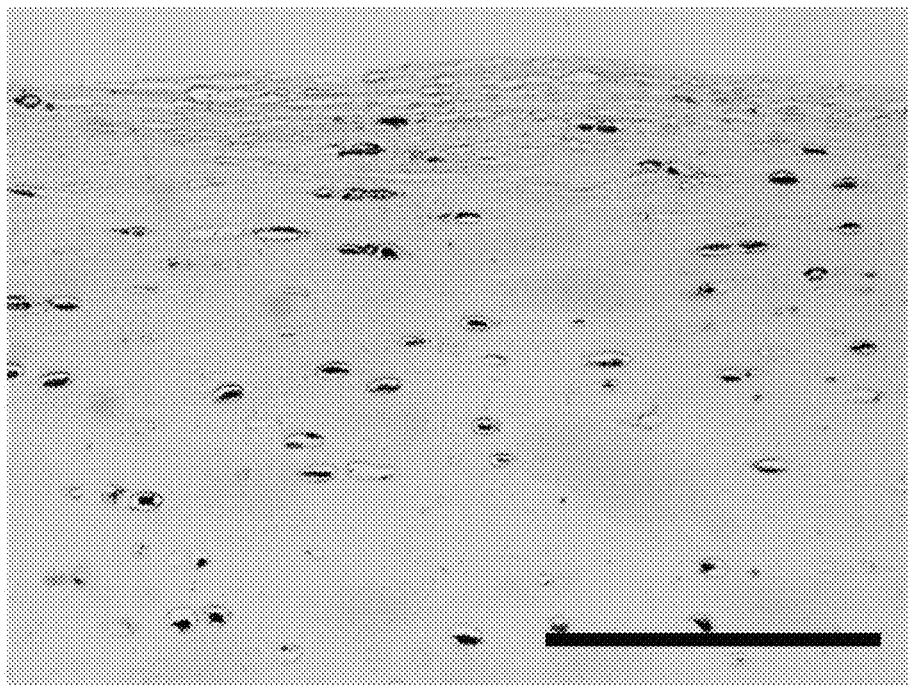
FIG. 9A illustrates immunohistochemical staining using NFAT1 (NFATc2)-specific antibody showing Nfat1 expression in normal human articular cartilage (dark staining) in the majority of articular cartilage cells.
Figure 9B:
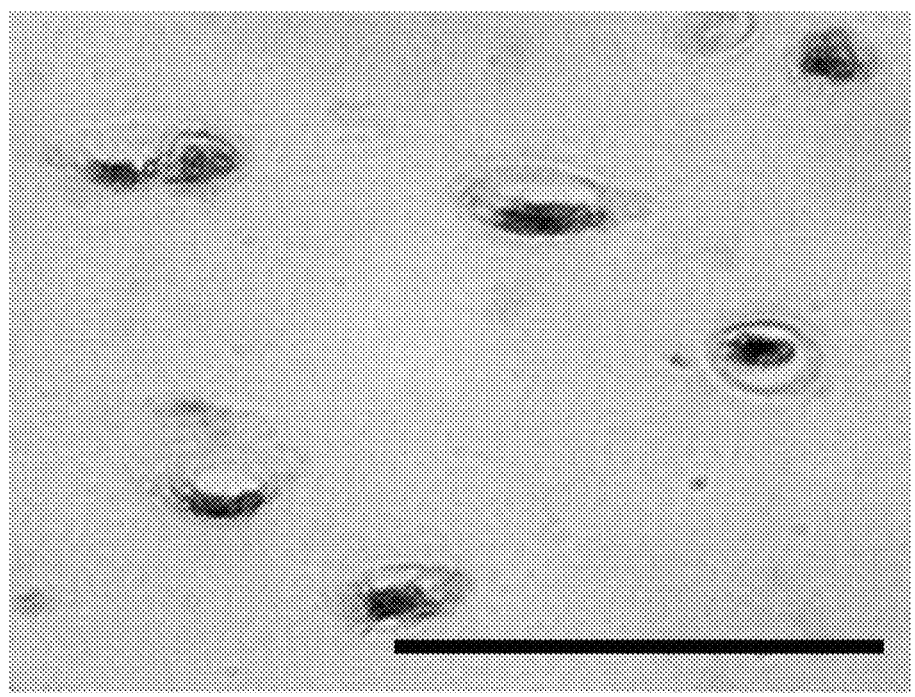
FIG. 9B illustrates high magnification of the cells shown on FIG. 9A.
Figure 9C:
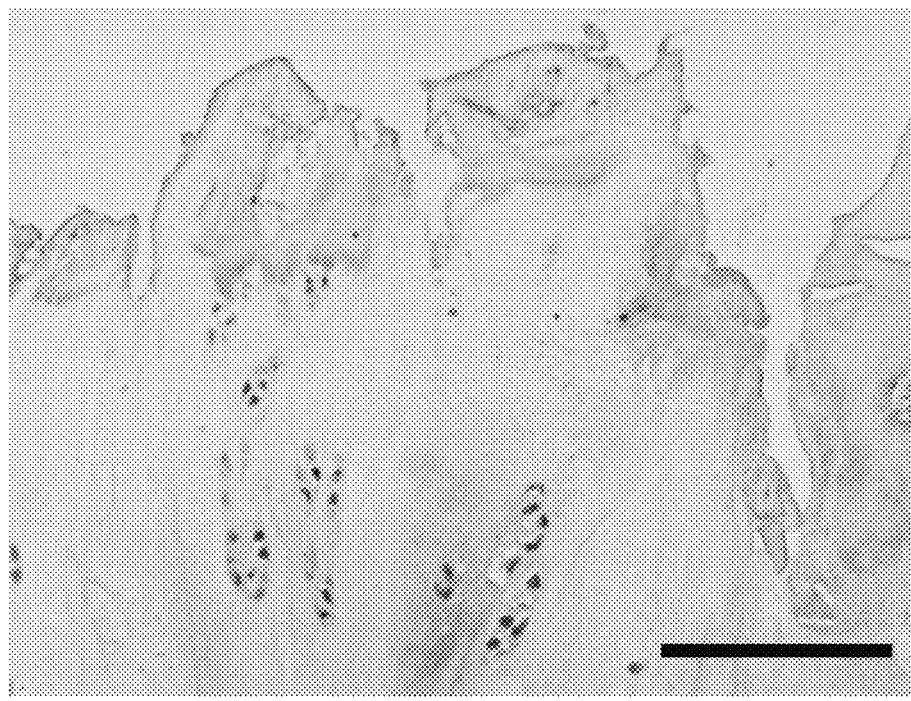
FIG. 9C illustrates that immunohistochemical staining using NFAT1 (NFATc2)-specific antibody failed to detect significant Nfat1 expression in osteoarthritic articular cartilage revealing that NFAT1 protein expression is substantially decreased in articular cartilage cells of human osteoarthritic joints compared to articular cartilage cells in normal control human joints; loss of Nfat1 expression is associated with articular destruction with fissuring and chondrocyte clustering, which are typical features of human OA.
Figure 9D:
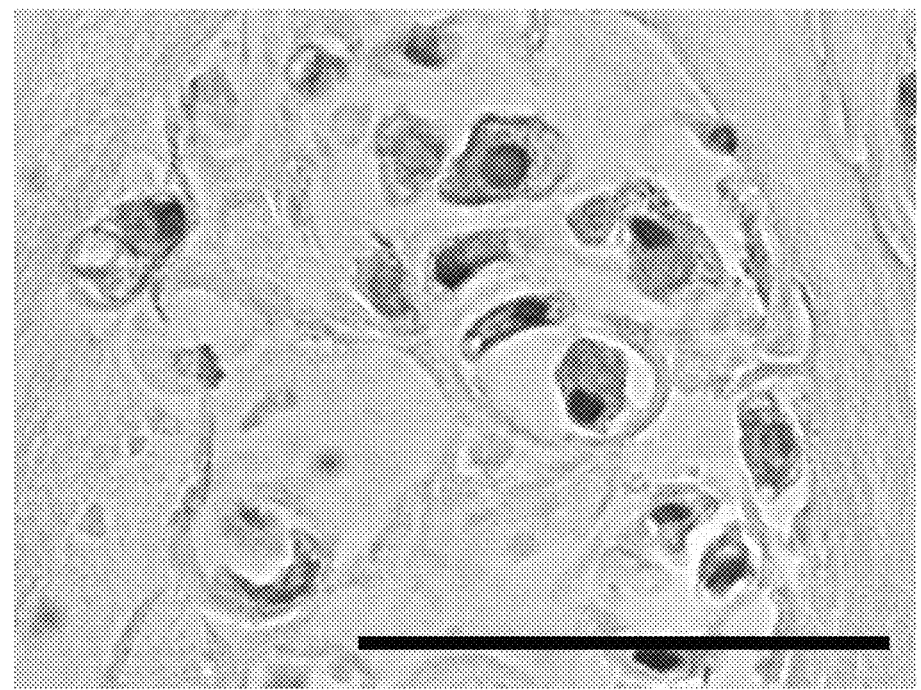
FIG. 9D illustrates high magnification of human osteoarthritic cells with no detectable immunoreaction to NFAT1 antibody.

An example of an Nfat1 siRNA sequence is GAC-TAT-CTG-AAC-CCT-ATC-G (SEQ ID NO: 1). Preferably, the siRNA reduces Nfat1 expression by at least 50% relative to wild type cells. More preferably, the siRNA reduces Nfat1 expression by at least 75% relative to wild type cells. Even more preferably, the siRNA reduces Nfat1 expression by at least 90% relative to wild type cells. Most preferably, the siRNA reduces Nfat1 expression by at least 99% relative to wild type cells. FIGS. 7A and 8A demonstrate that Nfat1 expression can be "knocked down" by siRNA in cultured mouse articular chondrocytes and ATDC5 chondrogenic cell line and that knock down of Nfat1 expression affects the expression of the downstream effectors of Nfat1 (FIGS. 7B and 8B).

In order to knock down expression of Nfat1 in wild-type articular cartilage cells or in insulin-induced ATDC5 chondrogenic cells lentiviral constructs for Nfat1 siRNA were prepared. The H1 RNA polymerase III promoter vector pSIH-CMV/FerL-cG-H1F was obtained from System Biosciences, Mountain View, Calif. This vector contains a copGFP gene, which serves as a fluorescent protein reporter for the transduced cells, wherein the copGFP gene is derived from copepod plankton (*Panalina* sp.). This gene serves as a fluorescent reporter for the transduced cells and allowed us to make articular cartilage cells and ATDC5 chondrogenic cells stably suppressing Nfat1 expression. For siRNA design we utilized mouse/rat Nfat1 specific sequence 5'-GAC-TAT-CTG-AAC-CCT-ATC-G (SEQ ID NO: 1). Bbs I restriction sites were added on both ends of this sequence to enable directional cloning. The oligonucleotides were annealed, phosphorylated by polynucleotide kinase (Promega), and then ligated into pSIH-CMV/FerL-cG-H1F using unique Bbs I site located just downstream of the H1 promoter. Competent *E. coli* cells of DH5α strain (Invitrogen) were transformed, and colonies were screened by PCR with primers flanking the insert. The final construct was verified by sequencing.

Example 9

Preparation of an Nfat1 Overexpression System

By way of comparison, an overexpression system for Nfat1 was also developed. A lentiviral construct for stable expression of constitutively active Nfat1 was generated using a pCDH-EF1-MCS-T2A-copGFP vector (System Biosciences) (see details in Example 10). Mouse Nfat1 cDNA (SEQ ID NO: 2) with multiple serine to alanine mutations in the Nfat1 regulatory domain, which render Nfat1 constitutively active, was obtained from Addgene (plasmid 11792). This cDNA was transferred into the unique Xba site of the lentivector. The final construct was verified by sequencing.

For production of lentiviral particles of either the siRNA construct or the overexpression construct, the packaging cell line 293T HEK (105 cells/ml) was plated on 12-well tissue culture plates and transfected the following day. 3 µg of the transducing vector pLenti4/V5-NFATc2 (i.e., NFATc2 is Nfat1), 0.5 µg of the packaging vector psPAX2, and 0.5 µg of the VSV envelope pMD2.G (Addgene) were co-transfected by ExGen 500 in vitro Transfection Reagent (Fermentas Life Sciences) according to manufacturer's instructions.

It has been shown that the Nfat1-specific siRNA reduces synthesis and excretion of type II collagen and aggrecan from articular cartilage cells and/or insulin-induced ATDC5 chondrogenic cells. In contrast, overexpression of Nfat1 at least partially restores synthesis and excretion of type II collagen and aggrecan from articular cartilage cells and/or insulin-treated ATDC5 chondrogenic cells with Nfat1 siRNA.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

What is claimed is:

1. A method of diagnosing primary osteoarthritis and/or predicting susceptibility to primary osteoarthritis in a subject, comprising:
measuring the subject's Nfat1 protein or gene expression level or an Nfat1 transcription factor activity in a tissue sample selected from cartilage or peripheral blood cells;
diagnosing primary osteoarthritis and/or predicting susceptibility to primary osteoarthritis in the subject based on the measuring, wherein the diagnosing includes comparing the subject's Nfat1 protein or gene expression level or the Nfat1 transcription factor activity to a wild-type control Nfat1 protein or gene expression level or an Nfat1 transcription factor activity, wherein having Nfat1 protein or gene expression levels or Nfat1 transcription factor activity reduced by at least 50% relative to the wild-type control is predictive of susceptibility to osteoarthritis;
administering at least one bioactive substance selected from the group consisting of an Nfat1 protein and a nucleic acid encoding an Nfat1 protein to the subject; and
determining whether the bioactive substance increases at least one of Nfat1 protein expression, Nfat1 gene expression, or Nfat1 transcription factor activity in cartilage or peripheral blood cells in the subject.

2. A method as recited in claim 1, wherein the tissue sample includes articular cartilage cells.

3. A method as recited in claim 1, further comprising measuring type II collagen production by articular cartilage cells in the subject.

4. A method as recited in claim 1, further comprising measuring aggrecan production by articular cartilage cells in the subject.

5. A method as recited in claim 1, further comprising probing the subject's genome for sequence variations in Nfat1.

6. A method as recited in claim 1, further comprising determining whether the subject has degenerative articular cartilage disease.

7. A method as recited in claim 1, further comprising measuring articular cartilage degeneration.

8. A method as recited in claim 1, measuring at least one of an activity or a concentration of at least one downstream effector of Nfat1.

9. A method as recited in claim 8, wherein Nfat1 and/or the downstream effectors of Nfat1 affect levels of at least one of:

matrix metalloproteinase 1a (Mmp1a);
matrix metalloproteinase 13 (Mmp13);
Adamts5 (i.e., a disintegrin and metalloproteinase with thrombospondin motifs);
tissue inhibitor of metalloproteinase-1 (Timp1);
aggrecan;
a collagen protein;
β-catenin;
interleukin-1β (IL-1β);
interleukin-6 (IL-6); or
interleukin-17α (IL-17α).

10. A method of diagnosing primary osteoarthritis and/or predicting susceptibility to primary osteoarthritis in a subject, comprising:
measuring a subject's Nfat1 protein or gene expression level or an Nfat1 transcription factor activity in a tissue sample selected from cartilage or peripheral blood cells; and
diagnosing primary osteoarthritis and/or predicting susceptibility to primary osteoarthritis in the subject based on the measuring, wherein having Nfat1 protein or gene expression levels or Nfat1 transcription factor activity reduced by at least 50% relative to the wild-type control is predictive of susceptibility to osteoarthritis; and
administering an agent to the subject to increase Nfat1 protein or gene expression or to increase Nfat1 transcription factor activity in cartilage tissue in the subject, wherein the agent is selected from the group consisting of an Nfat1 protein, a nucleic acid encoding an Nfat1 protein, and combinations thereof.

11. A method as recited in claim 10, further comprising determining whether the administered agent increases intracellular synthesis of Nfat1 protein, increases nuclear translocation of Nfat1 protein, increases Nfat1 transcription factor activity, and/or affects a downstream effector of Nfat1.

12. A method of claim 11, further comprising subsequent to administering the agent: measuring the subject's Nfat1 protein or gene expression level or an Nfat1 transcription factor activity in cartilage or peripheral blood cells; and comparing the subject's Nfat1 protein or gene expression level or the Nfat1 transcription factor activity to a wild-type control Nfat1 protein or gene expression level or an Nfat1 transcription factor activity.

\* \* \* \* \*

UNITED STATES PATENT AND TRADEMARK OFFICE
CERTIFICATE OF CORRECTION

| | | |
|---|---|---|
| PATENT NO. | : 8,709,997 B2 | Page 1 of 1 |
| APPLICATION NO. | : 13/601312 | |
| DATED | : April 29, 2014 | |
| INVENTOR(S) | : Jinxi Wang | |

It is certified that error appears in the above-identified patent and that said Letters Patent is hereby corrected as shown below:

TITLE PAGE: ITEM SHOULD READ

Related U.S. Application data

(62) Division of application No. 12/407,536, filed on Mar. 19, 2009, now Pat. No. 8,263,546.
(60) Provisional application No. 61/038,591, filed on Mar. 21, 2008.

Signed and Sealed this
Thirteenth Day of January, 2015

Michelle K. Lee
*Deputy Director of the United States Patent and Trademark Office*